(12) United States Patent
Al-Ali et al.

(10) Patent No.: US 11,974,841 B2
(45) Date of Patent: May 7, 2024

(54) RESPIRATION PROCESSOR

(71) Applicant: MASIMO CORPORATION, Irvine, CA (US)

(72) Inventors: Ammar Al-Ali, San Juan Capistrano, CA (US); Walter M. Weber, Laguna Hills, CA (US); Anmol B. Majmudar, Irvine, CA (US); Gilberto Sierra, Mission Viejo, CA (US); Sung Uk Lee, Irvine, CA (US); Mohamed Diab, Ladera Ranch, CA (US); Valery G. Telfort, Irvine, CA (US); Marc Pelletier, Vaudreuil-Dorion (CA); Boris Popov, Montreal (CA)

(73) Assignee: MASIMO CORPORATION, Irvine, CA (US)

( * ) Notice: Subject to any disclaimer, the term of this patent is extended or adjusted under 35 U.S.C. 154(b) by 1120 days.

(21) Appl. No.: 16/791,241

(22) Filed: Feb. 14, 2020

(65) Prior Publication Data
US 2020/0253509 A1 Aug. 13, 2020

Related U.S. Application Data

(63) Continuation of application No. 15/669,201, filed on Aug. 4, 2017, now Pat. No. 10,595,747, which is a (Continued)

(51) Int. Cl.
*A61B 5/08* (2006.01)
*A61B 5/00* (2006.01)
*A61B 7/00* (2006.01)

(52) U.S. Cl.
CPC .............. *A61B 5/0816* (2013.01); *A61B 5/08* (2013.01); *A61B 7/003* (2013.01); *A61B 5/7221* (2013.01); *A61B 5/7257* (2013.01)

(58) Field of Classification Search
CPC ......... A61B 5/0816; A61B 7/003; A61B 5/08; A61B 5/7221; A61B 5/7257
See application file for complete search history.

(56) References Cited

U.S. PATENT DOCUMENTS

| | | | |
|---|---|---|---|
| 3,682,161 A | 8/1972 | Alibert | |
| 4,127,749 A | 11/1978 | Atoji et al. | |

(Continued)

FOREIGN PATENT DOCUMENTS

| | | |
|---|---|---|
| CA | 2262236 | 4/2008 |
| EP | 0716628 | 12/1998 |

(Continued)

OTHER PUBLICATIONS

US 8,845,543 B2, 09/2014, Diab et al. (withdrawn)

(Continued)

*Primary Examiner* — Christian Jang
(74) *Attorney, Agent, or Firm* — Knobbe, Martens, Olson & Bear, LLP

(57) ABSTRACT

Respiratory rate can be calculated from an acoustic input signal using time domain and frequency domain techniques. Confidence in the calculated respiratory rate can also be calculated using time domain and frequency domain techniques. Overall respiratory rate and confidence values can be obtained from the time and frequency domain calculations. The overall respiratory rate and confidence values can be output for presentation to a clinician.

20 Claims, 30 Drawing Sheets

Related U.S. Application Data continuation of application No. 12/905,384, filed on Oct. 15, 2010, now Pat. No. 9,724,016.

(60) Provisional application No. 61/326,200, filed on Apr. 20, 2010, provisional application No. 61/252,594, filed on Oct. 16, 2009.

(56) References Cited

U.S. PATENT DOCUMENTS

| | | | |
|---|---|---|---|
| 4,326,143 | A | 4/1982 | Guth et al. |
| 4,507,653 | A | 3/1985 | Bayer |
| 4,537,200 | A | 8/1985 | Widrow |
| 4,685,140 | A | 8/1987 | Mount, II |
| 4,714,341 | A | 12/1987 | Hamaguri |
| 4,848,901 | A | 7/1989 | Hood, Jr. |
| 4,884,809 | A | 12/1989 | Rowan |
| 4,958,638 | A | 9/1990 | Sharpe et al. |
| 4,960,128 | A | 10/1990 | Gordon et al. |
| 4,964,408 | A | 10/1990 | Hink et al. |
| 5,033,032 | A | 7/1991 | Houghtaling |
| 5,041,187 | A | 8/1991 | Hink et al. |
| 5,069,213 | A | 12/1991 | Polczynski |
| 5,143,078 | A | 9/1992 | Mather et al. |
| 5,163,438 | A | 11/1992 | Gordon et al. |
| 5,273,036 | A | 12/1993 | Kronberg et al. |
| 5,309,922 | A | 5/1994 | Schechter et al. |
| 5,319,355 | A | 6/1994 | Russek |
| 5,337,744 | A | 8/1994 | Branigan |
| 5,341,805 | A | 8/1994 | Stavridi et al. |
| 5,353,798 | A | 10/1994 | Sieben |
| D353,195 | S | 12/1994 | Savage et al. |
| D353,196 | S | 12/1994 | Savage et al. |
| 5,377,302 | A | 12/1994 | Tsiang |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| 5,448,996 | A | 9/1995 | Bellin et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,403 | A | 6/1997 | Birchler et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,191 | A | 9/1997 | Gerdt |
| 5,671,914 | A | 9/1997 | Kalkhoran et al. |
| 5,685,299 | A | 11/1997 | Diab et al. |
| 5,724,983 | A | 3/1998 | Selker et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,819,007 | A | 10/1998 | Elghazzawi |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,865,168 | A | 2/1999 | Isaza |
| 5,865,736 | A | 2/1999 | Baker, Jr. et al. |
| 5,890,929 | A | 4/1999 | Mills et al. |
| 5,904,654 | A | 5/1999 | Wohltmann et al. |
| 5,919,134 | A | 7/1999 | Diab |
| 5,928,156 | A | 7/1999 | Krumbiegel |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,029,665 | A | 2/2000 | Berthon-Jones |
| 6,036,642 | A | 3/2000 | Diab et al. |
| 6,040,578 | A | 3/2000 | Malin et al. |
| 6,045,509 | A | 4/2000 | Caro et al. |
| 6,064,910 | A | 5/2000 | Andersson et al. |
| 6,066,204 | A | 5/2000 | Haven |
| 6,067,462 | A | 5/2000 | Diab et al. |
| 6,081,735 | A | 6/2000 | Diab et al. |
| 6,083,172 | A | 7/2000 | Baker et al. |
| 6,088,607 | A | 7/2000 | Diab et al. |
| 6,091,973 | A | 7/2000 | Colla et al. |
| 6,110,522 | A | 8/2000 | Lepper, Jr. et al. |
| 6,112,171 | A | 8/2000 | Sugiyama et al. |
| 6,115,673 | A | 9/2000 | Malin et al. |
| 6,124,597 | A | 9/2000 | Shehada |
| 6,128,521 | A | 10/2000 | Marro et al. |
| 6,129,675 | A | 10/2000 | Jay |
| 6,138,675 | A | 10/2000 | Berthon-Jones |
| 6,139,505 | A | 10/2000 | Murphy |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,168,568 | B1 | 1/2001 | Gavriely |
| 6,178,343 | B1 | 1/2001 | Bindszus et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,248,083 | B1 | 6/2001 | Smith et al. |
| 6,253,097 | B1 | 6/2001 | Aronow et al. |
| 6,254,551 | B1 | 7/2001 | Varis |
| 6,255,708 | B1 | 7/2001 | Sudharsanan et al. |
| 6,256,523 | B1 | 7/2001 | Diab et al. |
| 6,261,238 | B1 | 7/2001 | Gavriely |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,331,162 | B1 | 12/2001 | Mitchell |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,383,143 | B1 | 5/2002 | Rost |
| 6,388,240 | B2 | 5/2002 | Schulz et al. |
| 6,397,091 | B2 | 5/2002 | Diab et al. |

(56) References Cited

U.S. PATENT DOCUMENTS

| | | |
|---|---|---|
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,443,907 B1 | 9/2002 | Mansy et al. |
| 6,463,311 B1 | 10/2002 | Diab |
| 6,470,199 B1 | 10/2002 | Kopotic et al. |
| 6,486,588 B2 | 11/2002 | Doron et al. |
| 6,487,429 B2 | 11/2002 | Hockersmith et al. |
| 6,491,647 B1 | 12/2002 | Bridger et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,647,280 B2 | 11/2003 | Bahr et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,659,960 B2 | 12/2003 | Derksen et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,709,402 B2 | 3/2004 | Dekker |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kastle |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,754,516 B2 | 6/2004 | Mannheimer |
| 6,760,607 B2 | 7/2004 | Al-Ali |
| 6,766,038 B1 | 7/2004 | Sakuma et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,581 B1 | 1/2005 | El-Solh et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,869,402 B2 | 3/2005 | Arnold |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,194,306 B1 | 3/2007 | Turcott |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,267,652 B2 | 9/2007 | Coyle et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,146 B1 | 4/2008 | Bharmi et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |

(56) References Cited

U.S. PATENT DOCUMENTS

| | | |
|---|---|---|
| 7,383,070 B2 | 6/2008 | Diab et al. |
| 7,395,158 B2 | 7/2008 | Monfre et al. |
| 7,398,115 B2 | 7/2008 | Lynn |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,539,533 B2 | 5/2009 | Tran |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,690,378 B1 | 4/2010 | Turcott |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |

(56) References Cited

U.S. PATENT DOCUMENTS

| | | | |
|---|---|---|---|
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,478,538 B2 | 7/2013 | McGonigle et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,597,274 B2 | 12/2013 | Sloan |
| 8,600,467 B2 | 12/2013 | Al-Ali et al. |
| 8,606,342 B2 | 12/2013 | Diab |
| 8,622,902 B2 | 1/2014 | Woehrle |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,949 B2 | 7/2014 | Baker |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,135,398 B2 | 9/2015 | Kaib |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,220,440 B2 | 12/2015 | Addison et al. |

(56) References Cited

U.S. PATENT DOCUMENTS

| | | |
|---|---|---|
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 1/2016 | Abdul-Hafiz et al. |
| 9,267,572 B2 | 2/2016 | Barker et al. |
| 9,277,880 B2 | 2/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,378,637 B2 | 6/2016 | Kaib |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,659,475 B2 | 5/2017 | Kaib |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,968,266 B2 | 5/2018 | An et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |

(56) References Cited

U.S. PATENT DOCUMENTS

| | | |
|---|---|---|
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Ai-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |

(56) References Cited

U.S. PATENT DOCUMENTS

| | | |
|---|---|---|
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| 11,766,198 B2 | 9/2023 | Pauley et al. |
| D1,000,975 S | 10/2023 | Al-Ali et al. |
| 2001/0002206 A1 | 5/2001 | Diab et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2002/0193670 A1 | 12/2002 | Garfield et al. |
| 2003/0013975 A1 | 1/2003 | Kiani |
| 2003/0015368 A1 | 1/2003 | Cybulski et al. |
| 2003/0018243 A1 | 1/2003 | Gerhardt et al. |
| 2003/0065269 A1 | 4/2003 | Vetter |
| 2003/0076494 A1 | 4/2003 | Bonin et al. |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0163033 A1 | 8/2003 | Dekker et al. |
| 2003/0163054 A1 | 8/2003 | Dekker |
| 2003/0212312 A1 | 11/2003 | Coffin, IV et al. |
| 2004/0010202 A1 | 1/2004 | Nakatani |
| 2004/0059203 A1 | 3/2004 | Guerrero |
| 2004/0060362 A1 | 4/2004 | Kjellmann et al. |
| 2004/0106163 A1 | 6/2004 | Workman, Jr. et al. |
| 2004/0133087 A1 | 7/2004 | Ali et al. |
| 2004/0158162 A1 | 8/2004 | Narimatsu |
| 2004/0225332 A1 | 11/2004 | Gebhardt |
| 2004/0260186 A1 | 12/2004 | Dekker |
| 2005/0027205 A1 | 2/2005 | Tarassenko et al. |
| 2005/0048456 A1 | 3/2005 | Chefd'hotel et al. |
| 2005/0055276 A1 | 3/2005 | Kiani et al. |
| 2005/0070774 A1 | 3/2005 | Addison et al. |
| 2005/0107699 A1 | 5/2005 | Loftman |
| 2005/0116820 A1 | 6/2005 | Goldreich |
| 2005/0199056 A1 | 9/2005 | Strong |
| 2005/0234317 A1 | 10/2005 | Kiani |
| 2006/0047215 A1 | 3/2006 | Newman et al. |
| 2006/0073719 A1 | 4/2006 | Kiani |
| 2006/0129216 A1 | 6/2006 | Hastings et al. |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189871 A1 | 8/2006 | Al-Ali et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0238333 A1 | 10/2006 | Welch et al. |
| 2006/0241510 A1 | 10/2006 | Halperin et al. |
| 2006/0258921 A1 | 11/2006 | Addison et al. |
| 2007/0073116 A1 | 3/2007 | Kiani et al. |
| 2007/0093721 A1 | 4/2007 | Lynn et al. |
| 2007/0129643 A1 | 6/2007 | Kwok et al. |
| 2007/0129647 A1 | 6/2007 | Lynn |
| 2007/0135725 A1 | 6/2007 | Hatlestad |
| 2007/0149860 A1 | 6/2007 | Lynn et al. |
| 2007/0163353 A1 | 7/2007 | Lec et al. |
| 2007/0180140 A1 | 8/2007 | Welch et al. |
| 2007/0185397 A1 | 8/2007 | Govari et al. |
| 2007/0213619 A1 | 9/2007 | Linder |
| 2007/0239057 A1 | 10/2007 | Pu et al. |
| 2007/0244377 A1 | 10/2007 | Cozad et al. |
| 2007/0282212 A1 | 12/2007 | Sierra et al. |
| 2007/0282478 A1 | 12/2007 | Al-Ali et al. |
| 2008/0013747 A1 | 1/2008 | Tran |
| 2008/0039735 A1 | 2/2008 | Hickerson |
| 2008/0064965 A1 | 3/2008 | Jay et al. |
| 2008/0071185 A1 | 3/2008 | Beck et al. |
| 2008/0076972 A1 | 3/2008 | Dorogusker et al. |
| 2008/0094228 A1 | 4/2008 | Welch et al. |
| 2008/0103375 A1 | 5/2008 | Kiani |
| 2008/0119716 A1 | 5/2008 | Boric-Lubecke et al. |
| 2008/0161878 A1 | 7/2008 | Tehrani et al. |
| 2008/0177195 A1 | 7/2008 | Armitstead |
| 2008/0188733 A1 | 8/2008 | Al-Ali |
| 2008/0188760 A1 | 8/2008 | Al-Ali |
| 2008/0218153 A1 | 9/2008 | Patel et al. |
| 2008/0221418 A1 | 9/2008 | Al-Ali et al. |
| 2008/0275349 A1 | 11/2008 | Halperin et al. |
| 2008/0304580 A1 | 12/2008 | Ichiyama |
| 2009/0018409 A1* | 1/2009 | Banet .............. A61B 5/0816 600/301 |
| 2009/0018429 A1 | 1/2009 | Saliga et al. |
| 2009/0018453 A1 | 1/2009 | Banet et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0112096 A1 | 4/2009 | Tamura |
| 2009/0160654 A1 | 6/2009 | Yang |
| 2009/0167332 A1 | 7/2009 | Forbes |
| 2009/0187065 A1 | 7/2009 | Basinger |
| 2009/0227882 A1 | 9/2009 | Foo |
| 2009/0240119 A1 | 9/2009 | Schwaibold et al. |
| 2009/0247848 A1 | 10/2009 | Baker |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2009/0312612 A1 | 12/2009 | Rantala |
| 2010/0004518 A1 | 1/2010 | Vo et al. |
| 2010/0004552 A1 | 1/2010 | Zhang et al. |
| 2010/0014761 A1 | 1/2010 | Addison et al. |
| 2010/0016682 A1 | 1/2010 | Schluess et al. |
| 2010/0016693 A1 | 1/2010 | Addison |
| 2010/0030040 A1 | 2/2010 | Poeze et al. |
| 2010/0099064 A1 | 4/2010 | O'Reilly et al. |
| 2010/0130873 A1 | 5/2010 | Yuen |
| 2010/0204550 A1 | 8/2010 | Heneghan |
| 2010/0234718 A1 | 9/2010 | Sampath et al. |
| 2010/0261979 A1 | 10/2010 | Kiani |
| 2010/0270257 A1 | 10/2010 | Wachman et al. |
| 2010/0274099 A1 | 10/2010 | Telfort et al. |
| 2010/0295686 A1 | 11/2010 | Sloan |
| 2010/0298661 A1 | 11/2010 | McCombie et al. |
| 2010/0298730 A1 | 11/2010 | Tarassenko et al. |
| 2010/0324377 A1 | 12/2010 | Woehrle |
| 2010/0331903 A1 | 12/2010 | Zhang |
| 2011/0001605 A1 | 1/2011 | Kiani |
| 2011/0009710 A1 | 1/2011 | Kroeger et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0040713 A1 | 2/2011 | Colman |
| 2011/0066062 A1 | 3/2011 | Banet et al. |
| 2011/0074409 A1 | 3/2011 | Stoughton |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0118573 A1 | 5/2011 | McKenna |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0172561 A1 | 7/2011 | Kiani et al. |
| 2011/0208015 A1 | 8/2011 | Welch et al. |
| 2011/0209915 A1 | 9/2011 | Telfort et al. |

(56) References Cited

U.S. PATENT DOCUMENTS

| | | |
|---|---|---|
| 2011/0213212 A1 | 9/2011 | Al-Ali |
| 2011/0222371 A1 | 9/2011 | Liu et al. |
| 2011/0230733 A1 | 9/2011 | Al-Ali et al. |
| 2011/0237911 A1 | 9/2011 | Lamego et al. |
| 2012/0016255 A1 | 1/2012 | Masuo |
| 2012/0059267 A1 | 3/2012 | Lamego et al. |
| 2012/0070013 A1 | 3/2012 | Vau |
| 2012/0101344 A1 | 4/2012 | Desjardins |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0253140 A1 | 10/2012 | Addison et al. |
| 2012/0262298 A1 | 10/2012 | Bohm |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego |
| 2013/0041591 A1 | 3/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0116578 A1 | 5/2013 | An et al. |
| 2013/0128690 A1 | 5/2013 | Gopalan |
| 2013/0137936 A1 | 5/2013 | Baker, Jr. et al. |
| 2013/0162433 A1 | 6/2013 | Muhsin et al. |
| 2013/0190581 A1 | 7/2013 | Al-Ali et al. |
| 2013/0190595 A1 | 7/2013 | Oraevsky |
| 2013/0197328 A1 | 8/2013 | Diab et al. |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | Dalvi et al. |
| 2013/0296713 A1 | 11/2013 | Al-Ali et al. |
| 2013/0296726 A1 | 11/2013 | Nievauer et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Lamego et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani et al. |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Diab et al. |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |

(56) References Cited

U.S. PATENT DOCUMENTS

| | | |
|---|---|---|
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |

(56) References Cited

U.S. PATENT DOCUMENTS

| | | |
|---|---|---|
| 2019/0254578 A1 | 8/2019 | Lamego |
| 2019/0261857 A1 | 8/2019 | Al-Ali |
| 2019/0320906 A1 | 10/2019 | Olsen |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ai |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2003-329719 | 11/2003 |
| WO | WO 1994/005207 | 3/1994 |
| WO | WO 1994/013207 | 6/1994 |
| WO | WO 1995/029632 | 11/1995 |
| WO | WO 1999/053277 | 10/1999 |
| WO | WO 2000/010462 | 3/2000 |
| WO | WO 2001/034033 | 5/2001 |
| WO | WO 2001/078059 | 10/2001 |
| WO | WO 2001/097691 | 12/2001 |
| WO | WO 2002/003042 | 1/2002 |
| WO | WO 2003/058646 | 7/2003 |
| WO | WO 2003/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/080469 | 7/2008 |
| WO | WO 2008/148172 | 12/2008 |
| WO | WO 2009/093159 | 7/2009 |
| WO | WO 2009/137524 | 11/2009 |

OTHER PUBLICATIONS

US 9,579,050 B2, 02/2017, Al-Ali (withdrawn)
U.S. Appl. No. 15/851,176, Non-Invasive Monitoring of Respiratory Rate, Heart Rate and Apnea, filed Dec. 21, 2017.
U.S. Appl. No. 16/557,198, Acoustic Physiological Monitoring System, filed Aug. 30, 2019.
U.S. Appl. No. 16/155,456, Acoustic Respiratory Event Processor, filed Oct. 9, 2018.
U.S. Appl. No. 16/119,215, Plethysmographic Respiration Processor, filed Aug. 31, 2018.
U.S. Appl. No. 16/459,955, Respiration Event Processor, filed Jul. 2, 2019.
U.S. Appl. No. 13/900,984, Plethysmographic Respiration Analysis System, filed May 23, 2013.
Analog Devices, 12-Bit Serial Input Multiplying D/A Converter, Product Data Sheet, 2000.
Chambrin, M-C.; "Alarms in the intensive care unit: how can the number of false alarms be reduced?"; Critical Care Aug. 2001, vol. 5 No. 4; p. 1-5.
Eldor et al., "A device for monitoring ventilation during anaesthesia; the paratracheal audible respiratory monitor", Canadian Journal of Anaesthesia, 1990, vol. 9, No. 1, p. 95-98.
GE Healthcare, "Transport ProTM Patient Monitor Operator's Manual" Apr. 9, 2007, in 286 pages.
Gorges, M. et al; "Improving Alarm Performance in the Medical Intensive Care Unit Using Delays and Clinical Context"; Technology, Computing, and Simulation; vol. 108, No. 5, May 2009; p. 1546-1552.
Imhoff, M. et al; "Alarm Algorithms in Critical Care Monitoring"; Anesth Analg 2006;102:1525-37.
International Search Report & Written Opinion, PCT Application PCT/US2010/052758, dated Feb. 10, 2011; 12 pages.
International Search Report & Written Opinion, PCT Application PCT/US2010/058981, dated Feb. 17, 2011; 11 pages.
International Search Report and Written Opinion issued in application No. PCT/US2010/052756 dated Feb. 6, 2012.
International Search Report, PCT Application PCT/CA2003/000536, dated Dec. 11, 2003; 2 pages.
International Search Report, PCT Application PCT/US2009/069287, dated Mar. 30, 2010; 7 pages.
Japanese Office Action for JP Application No. 2007-506626 dated Mar. 1, 2011.
Sierra et al., Monitoring Respiratory Rate Based on Tracheal Sounds. First Experieances, Proceedings of the 26th Annual Int'l Conf. of the IEEE EMBS (Sep. 2004), 317-320.
Watt, R. C.; "Alarms and Anesthesia. Challenges in the design of Intelligent systems for Patient Monitoring"; IEEE Engineering in Medicine and biology; Dec. 1993, p. 34-41.
Welch Allyn, ECG ASIC, Product Data Sheete, 2001.

(56) References Cited

OTHER PUBLICATIONS

Supplementary Partial European Search Report for International Application No. 05732095.4, dated Jun. 26, 2009 in 4 pages.
Theimer et al., "Definitions of audio features for music content description", Algorithm Engineering Report TR08-2-001, Feb. 2008.
Stewart, C., Larson, V., "Detection and classification of acoustic signals from fixed-wing aircraft," Systems Engineering, CH3051-0/91/0000-0025, IEEE, 1991.
Johnston, Development of a Signal Processing Library for Extraction of Sp02, HR, HRV, and RR from Photoplethysmographic Waveforms, Thesis: Degree of Master of Science, Worcester Polytechnic Institute, date of presentation/defense Jul. 17, 2006, date listed Jul. 27, 2006.
Hsu, "Signals and Systems", Schaum's Theory and Problems, 1995, Ch. 3, p. 121.
Smith, "The Scientist and Engineer's Guide to Digital Signal Processing", https://www.dspguide.com/ch17/2.htm, Ch. 17 and Ch. 18, 2 book editions, original 1997, updated 2002, pp. 297-318.

\* cited by examiner

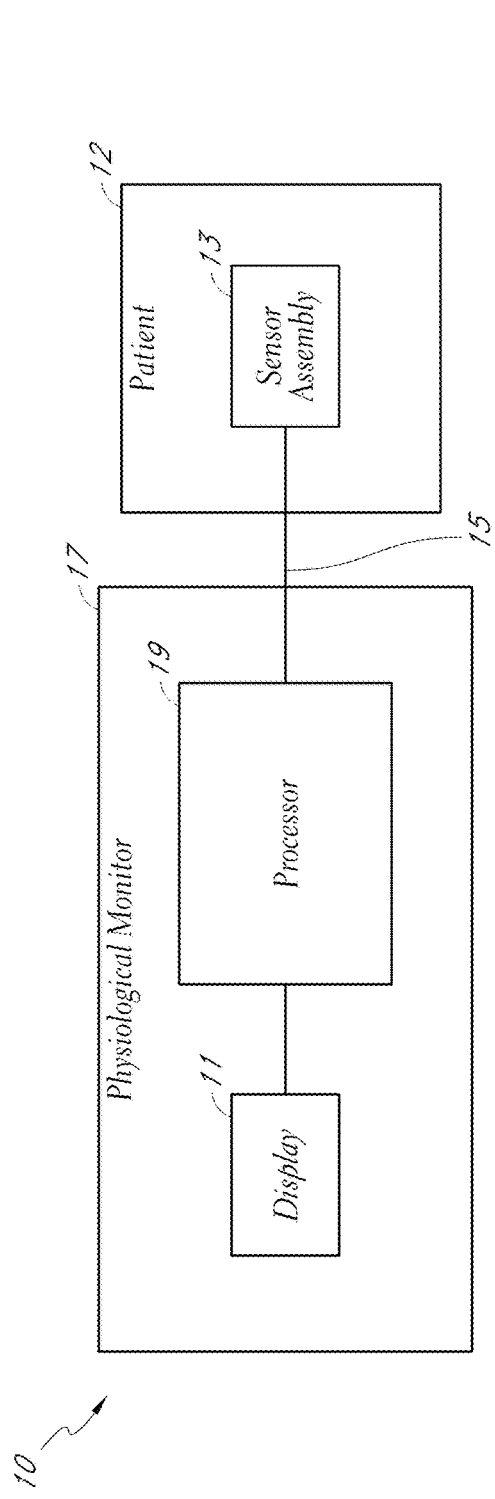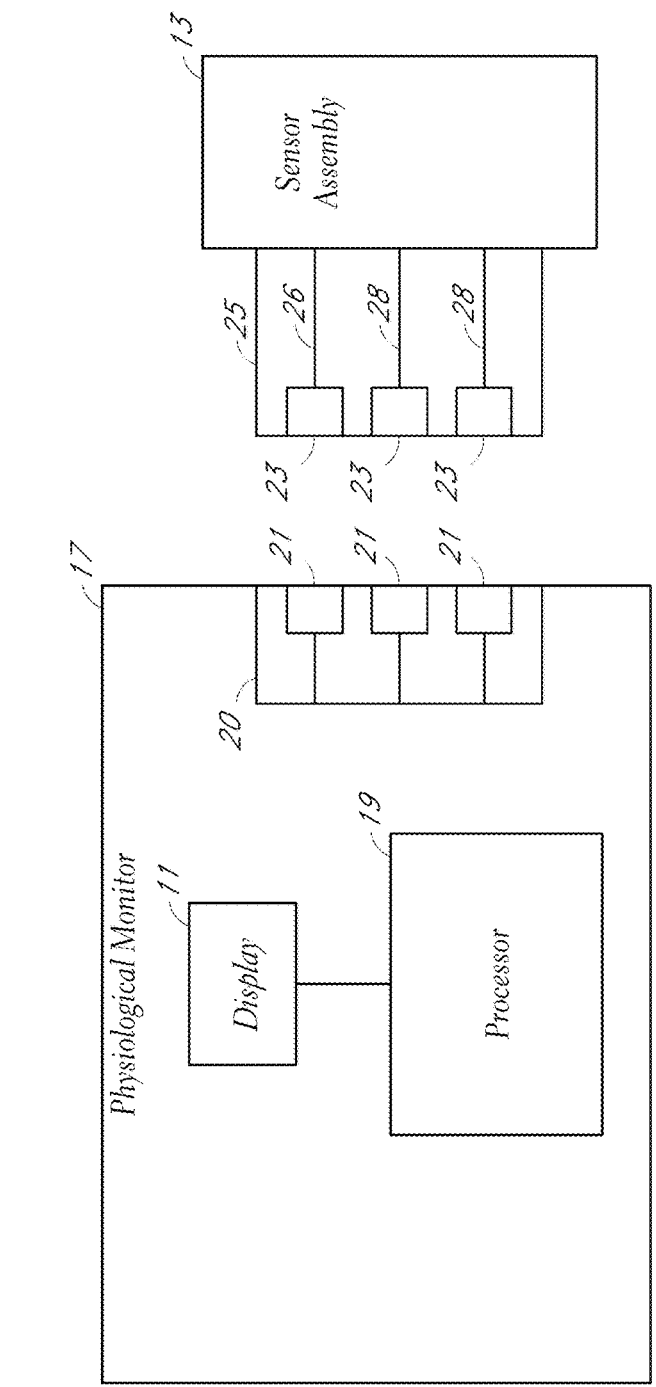
FIG. 1A
FIG. 1B

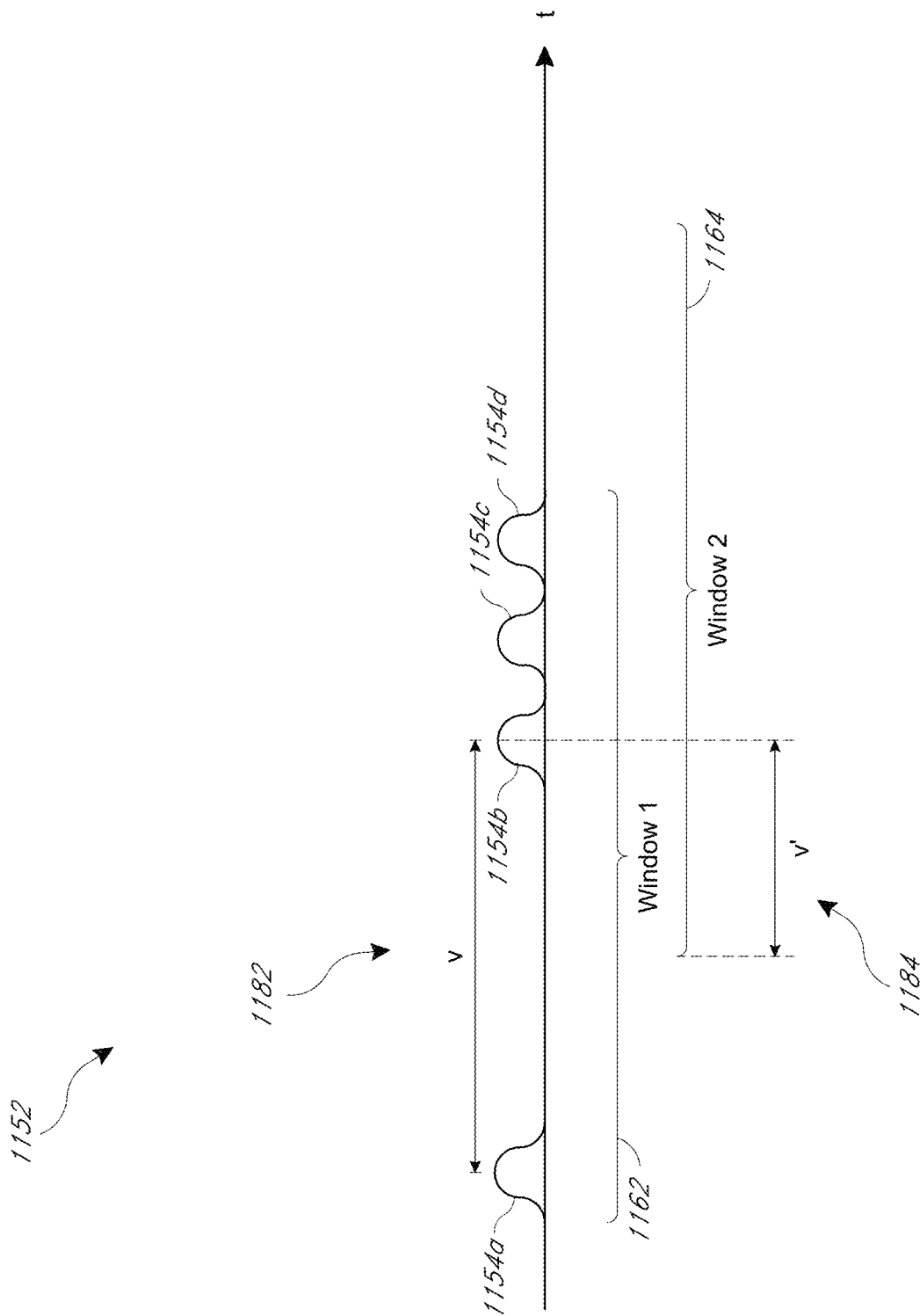

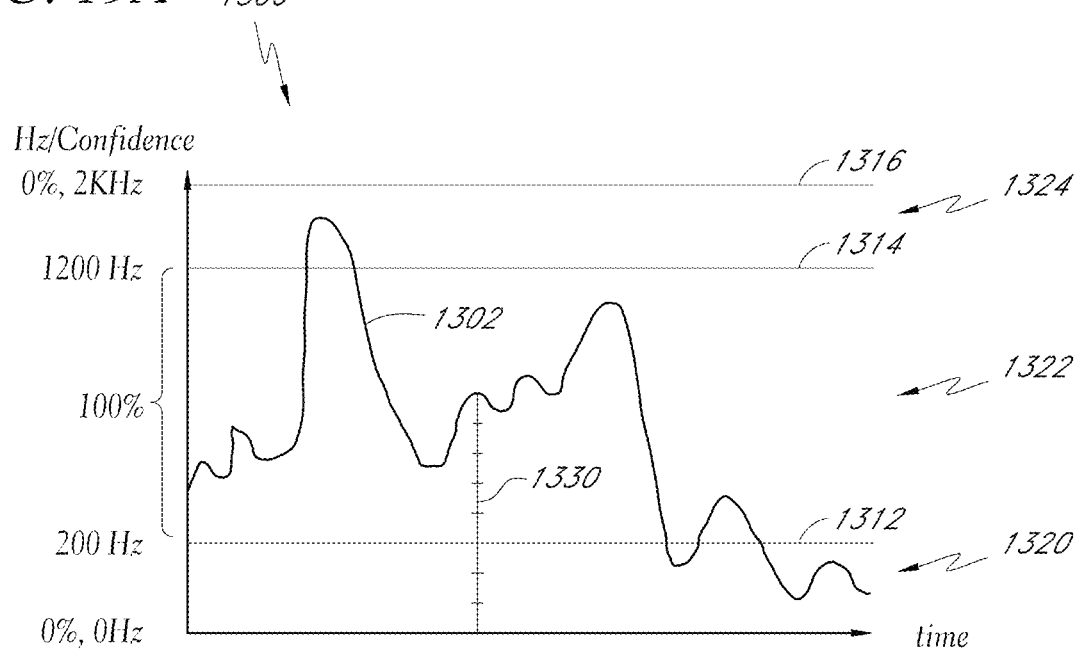

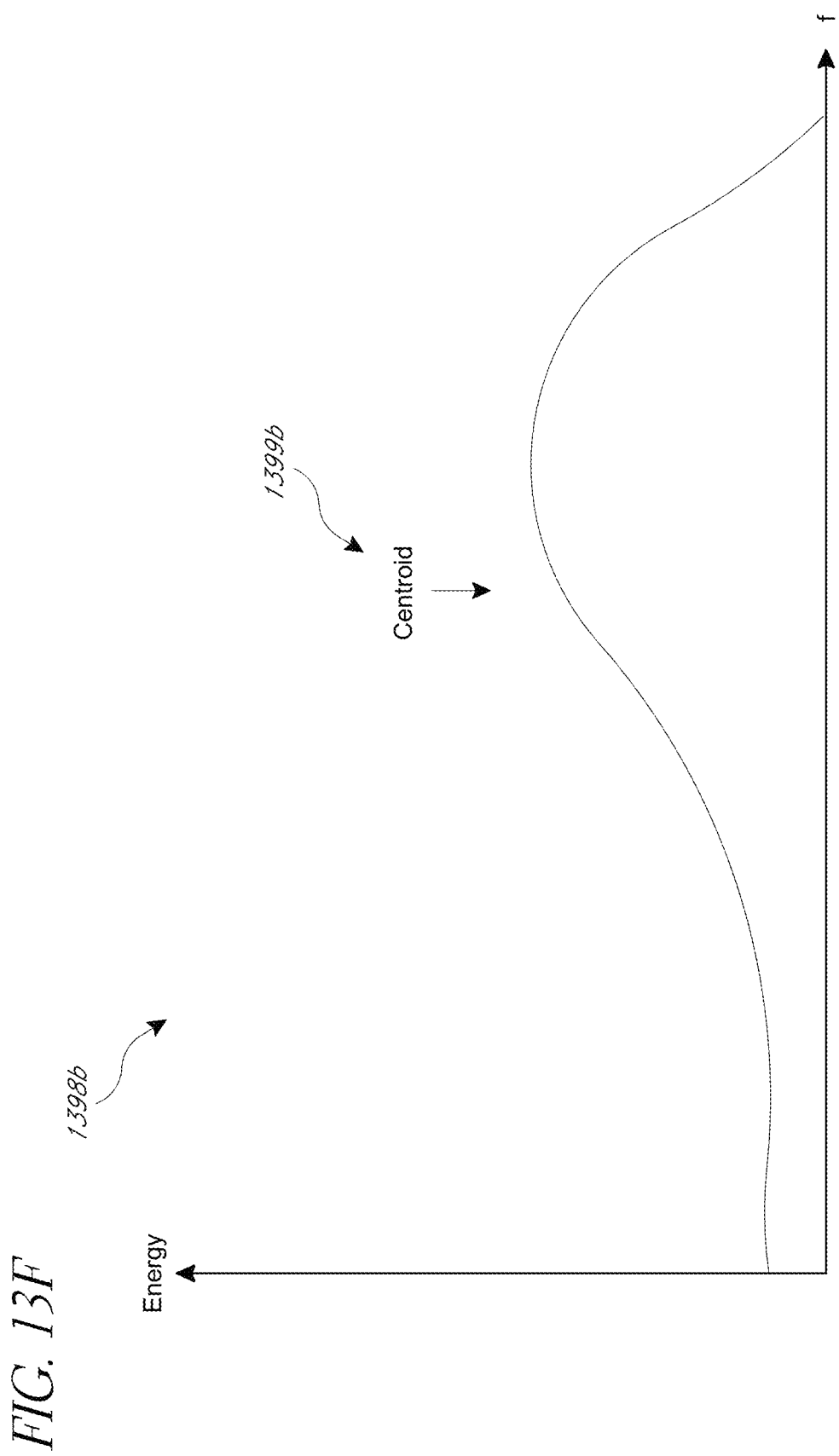

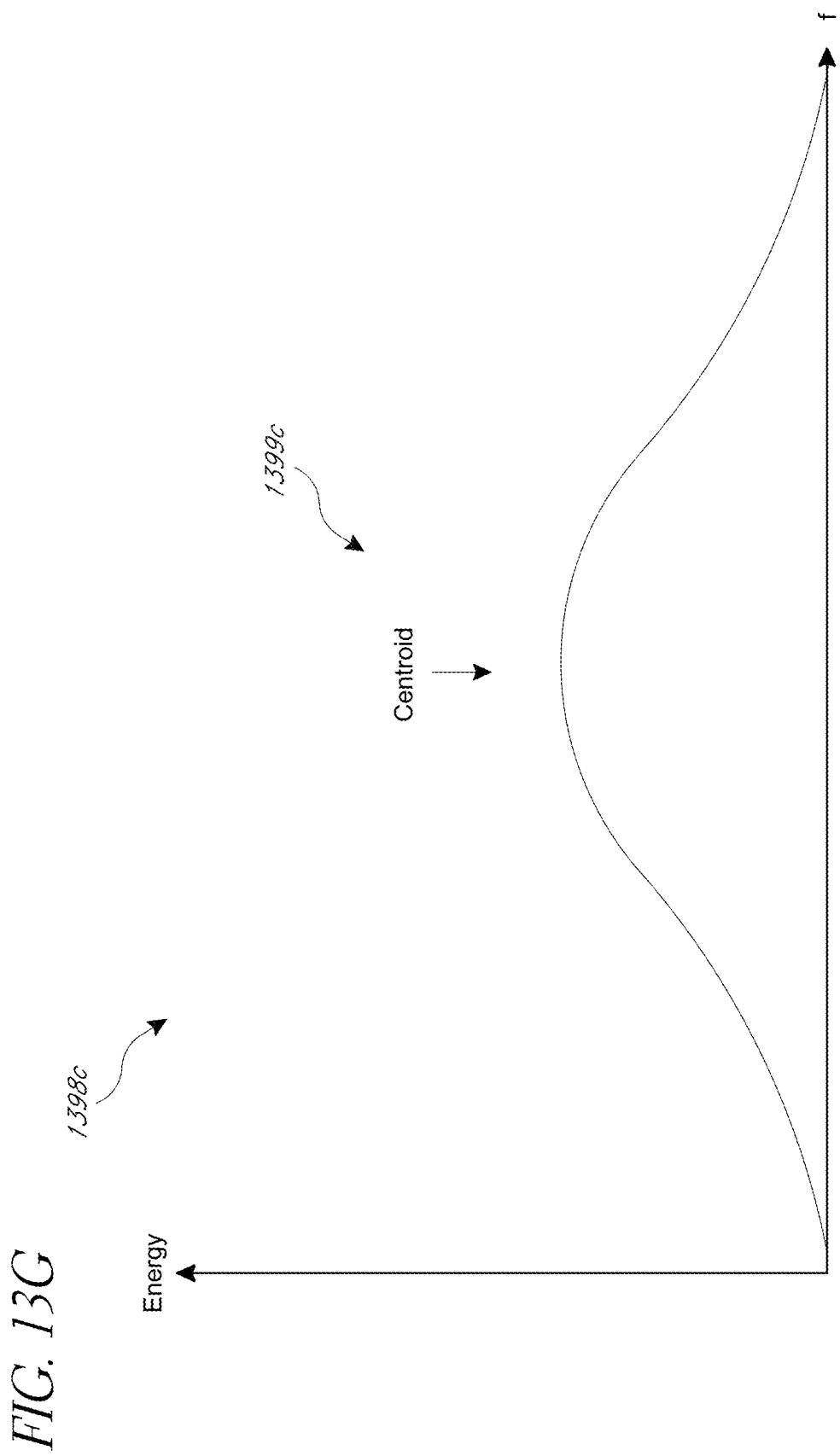

RESPIRATION PROCESSOR

RELATED APPLICATIONS

This application is a continuation of U.S. patent application Ser. No. 15/669,201, filed Aug. 4, 2017, entitled "RESPIRATION PROCESSOR," which is a continuation of U.S. patent application Ser. No. 12/905,384, filed Oct. 15, 2010, entitled "RESPIRATION PROCESSOR," which claims priority from U.S. Provisional Patent Application No. 61/252,594 filed Oct. 16, 2009, entitled "Respiration Processor," and from U.S. Provisional Patent Application No. 61/326,200, filed Apr. 20, 2010, entitled "Respiration Processor," the disclosures of which are hereby incorporated by reference in their entirety.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

SUMMARY

Respiratory rate can be calculated from an acoustic input signal using time domain and frequency domain techniques. Confidence in the calculated respiratory rate can also be calculated using time domain and frequency domain techniques. Overall respiratory rate and confidence values can be obtained from the time and frequency domain calculations. The overall respiratory rate and confidence values can be output for presentation to a clinician.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIGS. 1A-B are block diagrams illustrating physiological monitoring systems in accordance with embodiments of the disclosure.

FIGS. 11B through 11D illustrate example time domain waveforms that can be analyzed by the time domain respiratory rate processor.

FIG. 13A illustrates an example spectrogram.

FIGS. 13E through 13G illustrate example spectrums for computing centroids.

DETAILED DESCRIPTION

Various embodiments will be described hereinafter with reference to the accompanying drawings. These embodiments are illustrated and described by example only, and are not intended to be limiting.

Acoustic sensors, including piezoelectric acoustic sensors, can be used to measure breath sounds and other biological sounds of a patient. Breath sounds obtained from an acoustic sensor can be processed by a patient monitor to derive one or more physiological parameters of a patient, including respiratory rate. For purposes of illustration, this disclosure is described primarily in the context of respiratory rate. However, the features described herein can be applied to other respiratory parameters, including, for example, inspiratory time, expiratory time, inspiratory to expiratory ratio, inspiratory flow, expiratory flow, tidal volume, minute volume, apnea duration, breath sounds (including, e.g., rales, rhonchi, or stridor), changes in breath sounds, and the like. Moreover, the features described herein can also be applied to other physiological parameters and/or vital signs derived from physiological sensors other than acoustic sensors.

Figure 1C:
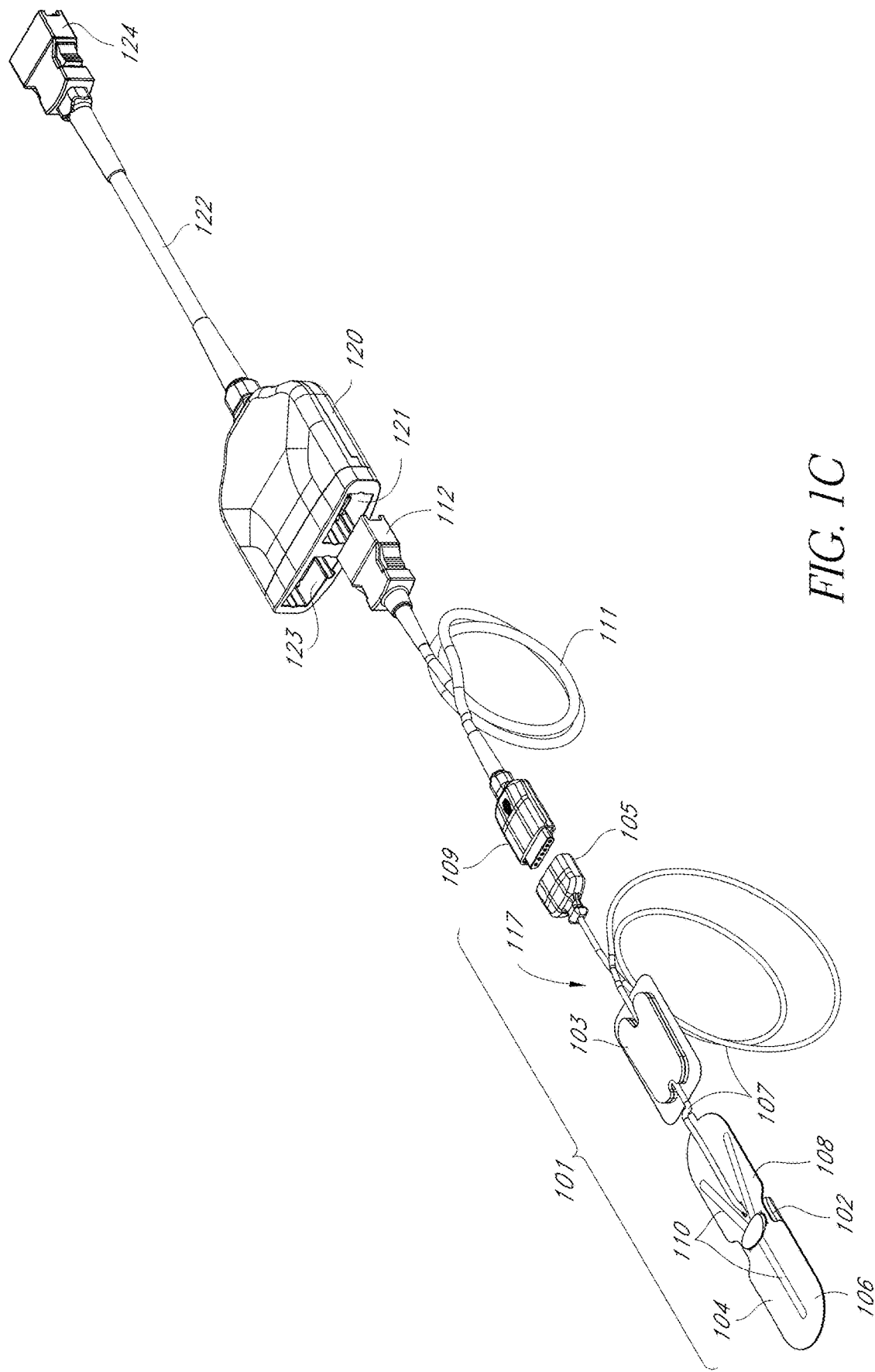
FIG. 1C illustrates an embodiment of a sensor system including a sensor assembly and a monitor cable suitable for use with any of the physiological monitors shown in FIGS. 1A-B.

Referring to the drawings, FIGS. 1A through 1C illustrate an overview of example patient monitoring systems, sensors, and cables that can be used to derive a respiratory rate measurement from a patient. FIGS. 2 through 16 illustrate more detailed embodiments for deriving respiratory rate measurements. The embodiments of FIGS. 2 through 16 can be implemented at least in part using the systems and sensors described in FIGS. 1A through 1C.

System Overview

Turning to FIG. 1A, an embodiment of a physiological monitoring system 10 is shown. In the physiological monitoring system 10, a medical patient 12 is monitored using one or more sensor assemblies 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, pulse oximetry sensors, or the like. The sensors 13 can generate respective signals by measuring a physiological parameter of the patient 12. The signals are then processed by one or more processors 19.

The one or more processors 19 can communicate the processed signal to the display 11. In an embodiment, the display 11 is incorporated in the physiological monitor 17. In another embodiment, the display 11 is separate from the physiological monitor 17. In one embodiment, the monitoring system 10 is a portable monitoring system. In another embodiment, the monitoring system 10 is a pod, without a display, that is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor assembly 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors 13, one or possibly more cables 13 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor assembly 13 and the physiological monitor 17 communicate wirelessly.

FIG. 1C illustrates an embodiment of a sensor system 100 including a sensor assembly 101 and a monitor cable 111 suitable for use with any of the physiological monitors shown in FIGS. 1A and 1B. The sensor assembly 101 includes a sensor 115, a cable assembly 117, and a connector 105. The sensor 115, in one embodiment, includes a sensor subassembly 102 and an attachment subassembly 104. The cable assembly 117 of one embodiment includes a sensor cable 107 and a patient anchor 103. A sensor connector subassembly 105 is connected to the sensor cable 107.

The sensor connector subassembly 105 can be removably attached to an instrument cable 111 via an instrument cable connector 109. The instrument cable 111 can be attached to a cable hub 120, which includes a port 121 for receiving a connector 112 of the instrument cable 111 and a second port 123 for receiving another cable. In certain embodiments, the second port 123 can receive a cable connected to a pulse oximetry or other sensor. In addition, the cable hub 120 could include additional ports in other embodiments for receiving additional cables. The hub includes a cable 122 which terminates in a connector 124 adapted to connect to a physiological monitor (not shown).

The sensor connector subassembly 105 and connector 109 can be configured to allow the sensor connector 105 to be straightforwardly and efficiently joined with and detached from the connector 109. Embodiments of connectors having connection mechanisms that can be used for the connectors 105, 109 are described in U.S. patent application Ser. No. 12/248,856 (hereinafter referred to as "the '856 Application"), filed on Oct. 9, 2008, which is incorporated in its entirety by reference herein. For example, the sensor connector 105 could include a mating feature (not shown) which mates with a corresponding feature (not shown) on the connector 109. The mating feature can include a protrusion which engages in a snap fit with a recess on the connector 109. In certain embodiments, the sensor connector 105 can be detached via one hand operation, for example. Examples of connection mechanisms can be found specifically in paragraphs [0042], [0050], [0051], [0061]-[0068] and [0079], and with respect to FIGS. 8A-F, 13A-E, 19A-F, 23A-D and 24A-C of the '856 Application, for example.

The sensor connector subassembly 105 and connector 109 can reduce the amount of unshielded area in and generally provide enhanced shielding of the electrical connection between the sensor and monitor in certain embodiments. Examples of such shielding mechanisms are disclosed in the '856 Application in paragraphs [0043]-[0053], [0060] and with respect to FIGS. 9A-C, 11A-E, 13A-E, 14A-B, 15A-C, and 16A-E, for example.

In an embodiment, the acoustic sensor assembly 101 includes a sensing element, such as, for example, a piezoelectric device or other acoustic sensing device. The sensing element can generate a voltage that is responsive to vibrations generated by the patient, and the sensor can include circuitry to transmit the voltage generated by the sensing element to a processor for processing. In an embodiment, the acoustic sensor assembly 101 includes circuitry for detecting and transmitting information related to biological sounds to a physiological monitor. These biological sounds can include heart, breathing, and/or digestive system sounds, in addition to many other physiological phenomena.

The acoustic sensor 115 in certain embodiments is a biological sound sensor, such as the sensors described herein. In some embodiments, the biological sound sensor is one of the sensors such as those described in the '883 Application. In other embodiments, the acoustic sensor 115 is a biological sound sensor such as those described in U.S. Pat. No. 6,661,161, which is incorporated by reference herein in its entirety. Other embodiments include other suitable acoustic sensors.

The attachment sub-assembly 104 includes first and second elongate portions 106, 108. The first and second elongate portions 106, 108 can include patient adhesive (e.g., in some embodiments, tape, glue, a suction device, etc.). The adhesive on the elongate portions 106, 108 can be used to secure the sensor subassembly 102 to a patient's skin. One or more elongate members 110 included in the first and/or second elongate portions 106, 108 can beneficially bias the sensor subassembly 102 in tension against the patient's skin and reduce stress on the connection between the patient adhesive and the skin. A removable backing can be provided with the patient adhesive to protect the adhesive surface prior to affixing to a patient's skin.

The sensor cable 107 can be electrically coupled to the sensor subassembly 102 via a printed circuit board ("PCB") (not shown) in the sensor subassembly 102. Through this contact, electrical signals are communicated from the multi-parameter sensor subassembly to the physiological monitor through the sensor cable 107 and the cable 111.

In various embodiments, not all of the components illustrated in FIG. 1C are included in the sensor system 100. For example, in various embodiments, one or more of the patient anchor 103 and the attachment subassembly 104 are not included. In one embodiment, for example, a bandage or tape is used instead of the attachment subassembly 104 to attach the sensor subassembly 102 to the measurement site. Moreover, such bandages or tapes can be a variety of different shapes including generally elongate, circular and oval, for example. In addition, the cable hub 120 need not be included in certain embodiments. For example, multiple cables from different sensors could connect to a monitor directly without using the cable hub 120.

Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," (hereinafter referred to as "the '883 Application"), the disclosure of which is hereby incorporated by reference in its entirety. An example of an acoustic sensor that can be used with the embodiments described herein is disclosed in U.S. patent application Ser. No. 12/643,939, filed Dec. 21, 2009, titled "Acoustic Sensor Assembly," the disclosure of which is hereby incorporated by reference in its entirety.

Figure 2:
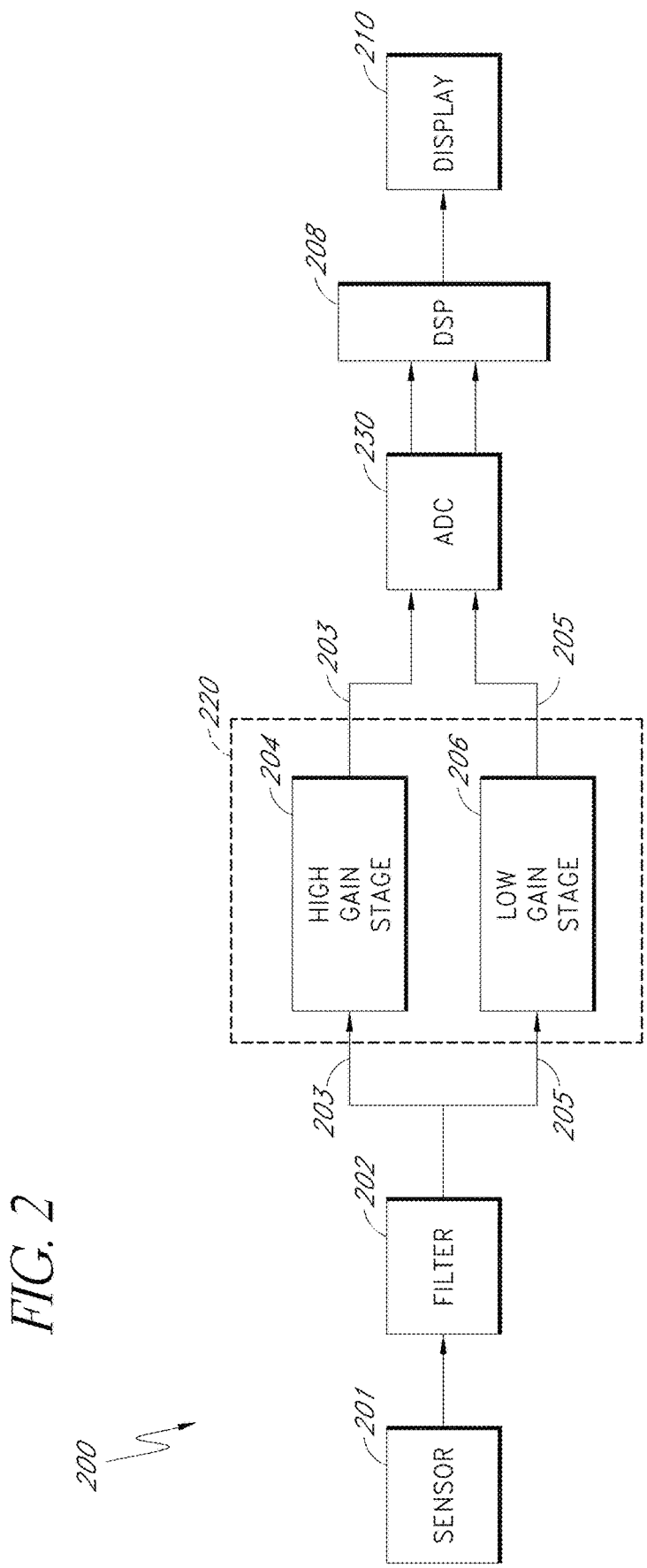
FIG. 2 is a top perspective view illustrating portions of a sensor system in accordance with an embodiment of the disclosure.

FIG. 2 depicts an embodiment of an acoustic signal processing system 200. The acoustic signal processing system 200 can be implemented by either of the physiological monitors described above. In the acoustic signal processing system 200, a sensor 201 transmits a physiological signal to a filter 202. In one embodiment, the filter 202 is a high pass filter. The high pass filter 202 can allow high frequency components of the voltage signal above a certain predetermined cutoff frequency to be transmitted and attenuates low frequency components below the cutoff frequency. Certain low frequency signals are desirable to attenuate in certain embodiments because such signals can saturate amplifiers in the gain bank 220.

Other types of filters may be included in the filter 202. For example, the filter 202 may include a low pass filter that attenuates high frequency signals. It may be desirable to reject high frequency signals because such signals often include noise. In certain embodiments, the filter 202 includes both a low pass filter and a high pass filter. Alternatively, the filter 202 may include a band-pass filter that simultaneously attenuates both low and high frequencies.

The output from the filter 202 is split in certain embodiments into two channels, for example, first and second channels 203, 205. In other embodiments, more than two channels are used. For example, in some embodiments three or more channels are used. The filter 202 provides an output on both first and second channels 203, 205 to a gain bank 220. The gain bank 220 can include one or more gain stages. In the depicted embodiment, there are two gain stages 204, 206. A high gain stage 204 amplifies the output signal from the filter 220 to a relatively higher level than the low gain stage 206. For example, the low gain stage 206 may not amplify the signal or can attenuate the signal.

The amplified signal at both first and second channels 203, 205 can be provided to an analog-to-digital converter (ADC) 230. The ADC 230 can have two input channels to receive the separate output of both the high gain stage 204 and the low gain stage 206. The ADC bank 230 can sample and convert analog voltage signals into digital signals. The digital signals can then be provided to the DSP 208 and thereafter to the display 210. In some embodiments, a separate sampling module samples the analog voltage signal and sends the sampled signal to the ADC 230 for conversion to digital form. In some embodiments, two (or more) ADCs 230 may be used in place of the single ADC 230 shown.

Acoustic Respiratory Monitoring System

Figure 3:
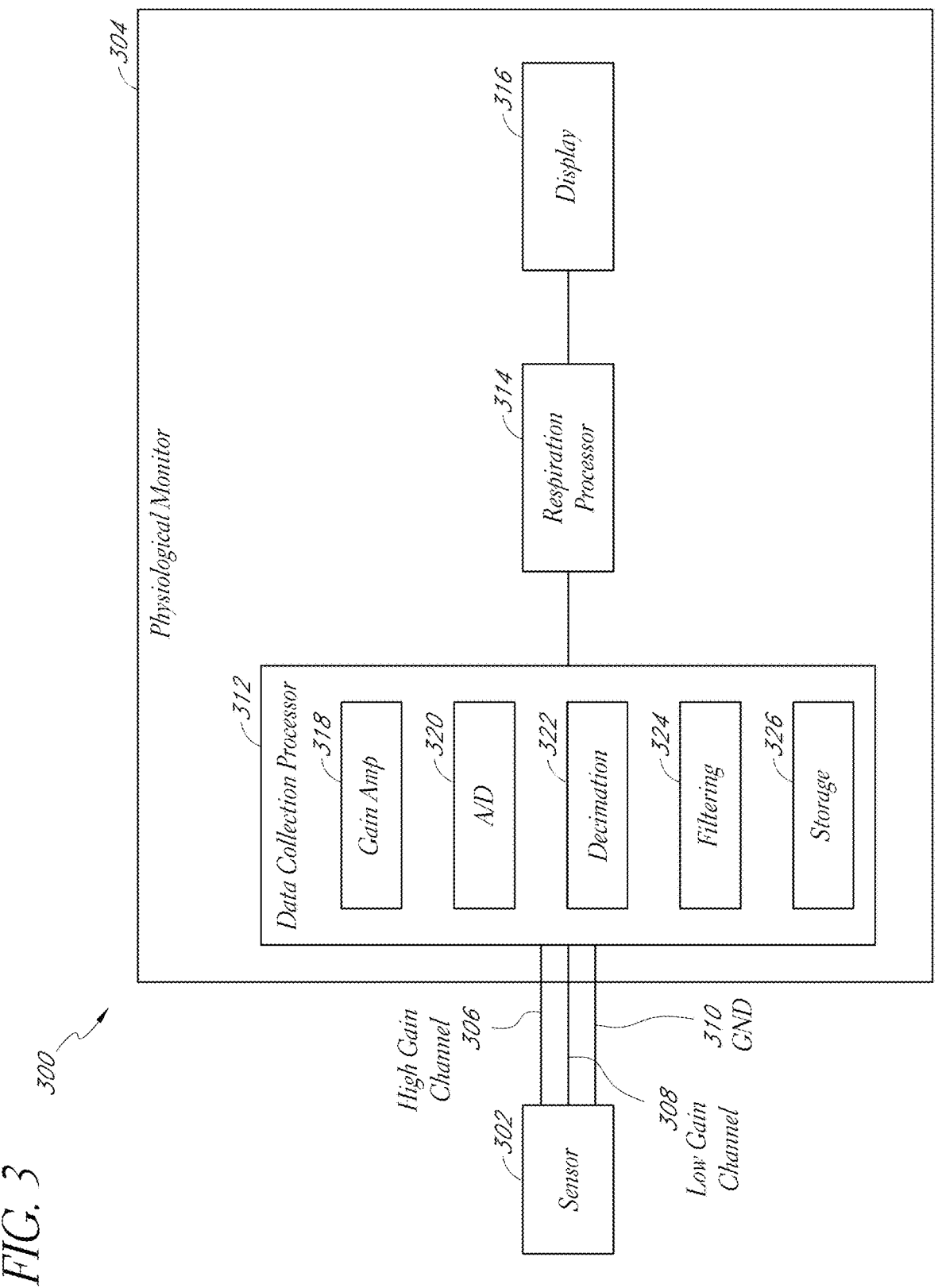
FIG. 3 illustrates one embodiment of an acoustic respiratory monitoring system.

FIG. 3 illustrates one embodiment of an acoustic respiratory monitoring system 300 compatible with the sensors, systems, and methods described herein. The acoustic respiratory monitoring system 300 includes an acoustic sensor 302 that communicates with a physiological monitor 304. The sensor 302 provides a sensor signal to the physiological monitor 304. In one embodiment, the sensor signal is provided over three signal lines, which include a high gain channel 306, a low gain channel 308, and a ground line 310. The physiological monitor 304 includes a data collection processor 312, respiration processor 314, and an optional display 316. The high and low gain channels 306, 308 can include any of the functionality of the high and low gain channels described above.

The acoustic sensor 302 is configured to detect sounds emanating from within a medical patient. For example, the acoustic sensor 302 is often configured to detect the sound of a medical patient's respiration (including inhalation and exhalation), as well as other biological sounds (e.g., swallowing, speaking, coughing, choking, sighing, throat clearing, snoring, wheezing, chewing, humming, etc.). The acoustic sensor 302 can include any of the sensors described herein.

The acoustic sensor 302 may include pre-amplification circuitry (not shown) to generate an output signal, or signals, in response to detected sounds. In some cases, high amplitude (e.g., loud) detected sounds can cause the sensor to saturate. For example, the high amplitude input signal could cause a pre-amplifier having a predetermined, fixed gain setting to saturate. In such cases, meaningful acoustic information detected by the sensor 302 simultaneously with the high amplitude sounds could be lost. To avoid losing such information, the acoustic sensor 302 can include a second pre-amplifier that has a lower, predetermined, fixed gain setting. The sensor 302 provides both high and low gain outputs over separate channels 306, 308 to the physiological monitor. As will be discussed later, the physiological monitor 304 can be configured to switch its input stream between the high and low gain channels 306, 308 depending upon whether a sensor saturation event has occurred, or appears likely to occur.

The data collection processor 312 pre-processes the signals received from the sensor 302 in preparation for further analysis. In one embodiment, the data collection processor 312 includes one or more of a gain amplifier 318, an analog-to-digital converter 320, a decimation module 322, a filtering module 324, and a storage module 326.

A gain amplifier 318 is configured to increase or decrease the gain on the incoming data signal. An analog-to-digital converter 320 is configured to convert the incoming analog data signal into a digital signal. A decimation module 322 is configured to reduce the quantity of data associated with the digitized analog input signal.

For example, the sensor 302 can provide a continuous analog signal to the analog-to-digital converter 320. The analog-to-digital converter 320 outputs a digital data stream having a relatively high data rate. For example, in one embodiment, the analog-to-digital converter 320 provides a digital signal at 48 kHz. The decimation module 322 receives the high data rate data, and can reduce the data rate to a lower level. For example, in one embodiment the decimation module 322 reduces the data rate to 4 kHz or 2 kHz. Reducing the data rate advantageously reduces the processing power of the physiological monitor, in certain embodiments, as the high bandwidth data from the analog-to-digital converter 320 may not be necessary or useful for further respiratory processing. The decimation module 322 can also reduce and/or eliminate unwanted noise from the digitized respiratory signal. A filtering module 324 provides further signal filtering and/or cleaning, and a storage module 326 stores the filtered, digitized input respiration signal for further processing.

A respiration processor 314 analyzes the digitized input respiration signal to determine various physiological parameters and/or conditions. For example, the respiration processor 314 is configured to determine one or more of the respiration rate of the patient, inspiration time, expiration time, apnea events, breathing obstructions, choking, talking, coughing, etc. The respiration processor 314 is further configured to determine a confidence value, or quality value, associated with each physiological parameter or condition calculation. For example, for each sample of time for which the respiration processor 314 calculates a patient's respiration rate, the respiration processor 314 will also determine a confidence value (or quality value) associated with such calculation. Both the calculated physiological parameter value and the confidence associated with such calculation are displayed on a display 316.

Displaying both calculated parameters and confidence values advantageously helps a clinician to exercise her own clinical judgment in evaluating the patient's physiological condition. For example, instead of merely showing "error" or "no available signal" during physiological events that affect respiration detection, the physiological monitor 304 can provide the clinician with its best estimation of the physiological parameter while indicating that some other event has occurred that impacts the monitor's 304 confidence in its own calculations.

In addition, as data passes through the monitor 304, the monitor's various processing modules can appropriately process the data based upon the confidence level associated with each data point. For example, if data is identified as having a low confidence value, the monitor 304 can cause that data to have less or no influence over a physiological parameter calculation.

Identifying data quality can also advantageously allow the monitor 304 to process a continuous stream of data. For example, instead of stopping and starting data flow, or skipping "bad data" samples, the monitor 304 can continuously maintain and process the input data stream. This feature can allow implementation of much more robust, efficient, and less complex processing systems. For example, a finite infinite response filter (FIR filter) (or other filter) can break down, and large data portions may be lost, if it is used to process discontinuous or otherwise erroneous data. Alternatively, providing a data confidence or quality flag allows a processor employing an FIR filter to take further action avoid such problems. For example, in one embodiment, a low confidence or quality flag can cause a processor to substitute a measured data point value with an interpolated value falling between the two closest high confidence data points surrounding the measured data point.

Respiration Processor

Figure 4:
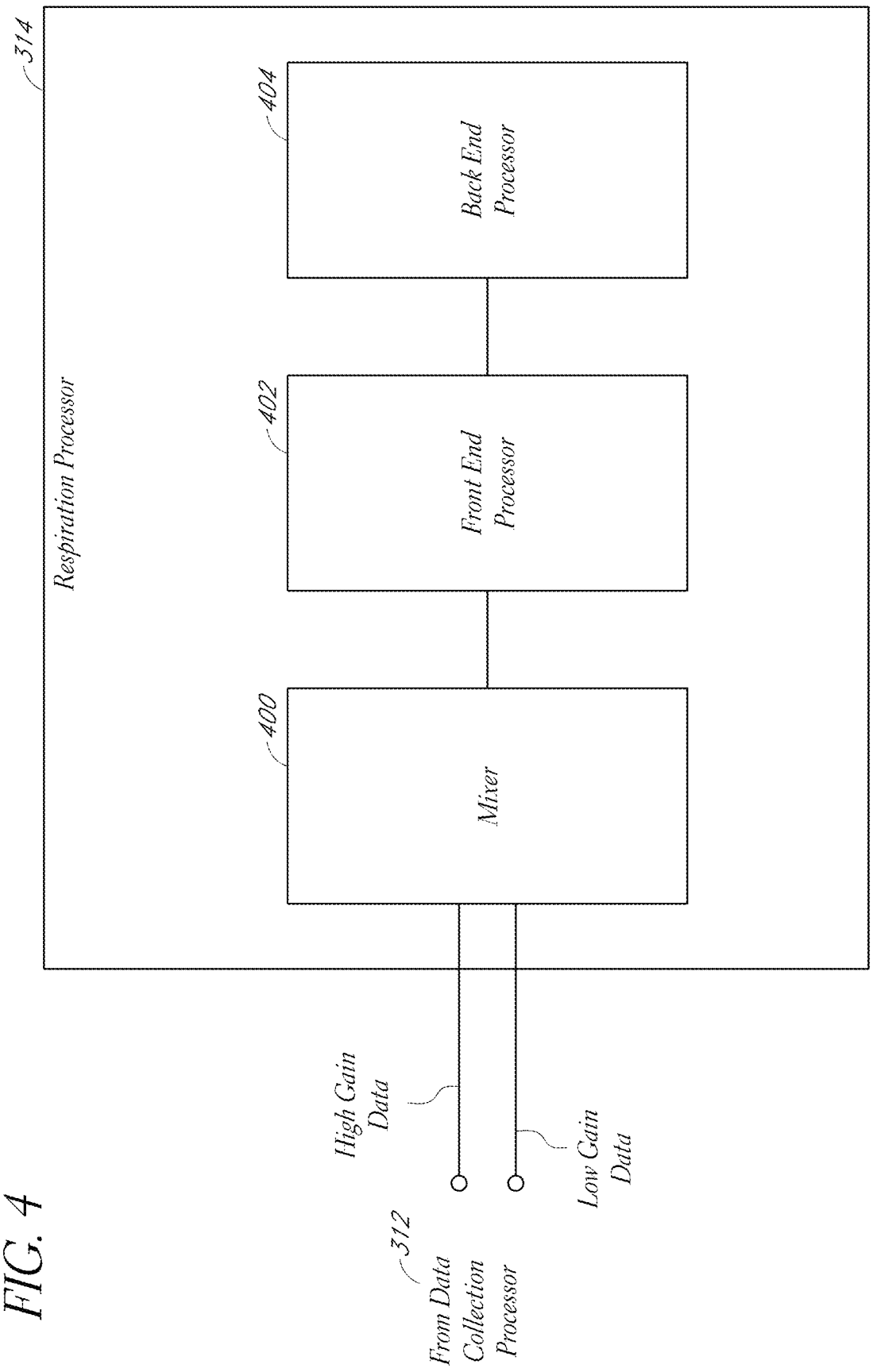
FIG. 4 illustrates one embodiment of the respiration processor of the acoustic respiratory monitoring system of FIG. 3.

FIG. 4 illustrates one embodiment of a respiration processor 314 compatible with any of the acoustic respiratory monitoring systems described herein. The respiration processor 314 includes a mixer 400, a front end processor 402, and a back end processor 404.

The mixer 400 obtains high and low gain data from the data collection processor 312. Because the high and low gain channels of the acoustic sensor 302 can have known, fixed values, the mixer 400 is able to determine when the high gain channel 306 will clip. If data obtained from the high gain channel 306 exceeds a clipping threshold, the mixer can change the data input stream from the high gain channel to the low gain channel 308. The mixer 400 effectively optimizes, in certain embodiments, the two incoming data signals to generate a working output signal for further processing. In certain embodiments, the mixer 400 generates an optimized working output signal having a desired dynamic range by avoiding use of clipped (e.g., pre-amplifier saturated) data points.

Although not shown, a compression module can also be provided as an output from the mixer. The compression module can compress, down sample, and/or decimate the working output signal to produce a reduced bit-rate acoustic signal. The compression module can provide this reduced bit-rate acoustic signal to a database for data storage or for later analysis. In addition, the compression module can transmit the reduced bit-rate acoustic signal over a network to a remote device, such as a computer, cell phone, PDA, or the like. Supplying a reduced bit-rate acoustic signal can enable real time streaming of the acoustic signal over the network.

Generating a Working Signal

Figure 5:
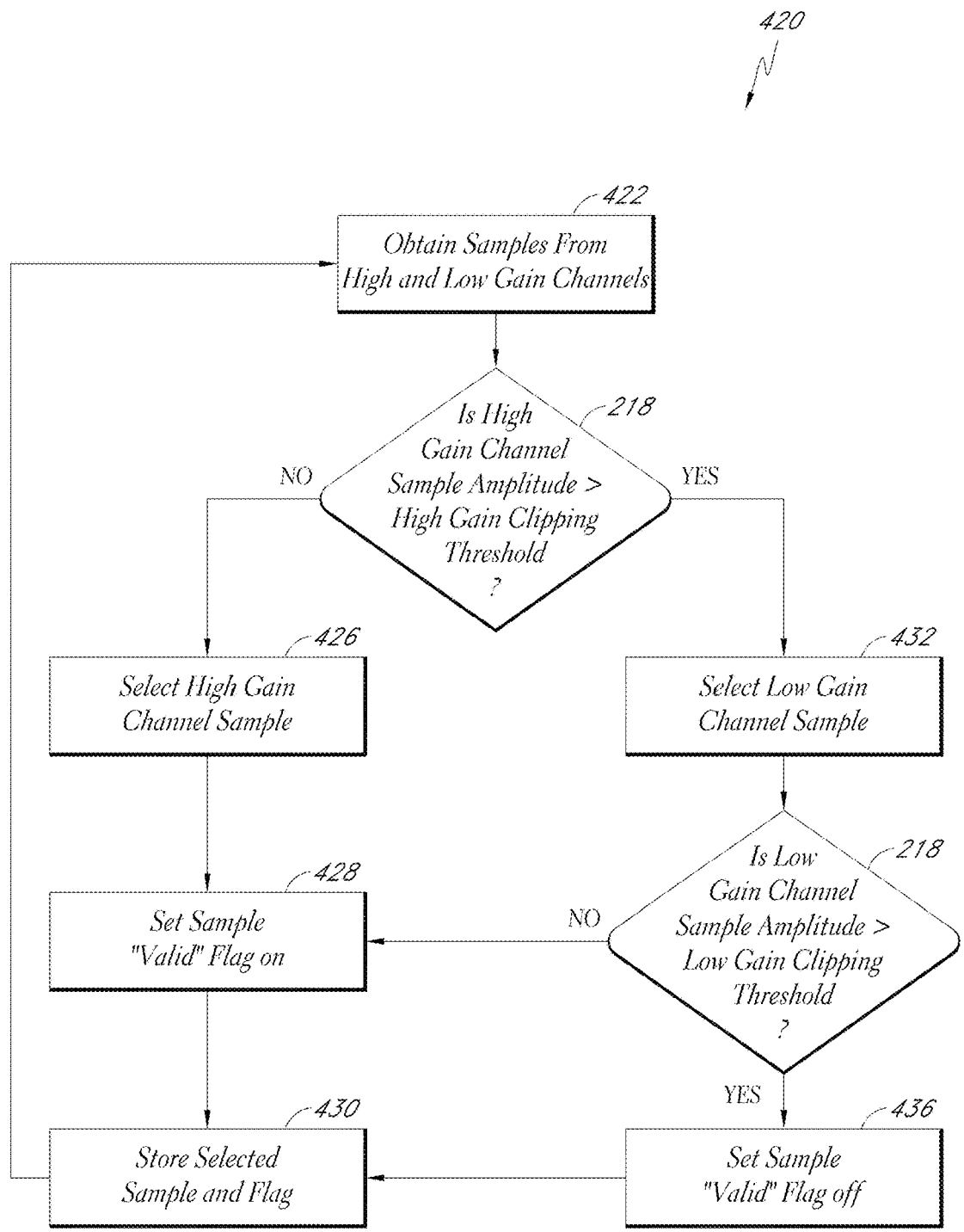
FIG. 5 illustrates one method of generating a working output signal, performed by the mixer of the respiration processor of FIG. 4.

One embodiment of a method 420 of generating a working output signal is illustrated in FIG. 5. The mixer 400 of FIG. 4 is configured to execute the illustrated method 420. At block 422, the method 420 obtains data samples from high and low gain data channels. At block 424, the method 420 determines whether the high gain channel sample's amplitude exceeds a high gain clipping threshold. If not, the method 420 proceeds to block 426.

At block 426, the method 420 selects the high gain channel sample. At block 428, the method 420 sets a "valid" flag to "on." The "valid" flag is one form of confidence or signal quality indicator, discussed above. Setting the "valid" flag to "on" indicates that the associated data sample may be a valid clinical data sample (for example, the measured value did not exceed a predetermined signal clipping threshold). The method 420 proceeds to block 430, where the method 420 stores both the selected sample and the flag values. The method 420 returns to block 422, where the next pair of samples is obtained from the high and low gain channels.

If at block 424 the method 420 determines that the high gain channel sample amplitude exceeds a high gain clipping threshold, the method 420 proceeds to block 432. At block 432, the method 420 selects the low gain channel sample. At block 434, the method 420 determines whether the low gain channel sample exceeds a low gain clipping threshold. If not, the method 420 proceeds to block 428, as described above.

If the method 420 determines that the low gain channel sample amplitude does exceed a low gain clipping threshold, the method proceeds to block 436. At block 436, the method 420 sets the "valid" flag "to "off." Setting the "valid" flag to "off" indicates that the data sample may not be a valid clinical data sample. The method 420 then proceeds to block 430, as described above. The stored values (referred to as the "working" and "valid" signals in FIGS. 6-8) are further processed by a front end processor of a respiration processor, for example, as described below.

Front End Processor

Figure 6:
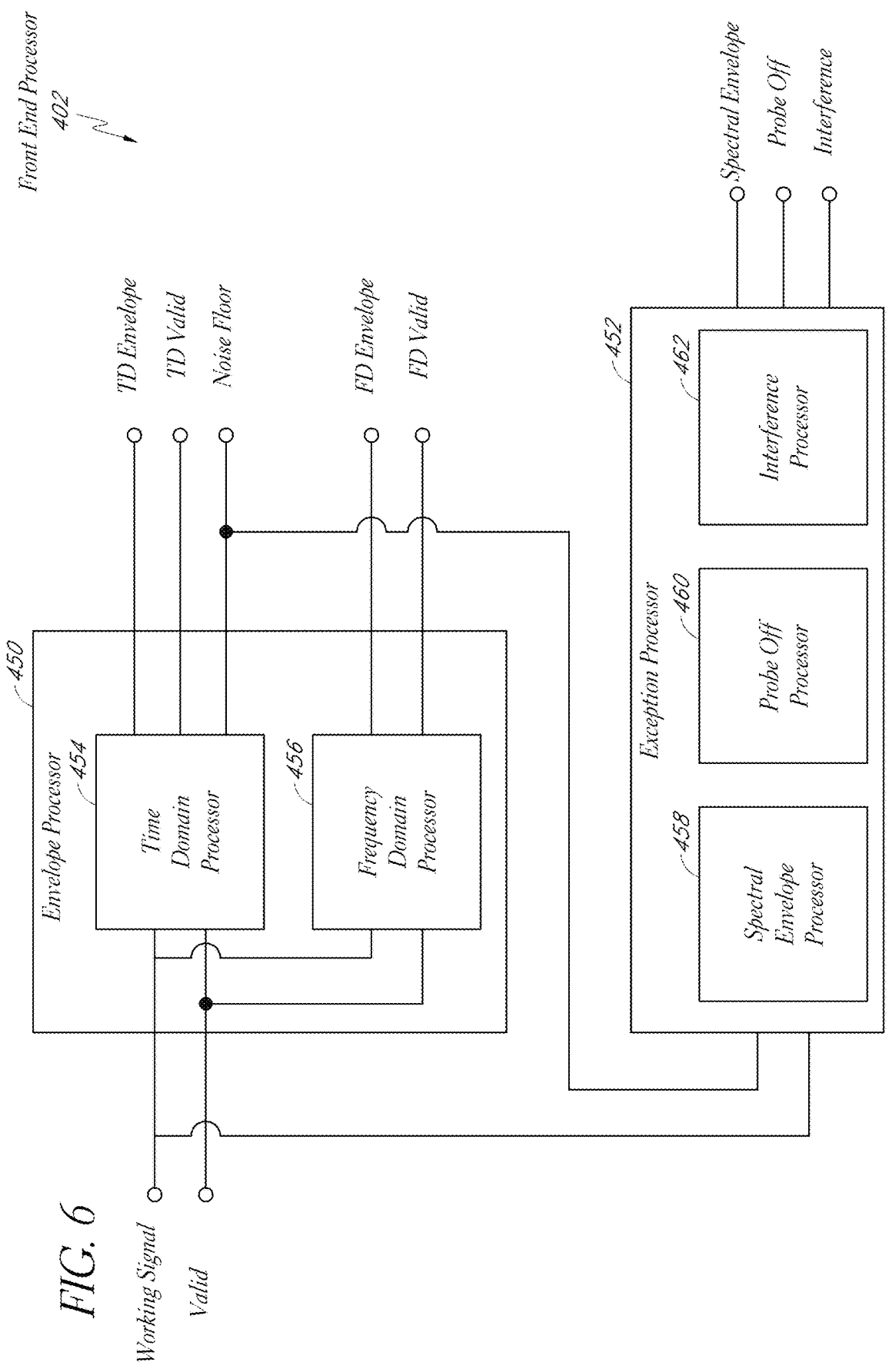
FIG. 6 illustrates one embodiment of the front end processor of the respiration processor of FIG. 4.

FIG. 6 illustrates one embodiment of the front end processor 402 of FIG. 4. The front end processor 402 includes an envelope processor 450 and an exceptions processor 452.

The envelope processor 450 includes a time domain processor 454 and a frequency domain processor 456. The exceptions processor includes a spectral envelope processor 458, a probe-off processor 460, and an interference processor 462.

The envelope processor 450 receives the working and valid signals from the mixer 400, discussed above. The envelope processor 450 processes these signals to generate a time domain envelope signal, a time domain valid signal, a noise floor, a frequency domain envelope signal, and a frequency domain valid signal. The exceptions processor 452 receives the working signal from the mixer 400 and the noise floor signal from the envelope processor 450 to generate a spectral envelope signal, a probe-off signal, and an interference signal. The time domain processor 454 and frequency domain processor 458 are described in further detail with respect to FIGS. 7 and 8, below.

By analyzing a working signal in both the time and frequency domains, in certain embodiments, the acoustic respiratory monitoring system 300 provides substantial, clinically significant advantages. To improve accuracy, the acoustic respiratory monitoring system 300 can seek to remove noise content from measured or sensed acoustic signals. However, noise can arise from multiple sources, and simple, single stage, or single engine processing techniques often provide inadequate results. For example, some noise occurs as a spike in signal amplitude. A slamming door, cough, or alarm could result in noise spike in an acoustic sensor's signal amplitude.

Other noise occurs in a more continuous nature. Such noise may not cause the sensor signal to spike in amplitude. For example, the low-frequency humming of a motor, light ballast, speech, or other vibration, could result in such continuous, relatively constant frequency noise signals. A time domain processor can be configured to effectively and efficiently remove amplitude-related noise content, while a frequency domain processor can be configured to effectively and efficiently remove frequency-related noise content. Employing both time and frequency processors can yield even further improved results.

In one embodiment, the spectral envelope processor 458 generates a spectrogram of the working signal. For example, each data point in the spectrogram signal can correspond to the highest frequency present in the working signal at that data point. Each data point in the working signal can correspond to the amplitude of the signal measured by the sensor 302 at a particular point in time. The spectral envelope provides the highest frequency present in the working signal at the same particular point in time.

The probe-off processor 460 determines whether the acoustic sensor 302 is properly attached to a measurement site on a patient. For example, if the working signal amplitude is below a certain threshold, the probe-off processor 460 determines that the acoustic sensor 302 is not properly attached to the patient's skin.

The interference processor 462 indicates whether an interference event has occurred. For example, the interference processor 462 indicates whether a noise event or disruption has been detected. Such events include can be identified, for example, when a loud instrument or device (e.g., a pump, generator, fan, ringing telephone, overhead page, television set, radio) has been turned-on or activated near the medical patient and/or whether the patient herself has generated an interfering, non-clinically relevant acoustical signal (e.g., sneezing, coughing, talking, humming, etc.).

Time Domain Processor

Figure 7:
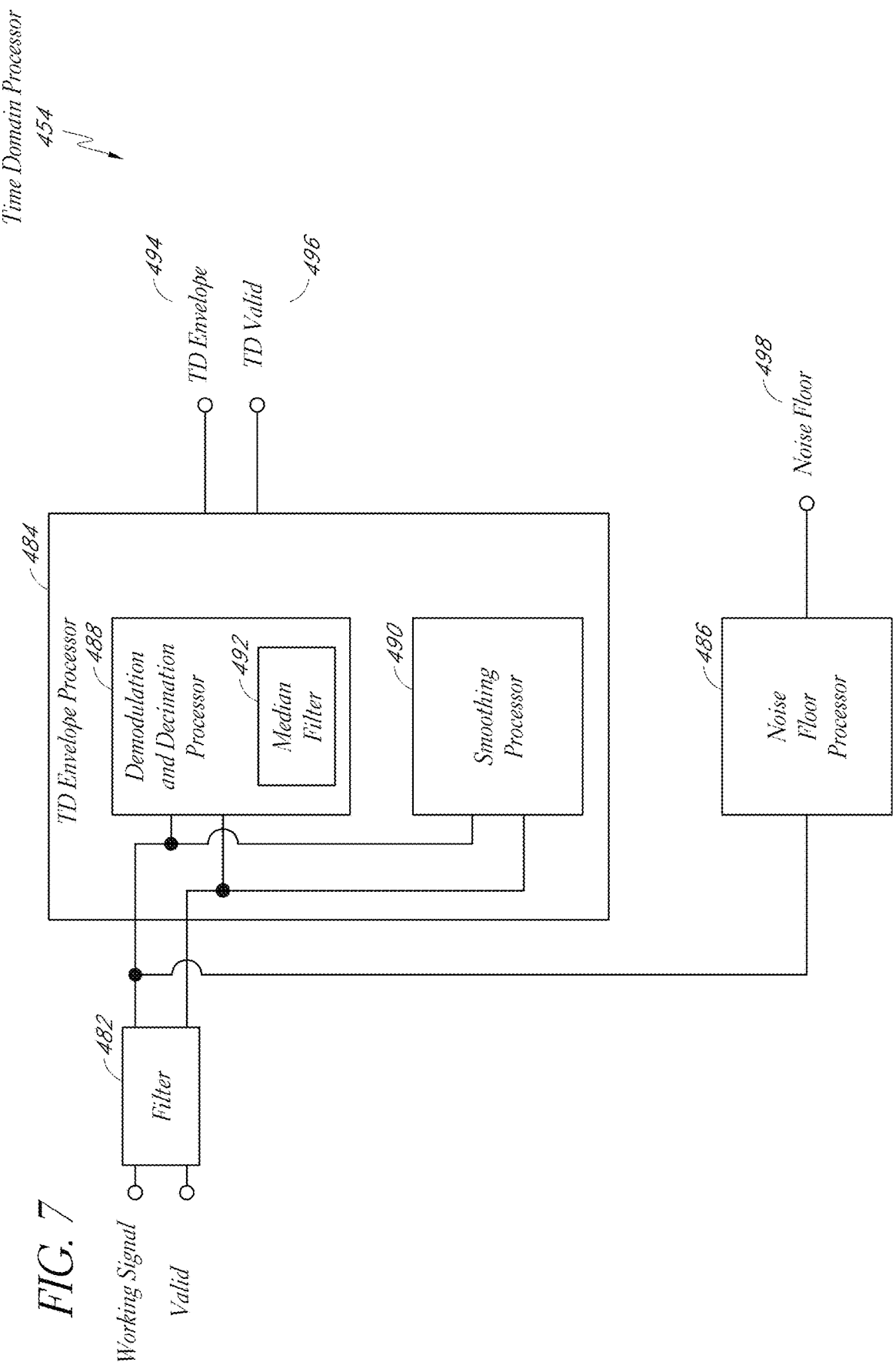
FIG. 7 illustrates one embodiment of a time domain processor of the front end processor of FIG. 6.

FIG. 7 illustrates one embodiment of a time domain processor 454 compatible with the front end processor 402, discussed above. The time domain processor 454 includes a filter 482, a time domain envelope processor 484, and a noise floor processor 486. The filter 482 receives working and valid signals from the mixer 400, as discussed above. The time domain envelope processor 484 receives filtered working and valid signals from the filter 482. The time domain envelope processor 484 generates a time domain envelope signal 494 and a time domain valid signal 496 based upon the filtered working and valid signals. The noise floor processor 486 provides a noise floor signal 498 in response to the filtered working signal received from the filter 482.

The time domain processor 454 includes one or more envelope generators. For example, the time domain processor 454 can include one or more of a demodulation and decimation processor 488, a smoothing processor 490, and/or any other envelope generator (e.g., a Hilbert transformation processor, a power method envelope processor, etc.). The envelope processor 484 can also include a median filter 492. In one embodiment, the demodulation and decimation processor 488 includes the median filter 492.

In one embodiment, the demodulation and decimation processor 488 squares the input data, multiplies it by a factor of two, sends it through a filter (such as a low pass filter, a finite impulse response (FIR) filter, or an infinite impulse response (IIR) filter), buffers the output, provides the buffered output to a median filter 492, and then takes the square root, to derive an envelope signal. The median filter 492 picks out only the middle value of sorted, buffered data. For example, the median filter 492 first sorts the data and then selects the middle value. In one embodiment, the demodulation and decimation processor 488 buffers seven data points (or some other number of points) that are output from an FIR filter (as discussed above). The median filter 492 sorts the data (either high to low, or low to high), and then selects the value of the fourth data point (e.g., the middle of the seven data points) as its output value.

As subsequent data is analyzed by the demodulation and decimation processor 488, the buffered data is shifted by one sample, and the median filter 492 again selects the middle value of the sorted, buffered data. The median filter 492 is sometimes referred to as a running median filter.

The smoothing processor 490 employs another technique to derive a time domain envelope signal. For example, in one embodiment, the smoothing processor 490 processes buffered input data by determining a standard deviation, multiplying the output by three, squaring the output, and then sending the squared output to a filter, such as a low pass filter, FIR filter, or IIR filter.

The noise floor processor 486 determines the noise floor of its input signal. For example, the noise floor processor 486 can be configured to select a value below which or above which the input signal will be considered to be merely noise, or to have a substantial noise content.

Frequency Domain Processor

Figure 8:
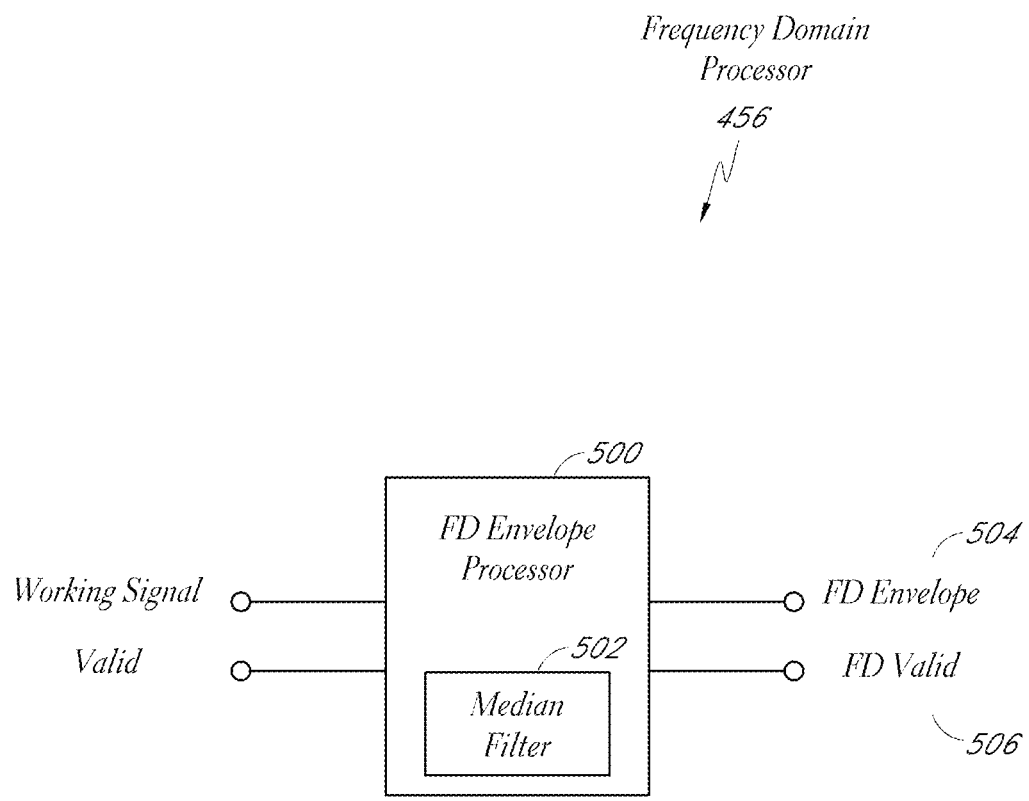
FIG. 8 illustrates one embodiment of a frequency domain processor of the front end processor of FIG. 6.

FIG. 8 illustrates one embodiment of a frequency domain processor 456 compatible with the front end processor 402, discussed above. The frequency domain processor includes a frequency domain envelope processor 500, which includes a median filter 502. The frequency domain processor 456 receives working and valid signals from the mixer 400, as described above, and generates a frequency domain envelope and frequency domain valid signals based on the working and valid signals.

In one embodiment, the frequency domain envelope processor 500 transforms the working signal into the frequency domain by utilizing a Fourier transform (e.g., fast Fourier transform (FFT), discrete Fourier transform (DFT), etc.). The frequency domain processor 456 can then identify an envelope of the output of the Fourier transform. For example, the frequency domain processor 456 can square an absolute value of the Fourier transform output. In some embodiments, the frequency domain processor 456 further processes the output with sub matrix, mean, log, and gain operations. Additionally, in some embodiments, the output is buffered and provided to a median filter 502, which can operate under the same principles as the median filter 492 described above with respect to FIG. 7. The output of the median filter 502 can be provided as a frequency domain envelope signal 504.

Although not shown, in certain embodiments, the frequency domain processor 456 can also calculate spectral information, such as a power spectrum, spectral density, power spectral density, or the like. In one embodiment, the spectral information X can be calculated as follows:

$$X = 20 \log(\text{FFT}(x)) \tag{1}$$

where x in equation (1) represents the working signal input to the envelope processor 450 (or a processed form of the working signal). The spectral information can be calculated for each block or frame of samples received by the envelope processor 450. The spectral information can be calculated using other techniques than those described herein. For example, the log(FFT(x)) may be multiplied by 10 instead of 20, or the power spectral density may be calculated from the Fourier transform of the autocorrelation of the input signal, or the like.

The spectral information from multiple blocks or frames of samples can be combined to form a representation of changes in the spectral information over time. If this combined spectral information were output on a display, the combined spectral information could be considered a spectrogram, a waterfall diagram, or the like. An example of such a spectrogram is described below with respect to FIG. 13B.

Back End Processor

Figure 9:
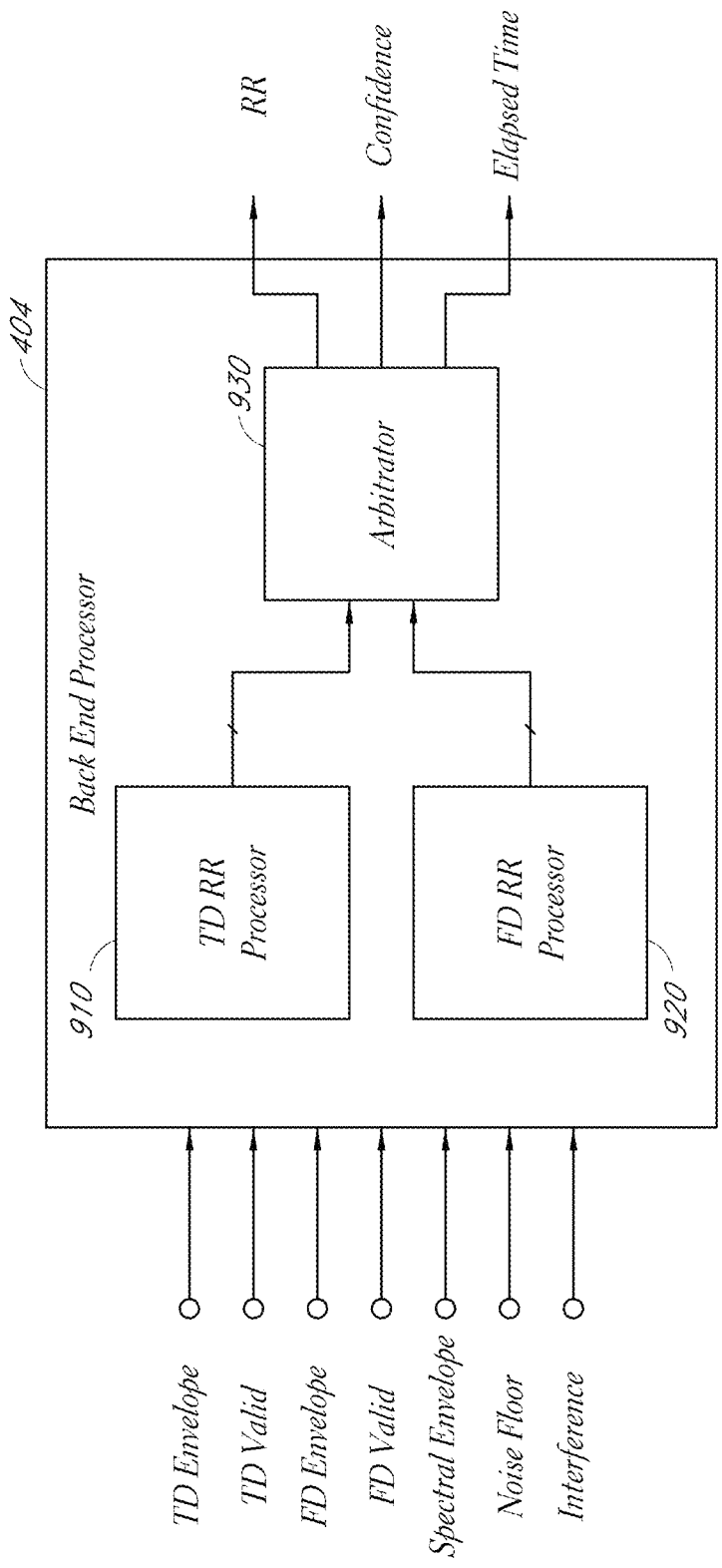
FIG. 9 illustrates an embodiment of a back end processor.

FIG. 9 illustrates a more detailed embodiment of the back end processor 404 described above with respect to FIG. 4. The back end processor 404 can be implemented in hardware and/or software. Advantageously, in certain embodiments, the back end processor 404 calculates respiratory rate in the time domain and in the frequency domain. The back end processor 404 can use various arbitration techniques to select and/or to combine the respiratory rate values obtained from the time and frequency domains.

In the depicted embodiment, the back end processor 404 receives a time domain (TD) envelope, a time domain (TD) valid signal, a frequency domain (FD) envelope, a frequency domain (FD) valid signal, a spectral envelope, noise floor information, and interference information. These inputs can be generated using any of the systems and processes described above. Not all of these inputs need be used or received by the back end processor 404 in certain implementations.

The back end processor 404 includes a time domain respiratory rate (TD RR) processor 910, the frequency domain respiratory rate (FD RR) processor 920, and an arbitrator 930. The TD RR processor 910 can use time domain techniques to derive respiratory rate values from various ones of the inputs received by the back end processor 404. The TD RR processor 910 can also calculate confidence values reflecting confidence in the calculated respiratory rate values. The FD RR processor 920 can use frequency domain techniques to derive respiratory rate values from various ones of the inputs received by the back end processor 404. The FD RR processor 920 can also calculate confidence values reflecting confidence in the calculated respiratory rate values. In some embodiments, only time domain techniques or only frequency domain techniques are used by the back end processor 404 to calculate respiratory rate.

The TD RR processor 910 and the FD RR processor 920 can provide respiratory rate outputs and confidence values to the arbitrator 930. In certain embodiments, the arbitrator 930 can evaluate the time domain and frequency domain respiratory rate calculations as well as the confidence values to select a respiratory rate value to output. Based on the confidence calculations, the arbitrator 930 can output the respiratory rate values derived from the time domain or from the frequency domain. The arbitrator 930 can also combine the respiratory rate values derived from the different domains, for example, by averaging the values together.

For ease of illustration, this specification describes the respiration processor 314 as having time domain and frequency domain processors or engines. However, in other embodiments, the respiration processor 314 can include only a time domain engine, only a frequency domain engine, or additional engines in combination with either of the time domain and frequency domain engines or with both. The arbitrator 930 can calculate an overall respiratory rate based on the outputs of any of the engines, including a combination of the engines. The arbitrator 930 can weight, select, or otherwise choose outputs from the different engines. The weightings for each engine can be learned and adapted (e.g., using an adaptive algorithm) over time. Other configurations are possible.

One example of an additional engine that can calculate respiratory rate is a wavelet-based engine, which can be used to perform both time and frequency domain analysis. In one embodiment, the respiration processor 314 includes the wavelet analysis features described in U.S. application Ser. No. 11/547,570, filed Jun. 19, 2007, titled "Non-invasive Monitoring of Respiratory Rate, Heart Rate and Apnea," the disclosure of which is hereby incorporated by reference in its entirety.

Another example of an engine that can be used to calculate respiratory rate is an engine based on a Kalman filter. The Kalman filter can be used to predict a state of a system, such as the human body, based on state variables. The state of the human body system can depend on certain state parameters, such as hemodynamic parameters (e.g., heart rate, oxygen saturation, respiratory rate, blood pressure, and the like). A Kalman filter model can be developed that interrelates these parameters. As part of this model, one or more measurement equations can be established for measuring the various state parameters, including respiratory rate.

The arbitrator 930 can also calculate a freshness or relevance of the respiratory rate measurement. In some situations, the confidence output by the arbitrator 930 may be low, and the corresponding respiratory rate output value may be invalid or corrupted. One option when this happens is to discard the invalid or low quality respiratory rate value and not display a new respiratory rate measurement until a valid or higher quality value is obtained. However, not displaying a respiratory rate value (or showing zero) can confuse a clinician if the patient is still breathing. Likewise, cycling between zero and a valid respiratory rate value can be annoying or confusing for a clinician.

Thus, instead of displaying no (or zero) value in low quality signal conditions, the arbitrator 930 can continue to output the previous respiratory rate measurement for a certain amount of time. The arbitrator 930 can include a counter, timer, or the like that increments as soon as a low or invalid signal condition is detected. When the arbitrator 930 determines that a certain amount of time has elapsed, the arbitrator 930 can output a zero or no respiratory rate value. Conversely, if while the arbitrator 930 is incrementing the counter a valid or higher quality respiratory rate measurement is produced, the arbitrator 930 can reset the counter.

The amount of time elapsed before the arbitrator 930 outputs a zero or no respiratory rate value can be user-configurable. The arbitrator 930 can output the elapsed time that the respiratory rate measurement has had low or no confidence. The arbitrator 930 could also (or instead) output an indicator, such as a light, changing bar, number, an audible alarm, and/or the like that is output when the arbitrator 930 is incrementing the counter. The indicator can be deactivated once valid or higher confidence respiratory rate values are calculated.

Time Domain RR Calculation

Figure 10:
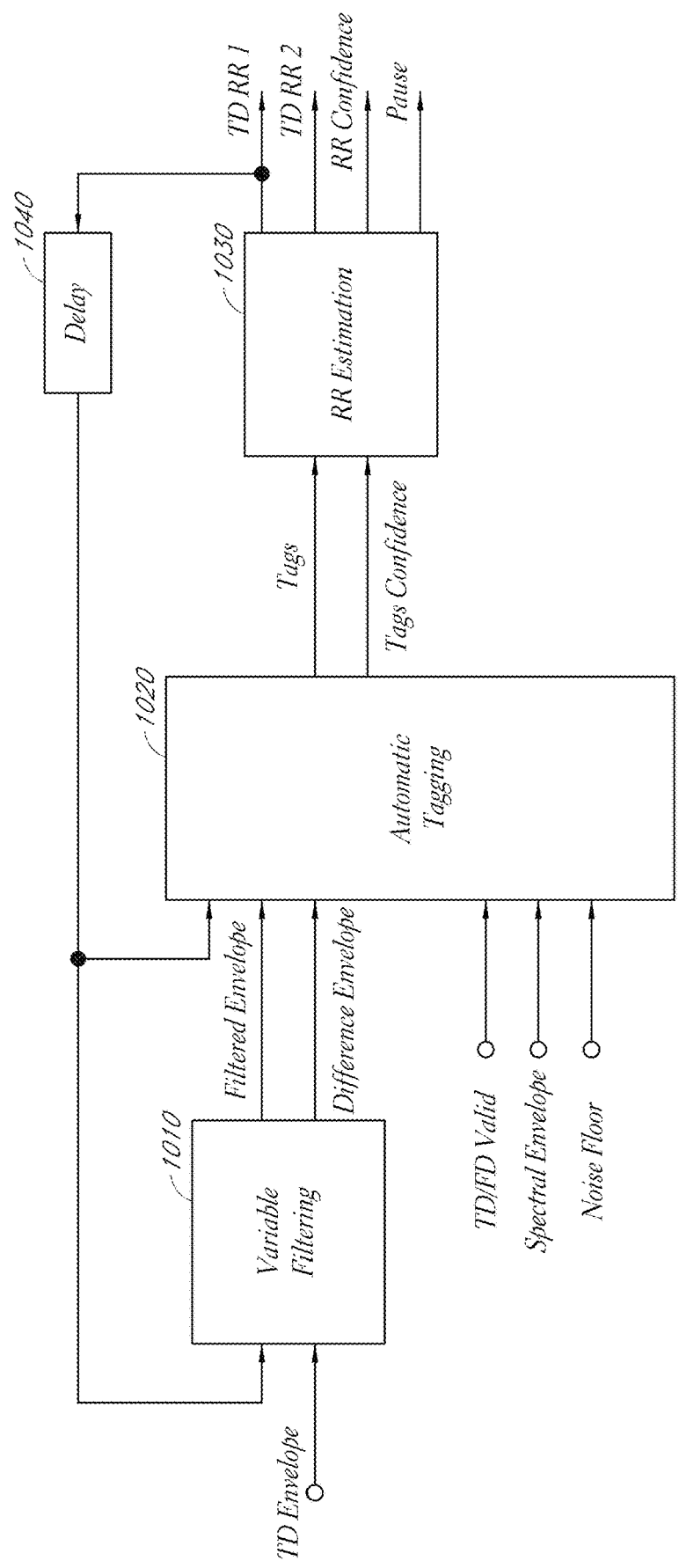
FIG. 10 illustrates an embodiment of a time domain respiratory rate processor.

FIG. 10 illustrates an embodiment of a time domain respiratory rate (TD RR) processor 1000. The TD RR processor 1000 is an example implementation of the TD RR processor 910 of FIG. 9.

By way of overview, the TD RR processor 1000 can determine respiratory rate by identifying energy in the time domain that has possible meaning. Meaningful energy can include peaks in the TD envelope that correspond to inspiration and/or expiration. The TD RR processor 1000 can disqualify energy that does not have meaning, including energy due to noise (e.g., coughing, sneezing, talking, chewing, ambient noise from the environment, etc.). From the energy that has meaning, the TD RR processor 1000 can calculate respiratory rate. Moreover, the TD RR processor 1000 can calculate one or more confidence values reflecting confidence in the calculated respiratory rate.

In the depicted embodiment, the TD RR processor 1000 includes a variable filtering module 1010, an automatic tagging module 1020, and an RR estimation module 1030. Each of these modules can be implemented in hardware and/or software. Each of these modules can operate on blocks or frames of samples in certain implementations (see, e.g., FIG. 16C).

The variable filtering module 1010 receives a TD envelope, such as the TD envelope described above. The variable filtering module 1010 can apply one or more filters to the TD envelope to smooth the TD envelope. The one or more filters can include a low pass filter. Smoothing the TD envelope can reduce noise in the TD envelope. In certain embodiments, the variable filtering module 1010 can change the cutoff frequency or frequencies of the one or more filters based at least in part on previously calculated RR values. Using a previously calculated respiratory rate value to determine a cut off frequency of a smoothing filter can reduce errors that can occur from over-smoothing or under-smoothing the TD envelope. Over smoothing can occur if the new respiratory rate value is relatively high for a given lower cutoff frequency, and under smoothing can occur if the new respiratory rate value is relatively low for a given higher cutoff frequency.

In the depicted embodiment, the variable filtering module 1010 receives a previous respiratory rate value (RR_old) from the RR estimation module 1030 via a delay block 1040. In one embodiment, if the previous respiratory rate value is above a certain threshold, the cutoff frequency for the smoothing filter is increased to a certain value. If the previous respiratory rate value is below a certain rate, then the cutoff frequency for the smoothing filter can be decreased to a certain value. The cut off frequency can also be adjusted on a sliding scale corresponding to the previous respiratory rate value. In one embodiment, the cut off frequency can range from about 1 Hz to about 3 Hz. This range can be varied considerably in certain embodiments.

The variable filtering module 1010 can also create a difference envelope by subtracting the TD envelope from the filtered envelope (or vice versa). The difference envelope can be used in glitch detection and reduction, as will be described in greater detail below. The variable filtering module 1010 can provide the filtered and difference envelopes to the automatic tagging module 1020.

In certain embodiments, the automatic tagging module 1020 identifies peaks in the filtered TD envelope that correspond to inspiration and/or expiration. Each peak can be referred to as a tag. The automatic tagging module 1020 can determine confidence and the identified tags based at least in part on a received TD and/or FD valid signal, a spectral envelope signal, and/or a noise floor signal. These signals and values are described in part above with respect to FIGS. 3 through 8.

The automatic tagging module 1020 can output the tags and confidence values corresponding to the tags to the RR estimation module 1030. The RR estimation module 1030 can estimate respiratory rate from the identified tags. For example, the RR estimation module 1030 can calculate time periods between pairs of tags within a given processing frame to derive a respiratory rate value for each pair of tags. In one embodiment, the RR estimation module 1030 calculates respiratory rate for every first and third peak so as to calculate respiration from inspiration to inspiration peak and/or from expiration to expiration peak. The respiratory rate value can be derived by multiplying the reciprocal of the time period between two peaks by 60 (seconds per minute) to achieve breaths per minute. The RR estimation module 1030 can average the respiratory rate values from the various tag pairs within the processing frame. This average can be a weighted average (see FIGS. 11B through 11D). The RR estimation module 1030 can also calculate a confidence value for the processing frame based at least in part on the received tags confidence value for each tag or pair of tags.

Figure 11A:
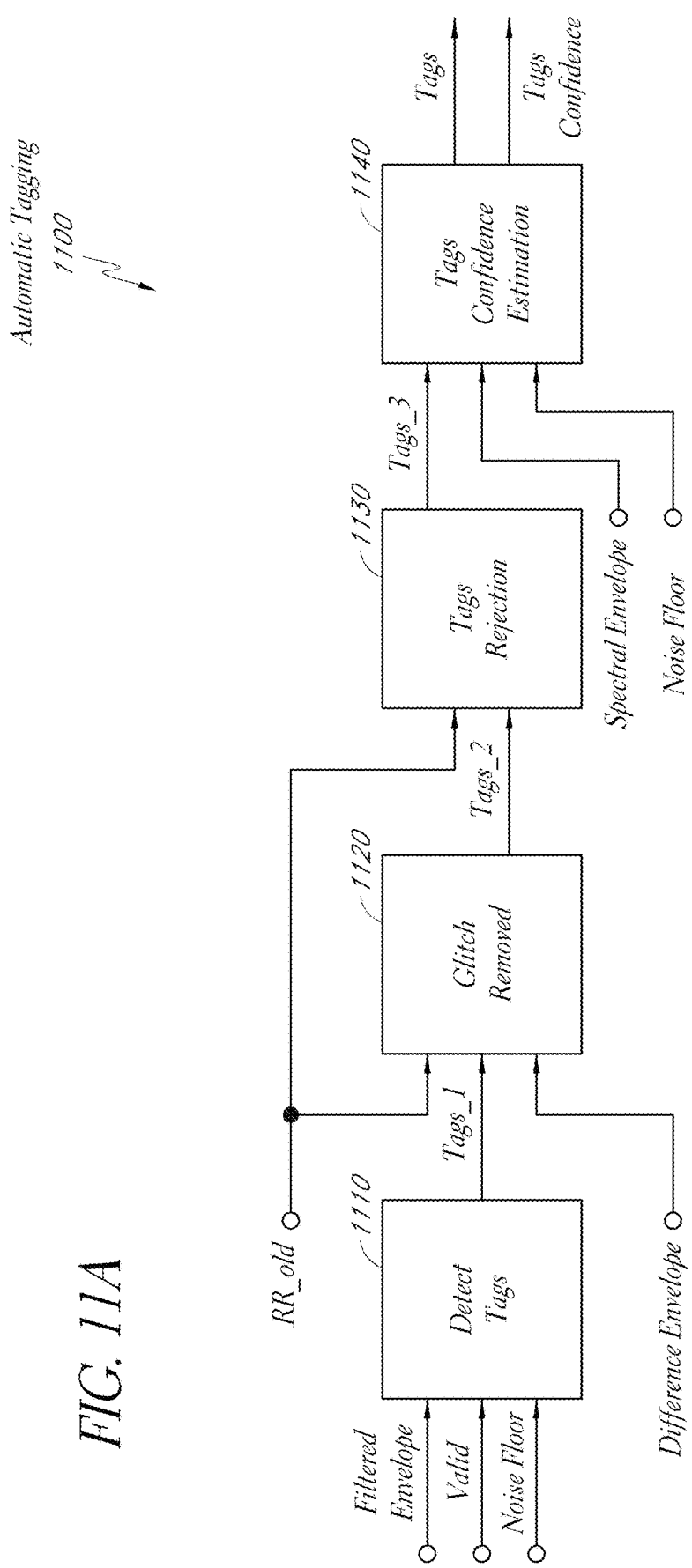
FIG. 11A illustrates an embodiment of an automatic tagging module of the time domain respiratory rate processor of FIG. 10.

FIG. 11A illustrates a more detailed embodiment of an automatic tagging module 1100. The automatic tagging module 1100 is an example implementation of the automatic tagging module 1020 of the TD RR processor 1000. As described above, the automatic tagging module 1100 can be used to identify peaks of energy in the filtered TD envelope.

The automatic tagging module 1100 includes a tag detection module 1110, a glitch removal module 1120, a tags rejection module 1130, and a tags confidence estimation module 1140. Each of these modules can be implemented in hardware and/or software. Each of these modules operate on blocks or frames of samples in certain implementations.

The tag detection module 1110 receives the filtered (TD) envelope, a valid signal, and the noise floor signal. The tag detection module 1110 can make a preliminary detection of peaks and/or valleys in the filtered envelope. The tag detection module 1110 can use the noise floor signal to determine which peaks are above the noise floor. The tag detection module 1110 can include an adaptive threshold, for instance, for estimating which peaks should be considered tags based at least in part on the noise floor level. Thus, peaks occurring below the noise floor may not be considered to be tags that represent inspiration or expiration. In addition, the tag detection module 1110 can have an upper threshold based at least in part on a root mean square (RMS) value of the filtered envelope. Peaks above the upper threshold may not be considered to be tags because they may be due to noise such as talking or the like.

The tag detection module 1110 can output preliminary tags (referred to as tags_1 in the FIGURE) to the glitch removal module 1120. The glitch removal module 1120 can compare the identified tags with the difference envelope described above with respect to FIG. 10. This comparison can yield an identification of spikes or other peaks in the identified tags that can correspond to noise or other glitches. The glitch removal module 1120 can filter out, remove, or reduce the amplitude of tags that correspond to glitches or noise. The glitch removal module 1120 therefore outputs new tags (referred to as tags_2 in the FIGURE) with the glitches removed or reduced.

The glitch removal module 1120 can provide the tags to the tags rejection module 1130. The tags rejection module 1130 can use any of a variety of techniques to remove tags that possibly do not correspond to inspiration or expiration sounds of a patient. For instance, the tags rejection module 1130 could reject a tag if it is too close to another tag. Tags that are too close together could result in a respiratory rate that is too high and therefore not physiologically possible. In certain embodiments, the smaller of the two peaks is rejected, although this may not always be the case. The closeness constraint could be relaxed or not used entirely for certain patients, such as neonates, who may have a higher respiratory rate.

Another technique that could be used by the tags rejection module 1130 is to find peaks that are related. Peaks that are related can include peaks that do not have a clear separation from one another. For example, a valley separating two peaks could be relatively shallow compared to valleys surrounding the peaks. In certain embodiments, if the valley between the peaks falls below half the amplitude of one or both of the peaks, the peaks could be considered to be separate peaks or tags. Otherwise, the peaks could be considered to be one tag (e.g., corresponding to two intakes or exhales of air in rapid succession).

The tags rejection module 1130 could also analyze tags that appear at the beginning and/or end of a block of samples or frame. The tags rejection module 1130 could select to reject one of these first or last peaks based at least in part on how much of the peak is included in the frame. For instance, a peak that is sloping downward toward the beginning or end of the frame could be considered a tag for that frame; otherwise, the tag might be rejected.

Another technique that can be used by the tags rejection module 1130 is to identify and remove isolated peaks. Since breathing sounds tend to include an inspiration peak followed by an expiration peak, an isolated peak might not refer to a breathing sound. Therefore, the tags rejection module 1130 could remove any such peaks. The tags rejection module 1130 could also remove narrow peaks, which may not realistically correspond to a breathing sound.

Moreover, in certain embodiments, the tags rejection module 1130 can perform parametric rejection of peaks. The tags rejection module 1130 can, for example, determine statistical parameters related to the peaks within a block or frame, such as standard deviation, mean, variance, peaks duration, peak amplitude, and so forth. If the standard deviation or mean the value of the peak or peaks is much different from that of the previous block or frame, one or more of the peaks may be rejected from that block. Similarly, if the duration and/or amplitude of the peaks differ substantially from the duration and/or amplitude of peaks in a previous block or frame, those peaks might also be rejected.

The tags rejection module 1130 can provide the refined tags (referred to as tags_3 in the FIGURE) to the tags confidence estimation module 1140. The confidence estimation module 1140 can also receive the spectral envelope calculated above and the noise floor signal. The confidence estimation module 1140 can use a combination of the tags, the spectral envelope, and/or the noise floor to determine a confidence value or values in the tags. The confidence estimation module 1140 can output the tags and the confidence value.

In certain embodiments, the confidence estimation module 1140 can determine confidence in the tags received from the tags rejection module 1130. The confidence estimation module 1140 can use one or more different techniques to determine confidence in the tags. For instance, a confidence estimation module 1140 can analyze power or energy of the tags in the time domain. The confidence estimation module 1140 can also analyze the distribution of frequency components corresponding to the tags in the frequency domain. The confidence estimation module 1140 can use either of these two techniques or both together.

Figure 11B:
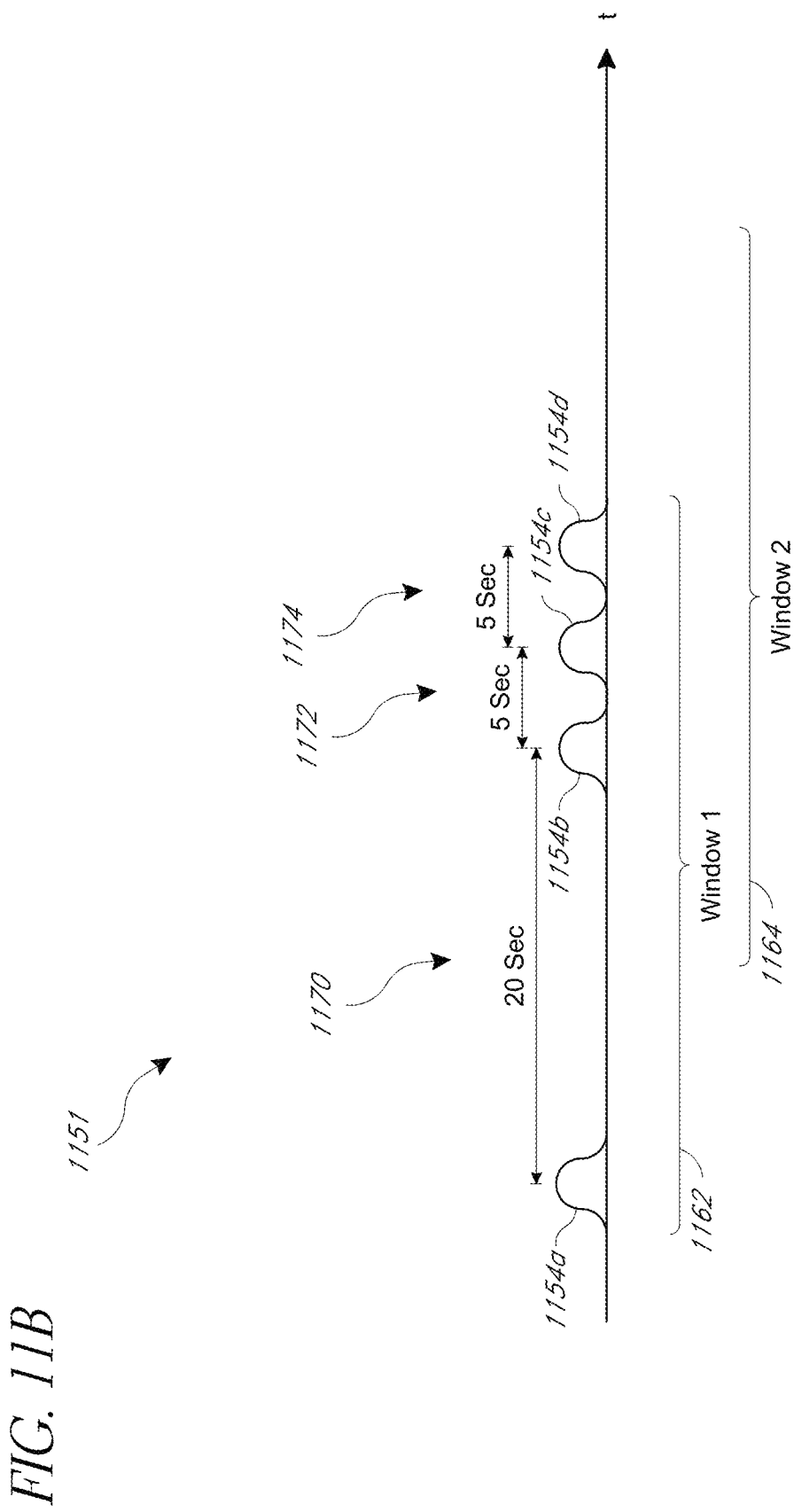
Figure 11D:
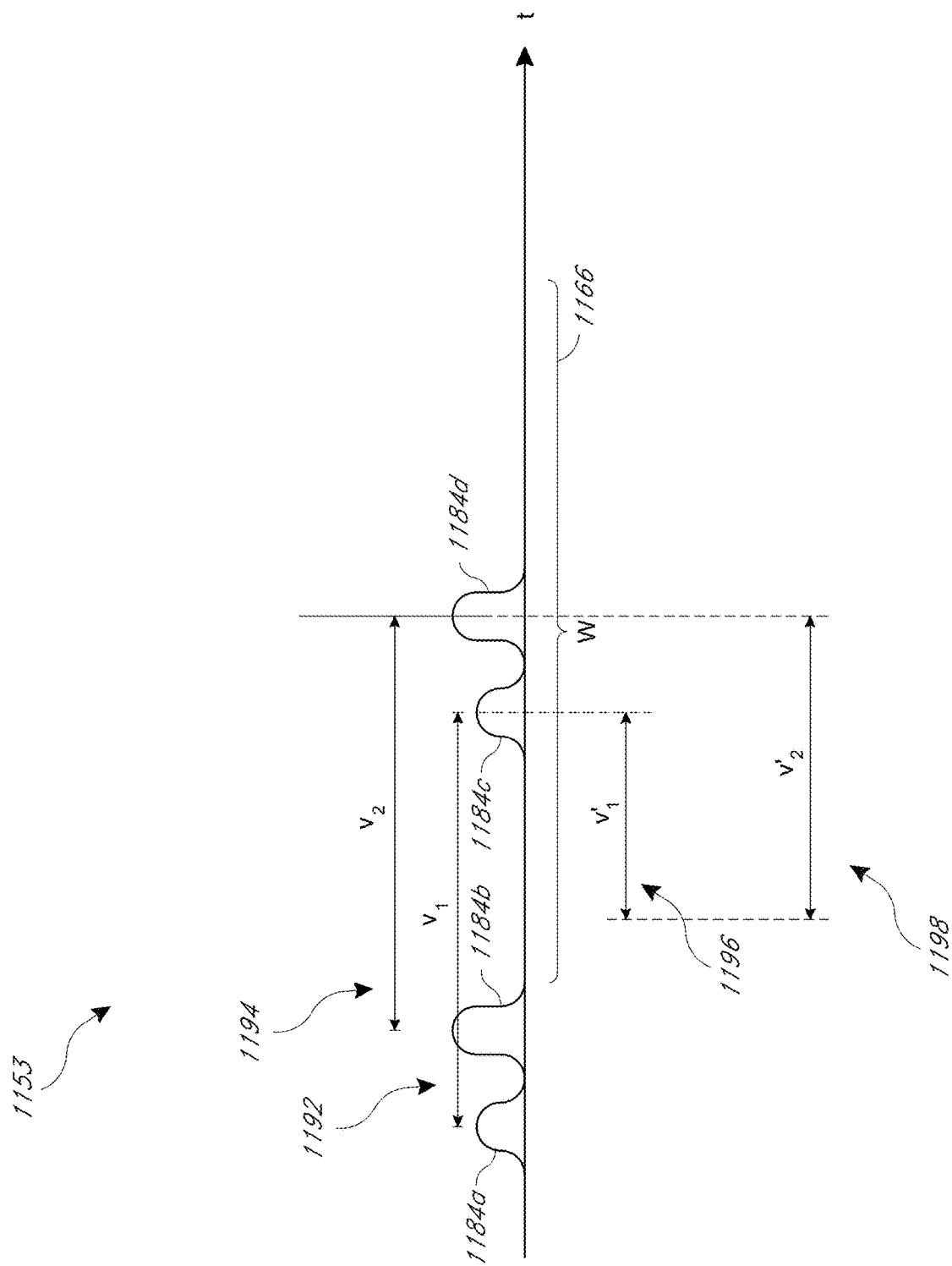

FIGS. 11B through 11D illustrate example time domain waveforms 1151, 1152, 1153 that can be analyzed by the time domain respiratory rate processor described above. As described above, the RR estimation module 1030 can calculate an average or weighted average of individual respiratory rate values for pairs of tags within a processing frame. The time domain waveforms 1151, 1152, 1153 illustrate an embodiment of a technique for computing a weighted average. Further, the time domain waveforms 1151, 1152, 1153 illustrate how an occurrence value or occurrence weighting can be computed for each pair of tags. The occurrence value can be used in an arbitration or decision logic process, described below with respect to FIGS. 16 through 18.

As described above, respiratory rate can be calculated for each first and third tag (e.g., inspiration peak to inspiration peak or expiration peak to expiration peak). However, for ease of illustration, time periods in FIGS. 11B and 11C are calculated between successive peaks. FIG. 11D illustrates how the features described with respect to FIGS. 11B and 11C can be extended to first and third peaks.

In the plot 1151 and 1152, peaks or tags 1154a, 1154b, 1154c, and 1154d are shown along a timeline. In the plot 1151, a time period 1170 between the first two peaks 1154a and 1154b is 20 seconds. A time period 1172 between the peaks 1154b and 1154c is 5 seconds, and a time period 1174 between peaks 1154c and 1154d is also 5 seconds. Two processing windows (or frames) 1162, 1164 are shown. Processing windows can be slid over time, causing older peaks to fall out of the window and newer peaks to enter. Thus, the second window 1164 occurs after the first window 1162.

If the RR estimation module 1030 were to compute a respiratory rate value for each window 1162, 1164 using simple averaging, the respiratory rate values for each window 1162, 1164 would differ substantially in this example. The average period for the first window 1162 would be equal to (20 seconds+5 seconds+5 seconds)/3, resulting in an average 10 second period. The average respiratory rate value for this window 1162 would then be $\frac{1}{10}*60$ seconds, or 6 breaths per minute (BPM). The average time period between peaks for the second window 1164 is (5 seconds+5 seconds)/2=5 seconds, resulting in an average respiratory rate of 12 BPM. This respiratory rate value is twice the respiratory rate value calculated for the first time window 1162, resulting in a significant jump or discontinuity between respiratory rate values. This jump results from the respiratory rate value from the oldest tag 1154a being dropped from the second window 1164.

To reduce or prevent these jumps in average respiratory rate values between windows, a weighted average can be computed instead of a simple average. This weighted average is illustrated in the plot 1152 of FIG. 11C. In the plot 1152, an approach for counting the most recently-dropped peak 1154a from the second window 1164 is shown. The period between the most-recently dropped peak 1154a and the next peak 1154b in the second window 1164 is denoted as v. A partial period v' is also shown. This partial period v' denotes the period between the start of the current window 1164 and the center (or some other feature) of the first peak 1154b in the current window 1164. A weight can be assigned to the contribution of the period v to the window 1164 by the ratio v'/v. Thus, if the peak 1154a were within the window 1164, the ratio v'/v would be 1. If the period v extended halfway out of the window 1164, the ratio v'/v would be 0.5. The farther out of the window the most recently-dropped peak 1154a is, the less weight or contribution this peak may have to the average respiration calculated for the window 1164.

The weights for pairs of peaks remaining in the window 1164 can simply be 1. Thus, the average respiratory rate in BPM for a window can be computed as follows:

$$\frac{60}{n} \cdot \sum_{i=1}^{n} v_i T_i$$

where n represents the number of tag pairs in the window, $T_i$ represents the time period of the ith tag pair, and $v_i$ represents the ith weight, which may be 1 for all weights except $v_1$, which is equal to v'/v.

In the plot 1153 of FIG. 11D, the features of FIGS. 11B and 11C are extended to detecting respiratory rates between first and third peaks. Peaks shown include peaks 1184a, 1184b, 1184c, and 1184d. The peaks 1184a and 1184b can correspond to inspiration and expiration, respectively. Similarly, the peaks 1184c and 1184d can correspond to inspiration and expiration as well. Instead of calculating respiratory rate for successive peaks, respiratory rate can be calculated for alternating (e.g., first and third). Thus, respiratory rate can be calculated between the inspiration peaks 1184a and 1184c and again between the expiration peaks 1184b and 1184d. Accordingly, a first time period 1192 between the inspiration peaks 1184a and 1184c, represented as $v_1$, and a second time period 1194 between the expiration peaks 1184b and 1184d, represented as $v_2$, can be calculated.

A processing window 1166 is shown. This window 1166 does not include the two initial peaks 1184a and 1184b. Partial periods $v_1'$ and $v_2'$ can be calculated as shown. The partial period $v_1'$ can be calculated as the time difference between the start of the window 1166 and a feature of the next alternate peak (1184c). Similarly, the partial period $v_1'$ can be calculated as the time difference between the start of the window 1166 and a feature of the next alternate peak (1184*d*). The weights of contributions of the periods from the earlier peaks 1184*a* and 1184*b* can therefore be $v_1'/v_1$ and $v_2'/v_2$, respectively.

Generally, weight $v'/v$ can also be referred to as an occurrence value, reflecting an amount of occurrence that a particular peak has on a processing window. In one embodiment, the time domain respiratory processor 1000 can output an occurrence value for each tag in a processing window. The use of the occurrence value is described below with respect to FIGS. 16B through 18.

Figure 12:
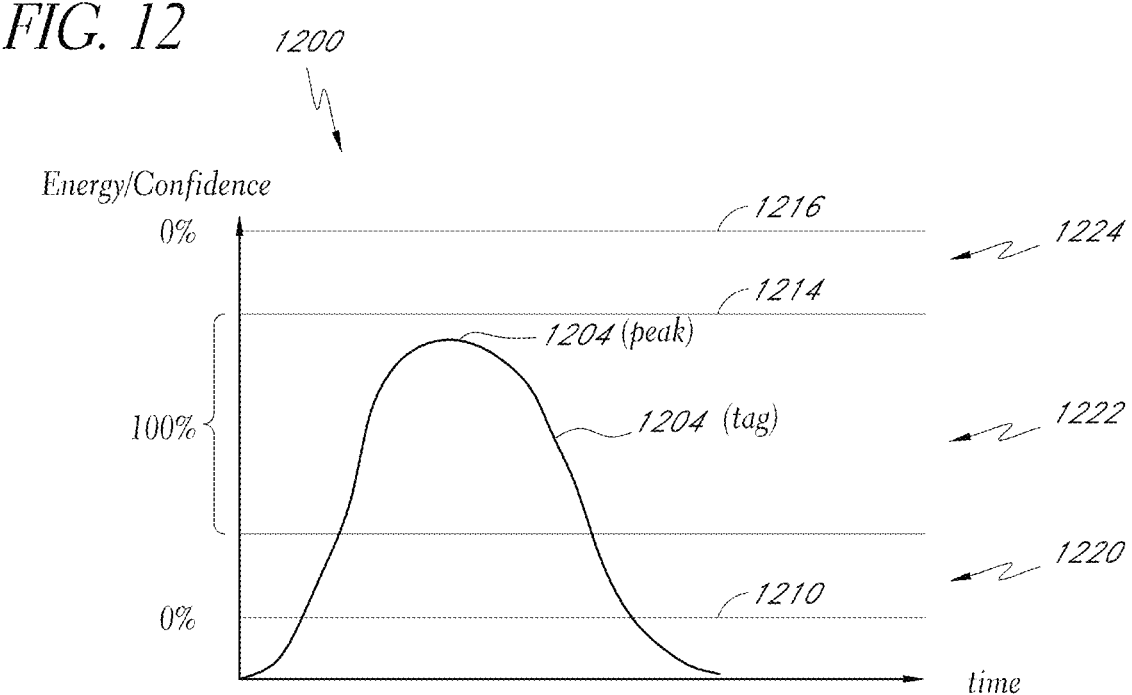
FIG. 12 illustrates an example time domain waveform corresponding to an acoustic signal derived from a patient.

The time domain power analysis technique can be described in the context of FIG. 12, which illustrates an example time domain plot 1200. The plot 1200 illustrates a wave form 1202, which represents a tag. The tag waveform 1202 is plotted as energy or magnitude with respect to time. Confidence values ranging from 0% confidence 100% confidence are also indicated on the y-axis.

The noise floor signal received by the confidence estimation module 1140 is plotted as the line 1210. The line 1210 is a simplified representation of the noise floor. Other lines 1212, 1214, and 1216 are drawn on the plot 1200 to represent different regions 1220, 1222, and 1224 of the plot 1200. A peak 1204 of the tag 1202 falls within the region 1222. In the depicted embodiment, tags having peaks falling within this region 1222 are assigned 100% confidence.

If the peak 1204 were in the region 1220, the confidence assigned would be less than 100%. The confidence can drop off linearly, for example, from the line 1212 to the line 1210. Confidence can decrease as the peak is smaller because the peak would be close to the noise floor 1210. Peaks falling below the noise floor 1210 can be assigned 0% confidence.

Likewise, peaks that exceed a threshold represented by the line 1216 can also have zero confidence. These large peaks are more likely to represent talking or other noise, rather than respiration, and can therefore be assigned low confidence. From the line 1214 representing the end of the 100% confidence region, confidence can linearly decrease as peak amplitude increases to the line 1216.

The threshold represented by the lines 1210, 1212, 1214, and 1216 can be changed dynamically. For instance, the thresholds represented by the lines 1210 and 1212 can be changed based on a changing noise floor. In certain embodiments, however, the upper thresholds represented by the lines 1214, 1216 are not changed.

It should be understood, in certain embodiments, that the plot 1200 need not be generated to determine confidence in the respiratory rate values. Rather, the plot 1200 is illustrated herein to depict how one or more dynamic thresholds can be used in the time domain to determine respiratory rate confidence.

As mentioned above, the confidence estimation module 1140 can also analyze the distribution of frequency components corresponding to the tags in the frequency domain. The confidence estimation module 1140 can analyze the frequency components using the spectral envelope described above. A spectrogram can be plotted to illustrate how confidence can be calculated from the spectral envelope, as shown in FIG. 13A.

FIG. 13A illustrates an example spectrogram 1300 that can be used by the confidence estimation module 1140 to determine respiratory rate confidence. The spectrogram 1300 can include a spectral envelope 1302 corresponding to the same frame or block of samples used to analyze confidence of the tags described above. The spectral envelope 1302 is plotted as peak frequency with respect to time. Thus, for each moment in time, the maximum frequency of the acoustic signal is plotted. Confidence values are also indicated on the y-axis.

In certain embodiments, respiration sounds can approximately correspond to white noise. However, respiration sounds are generally distributed in the frequency range of about 0 Hz to about 2 kHz. More particularly, in certain embodiments, respiration sounds can be distributed in the frequency range of about 200 Hz to about 1.2 kHz. Below about 200 Hz, sounds are usually hard sounds. Above about 1.2 kHz, sounds include moans, size, speech (speech also has lower frequency components), and the like.

Thus, in a first region 1322 (denoted by lines 1312 and 1314), 100% confidence is assigned if a peak falls within this region 1322. Peaks falling outside of this region 1322 can have a confidence that drops off linearly to 0% confidence, as shown in the FIGURE.

In certain embodiments, this confidence value determined from the spectrogram 1300 can be further refined by the density of the spectrogram at each peak. If a peak at a given point in time represents narrowband or periodic noise (e.g., a pure tone), it may have been derived from a spectrum having fewer frequency components than a respiration spectrum. The frequency spectrum corresponding to the time where the peak occurs can therefore be considered to be less dense. In contrast, if a peak at a given point in time comes from a broader spectrum, that peak can be considered to be denser. Spectral density is schematically represented by line 1330, with more tick marks on the line representing greater density.

If the density is low, the peak can likely represent narrowband noise or periodic noise. An example of narrowband noise can include an alarm from a medical instrument. Examples of periodic noise can come from medical instrumentation that emits periodic noise, such as CPAP machine cycles, noise from motors, and the like. Periodic noise can also result from speech, closing doors, motor vehicles (e.g., in the hospital parking lot), and the like. If the density is higher, the peak more likely represents a respiration sound because respiration can be relatively more broadband than narrowband or periodic noise. As a relatively broadband signal, respiration can include more spectral components than a narrowband signal. Thus, respiration signals can be more spectrally dense than narrowband noise signals.

In fact, in some instances, respiration can resemble white noise over a certain bandwidth. Somewhat paradoxically, the broadband sound (respiration) is the signal that is to be detected, rather than the narrowband/periodic sound, which can be the noise. This detection problem contrasts with typical detection problems where a narrowband signal of interest is to be detected from broadband noise.

Thus, in certain embodiments, the calculated density of spectral information corresponding to a time when a peak can be used at least in part to determine confidence values. In brief, the denser a signal is, the more confident the respiration processor can be that the signal contains respiration. Conversely, the less dense the signal, the less confident the respiration processor can be that the signal includes respiration. More detailed features for computing and analyzing spectral density are described below with respect to FIGS. 13B through 13D.

Referring again to FIG. 11A, the confidence estimation module 1140 can combine the confidence values derived from the TD and FD techniques described above. Advantageously, in certain embodiments, using these different techniques increases the accuracy of the confidence calculation. For example, the confidence estimation module 1140 can average the confidence values derived from both techniques to produce confidence values for each tag in a frame or block. Moreover, the confidence estimation module 1140 can look at the statistical distribution of shapes of peaks, for example, by determining if tags are similar, to further increase or decrease the calculated confidences in a frame or block.

Figure 13B:
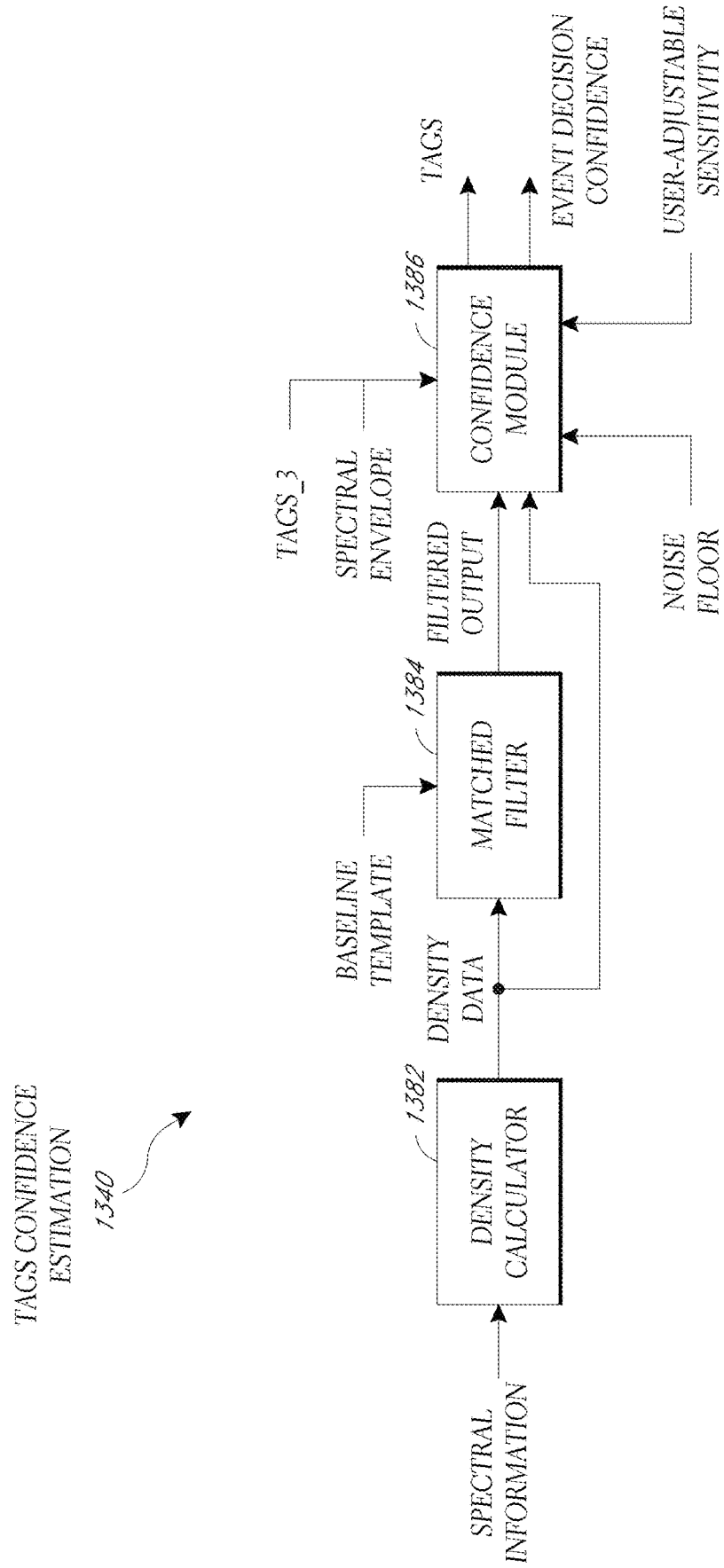
FIG. 13B illustrates an embodiment of a tags confidence estimation module.

FIG. 13B illustrates a more detailed embodiment of the confidence estimation module 1140, namely the confidence estimation module 1340. In the depicted embodiment, the confidence estimation module 1340 includes a density calculator 1382, a matched filter 1384, and a decision/confidence block 1386. In one embodiment, these components 1382, 1384, 1386 include hardware and/or software. Another view of these components is that the blocks 1382, 1384, 1386 represent algorithm or process flow states that can be implemented by hardware and/or software. Advantageously, in certain embodiments, the confidence estimation module 1340 can use spectral density, spectral envelope, and other features described above to compute confidence in a respiratory measurement. Moreover, as will be described in greater detail below, the confidence estimation module 1340 can use these features to detect respiratory pauses and other respiratory events, such as apnea, hypopnea, and the like.

In the depicted embodiment, spectral information is provided to the density calculator 1382. This spectral information was described above with respect to FIG. 8 as being calculated by the FD envelope processor 500. In certain embodiments, the spectral information can include the power spectrum of the working time domain signal (e.g., the signal received by the FD envelope processor 500). Advantageously, in certain embodiments, the density calculator 1382 computes spectral density from the spectral information. As described above with respect to FIG. 13, higher spectral density can be more representative of respiration, while lower spectral density can be more representative of narrowband and/or periodic noise.

Figure 13C:
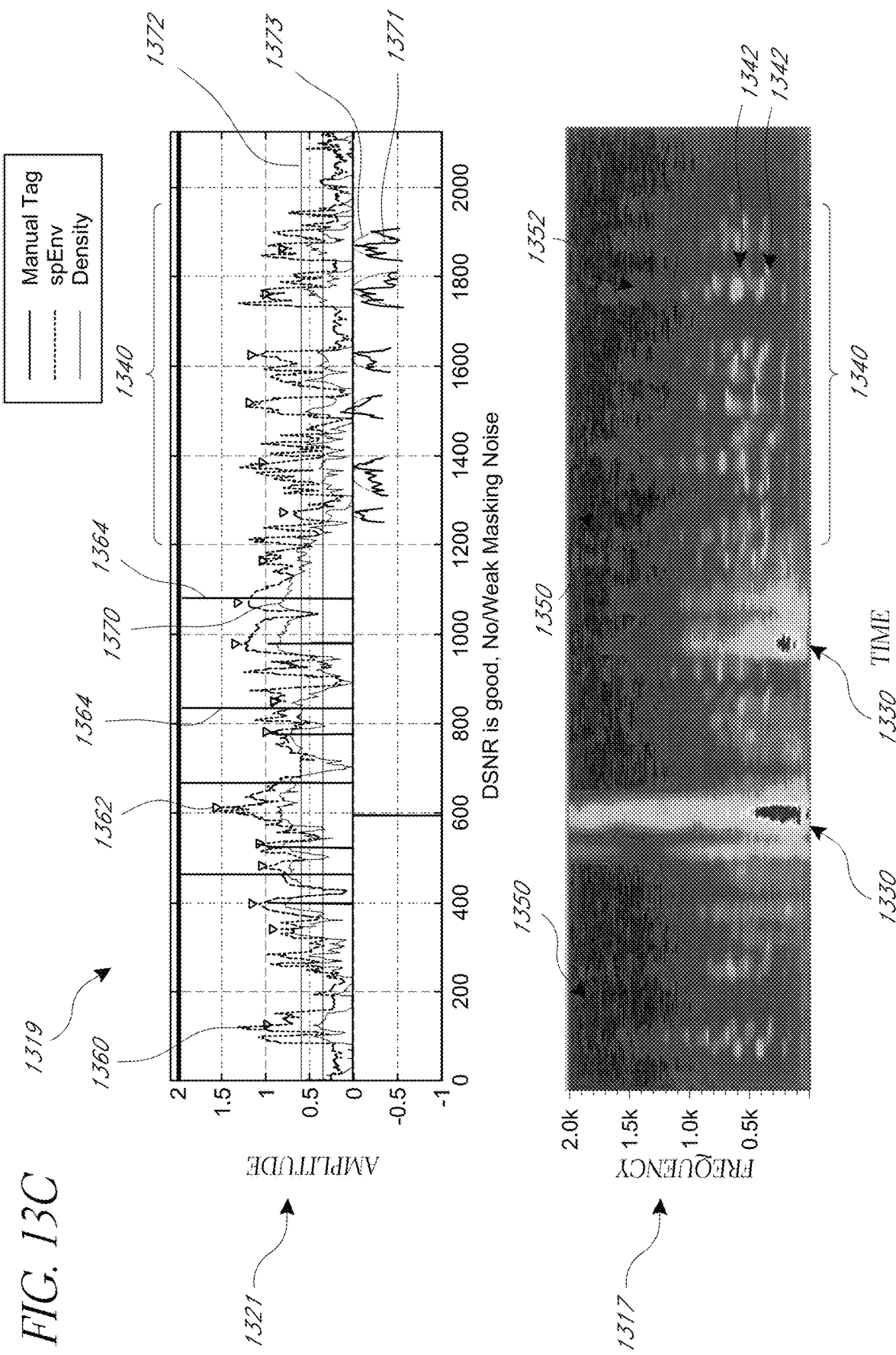
FIG. 13C illustrates an embodiment of a spectrogram and a time domain plot together on the same time scale.

Spectral density as calculated by the density calculator 1382 can be further understood in the context of example waveforms 1319 depicted in FIG. 13C. In FIG. 13C, these waveforms 1319 include a spectrogram 1317 of the spectral information and a graph 1321 of spectral peaks plotted over time (a one-dimensional spectrogram 1360) and spectral density 1370 plotted over time, among other features. The waveforms 1319 shown are used herein to facilitate a description of spectral density calculations, among other features. The waveforms shown 1319 may or may not be output on a patient monitor in various embodiments.

The spectrogram 1317 is plotted with respect to frequency over time. At each slice in time (represented on the "x" axis), a magnitude frequency response is plotted (represented on the "y" axis). This magnitude frequency response can be obtained, as described above, from an FFT performed on a block or frame of input samples. In the depicted example spectrogram 1317, the magnitude of a particular frequency is illustrated by the brightness or intensity of the points (e.g., pixels) in the spectrogram. Thus, brighter points tend to represent higher frequency magnitudes while dimmer pixels tend to represent lower frequency magnitudes.

The spectrogram 1317 differs from the spectrogram 1300 shown in FIG. 13A in that the spectrogram 1317 shows all (or substantially all) frequencies of the spectral information over time, whereas the spectrogram 1300 shows the peak frequency of the spectral information over time. For comparison, the spectrogram 1360 (referred to herein as a one-dimensional spectrogram, in contrast with the multi-dimensional spectrogram 1317) shown in the graph 1321 is an example implementation of the spectrogram 1300 of FIG. 13.

Some features of the spectrogram 1317 include respiration portions 1330, speech portions 1340, narrowband portions 1342, and ambient noise portions 1350. The respiration portions 1330 in the depicted embodiment extend through most of all of the frequency spectrum (e.g., at a given point in time), illustrating how respiration can be broadband sound. In the depicted embodiment, the energy of the respiration portions 1330 is greatest in the lower frequencies (e.g., below about 1 kHz), although this may not always be the case. Because respiration energy can sometimes be greatest in the lower frequencies, the confidence estimation module 1340 of FIG. 13B can consider signals having greater energy in the lower frequencies to more likely be respiration. The confidence estimation module 1340 can use this information about the frequency locations of signal energy as an input to a confidence calculation.

The speech portions 1340 of the example spectrogram 1317 reflect an example pattern of speech. As speech can include periodic or narrowband signals, narrowband portions 1342 are illustrated in the speech portion 1340. These narrowband portions 1342 appear as striations on the spectrogram 1317. At any one slice in time, the frequency response at the speech portions 1340 of the spectrogram 1317 are less dense than the example respiration portions 1330. The confidence estimation module 1340 of FIG. 13B can use this density information to distinguish between respiration and speech, as well as other noise signals.

The ambient noise portions 1350 reflect low-level background noise from the environment (e.g., the environment around a patient). For example, the ambient noise can include white noise. Because this ambient noise has signal energy, it can adversely affect a density calculation by inflating the calculated density. Thus, in certain embodiments, the density calculator 1382 of FIG. 13B can advantageously reduce the effect of the ambient noise 1350 on a density calculation. For example, the density calculator 1382 can exclude the ambient noise from the density calculation.

Figure 13D:
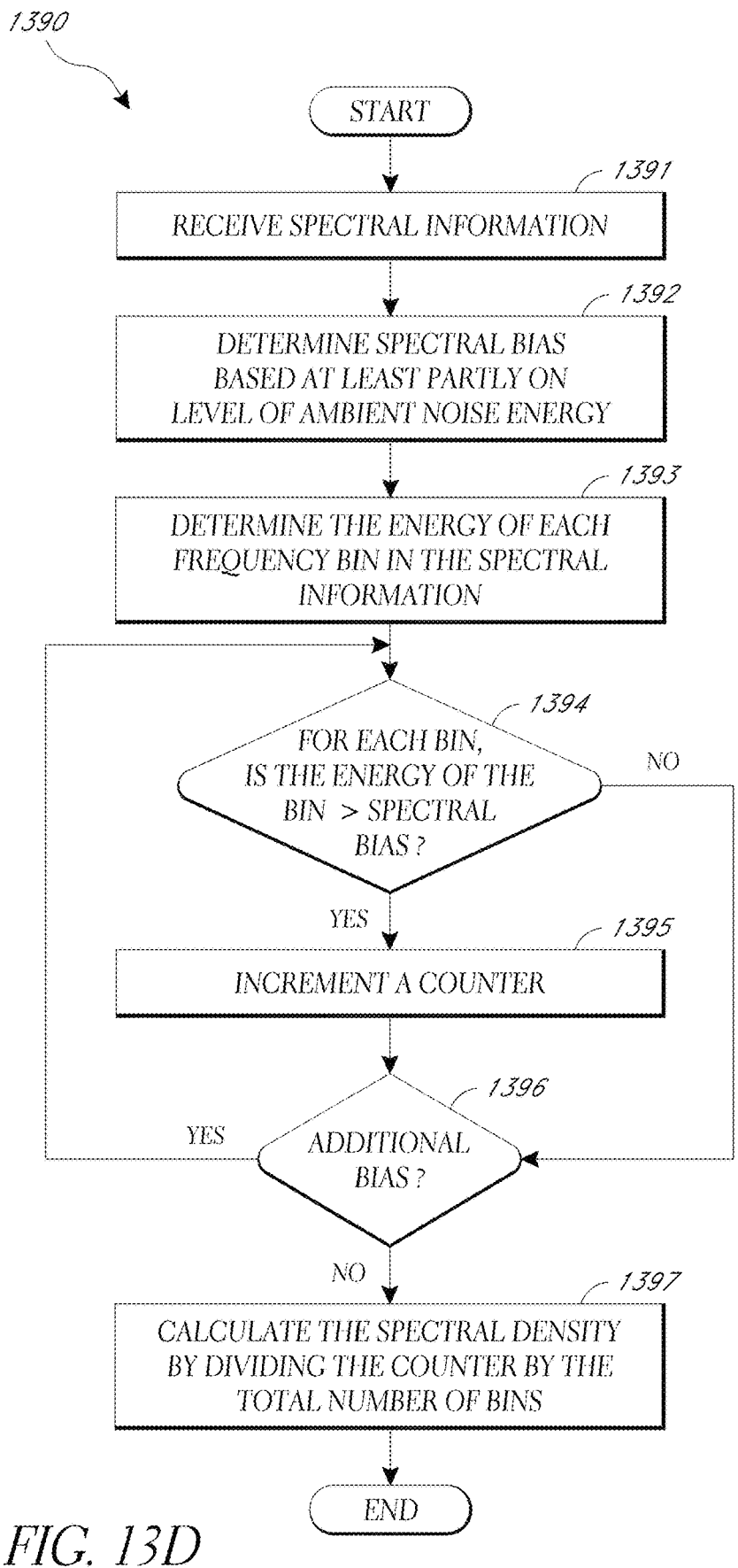
FIG. 13D illustrates an embodiment of a process for computing spectral density.

An example process 1390 for calculating spectral density that takes into account the ambient noise 1350 is illustrated in FIG. 13D. The process 1390 can be implemented by the density calculator 1382. Referring to FIG. 13D, the process 1390 receives the spectral information described above at block 1391. At block 1392, a spectral bias is determined based at least partly on the level of the ambient noise energy. The spectral bias can be the level of the ambient noise energy. The level of the ambient noise energy can be calculated in a variety of ways. One approach for determining the ambient noise energy within a given time period is to calculate the spectral centroid from the spectral information. The spectral centroid can be calculated as a weighted mean of the frequencies present in the spectral information, with the magnitudes of the frequencies as the weights (see FIGS. 13E through 13G).

Over time, the spectral bias can be smoothed or averaged, for example, by applying a weighted average or the like. Any smoothing filter can be used to average the spectral bias. For example, a first-order IIR filter can be used to smooth the spectral bias. In one embodiment, the ambient noise energy is weighted such that the spectral bias decreases slowly but increases quickly. By decreasing slowly, the spectral bias can be used to exclude relatively louder ambient noises. By increasing quickly, the spectral bias can be used to assist with detection of shallow breathing signals.

At block 1393, the energy of each frequency bin in the spectral information is determined. As mentioned above with respect to FIG. 8, the spectral information can be obtained from the FFT of the working acoustic signal. The FFT can partition spectral information into a plurality of frequency bins. The number and size of the bins can be determined based on the sampling frequency and the number of points used to compute the FFT. Thus, for example, for a 4 kHz sampling frequency and a 256 point FFT, the frequency bin size can be about 15.625 Hz. The energy of each frequency bin can be determined by determining the magnitude or squared magnitude, for example, of the spectral information in each bin. In some embodiments, the energy of a subset of the bins, rather than each of the bins, is calculated.

At decision block 1394, it is determine for each bin, whether the energy of the bin is greater than the spectral bias. If so, then a counter is incremented at block 1395. Otherwise, the counter is not incremented, and the process 1390 proceeds to decision block 1396. Incrementing the counter for a bin can reflect that the bin is spectrally dense, or in other words, that the bin should be counted toward the spectral density calculation. Said another way, in certain embodiments, when the energy of a bin exceeds the ambient noise level of that bin, the bin is counted toward the spectral density.

At decision block 1396, it is further determined whether any additional bins remain to be processed. If so, the process 1390 loops back to block 1394. Otherwise, spectral density is calculated at block 1397, for example, by dividing the counter value by the total number of bins considered. In effect, the process 1390 can therefore determine the ratio (or percentage) of bins that have a spectral density above the spectral bias.

The spectral density can be determined using other techniques or algorithms. For example, spectral density can be computed by summing the energy levels (obtained at block 1393) for the bins. Further, in some embodiments, this sum can be divided by the total number of bins considered to arrive at a mean energy value. This mean energy value can be the spectral density. Many other techniques can be used to calculate the spectral density, as will be apparent from this disclosure.

Referring again to FIG. 13B, the density calculator 1382 can aggregate the spectral densities calculated for each block or frame of samples to output density data over time. An example of such density data is shown in the graph 1321 of FIG. 13C. In the graph 1321, a density waveform 1370 is shown, representing the calculated density over time. The time scale in the graph 1321 corresponds to the time scale used in the spectrogram 1317, for the same input acoustic signal. Inspection of the graph 1321 indicates that for periods of respiration 1330 shown in the spectrogram 1317, the density waveform 1370 is higher in magnitude, while for periods of speech 1340 and other noise, the density waveform 1370 is lower in magnitude.

Also shown in the graph 1321 is a one-dimensional spectrogram 1360, which includes the features of the spectrogram 1300 described above with respect to FIG. 13. This spectrogram 1360 includes the peak spectral value over time (e.g., the peak in the spectrogram 1317). Superimposed on the graph 1321 are markers 1362 representing tags detected by the time domain algorithms described above. The tags 1362 can reflect the tags_3, for example, described above with respect to FIG. 11A. A density threshold 1372 is also shown, which will be described in greater detail below.

Referring again to FIG. 13B, the density calculator 1382 provides the density data (corresponding to the density waveform 1370) to the matched filter 1384. The matched filter 1384 is an example of a detector that can be used to analyze the density data. Advantageously, in certain embodiments, the matched filter 1384 attempts to match the density data to a template or pattern to determine whether the density data corresponds to respiration. In one embodiment, a breath results in a sinusoidal-shaped pattern. The matched filter 1384 can convolve a portion of the density data with a sinusoidal-shaped pattern to determine whether the density data matches the sinusoidal-shaped pattern. Pattern-matching filters other than a matched filter can be used in other implementations.

An example illustrating the pattern matching techniques of the matched filter 1384 is shown in FIG. 13C. Referring again to FIG. 13C, the graph 1321 depicts sinusoidal patterns 1373 superimposed on portions 1371 of the density waveform 1370. The portions 1371 of the density waveform 1370 are shown as copies below the actual density waveform 1370 for illustration purposes. The density waveform portions 1371 can be centered on the locations of the tag indicators 1362 but need not be.

In the example embodiment shown, the density portions 1371 do not appear similar to the sinusoidal patterns 1373. Thus, the output of the matched filter 1384 would be relatively small, indicating that these density portions 1371 likely do not reflect the presence of respiration. This conclusion makes sense, given that the density portions 1371 analyzed fall within the breathing portion 1340 of the spectrogram 1317. Conversely, if the density portions 1371 more closely matched the sinusoidal patterns 1373, the output of the matched filter 1384 would be relatively larger, reflecting the possible presence of respiration.

Referring again to FIG. 13B, the matched filter 1384 can use other templates besides a purely sinusoidal template to compare with the density data. For instance, the matched filter 1384 can compare density data with a patients' baseline respiration density shape or template. An actual patient's baseline density shape (e.g., where the patient has breathed normally previously) may not be exactly sinusoidal. Thus, instead of using a sinusoid to detect breathing shapes in the density data, the matched filter 1384 can attempt to match the patient's baseline template with the density data.

The matched filter 1384 can initially detect the patient's baseline template using the sinusoidal template in one embodiment. The matched filter 1384 can also adjust the patient's baseline template over time as the patient's breathing changes. For instance, the matched filter 1384 can average a patient's density shapes for each detected respiration to derive an average baseline template.

The matched filter 1384 provides a filtered output. In one embodiment, the matched filter 1384 provides a higher output if the density data matches the template than if the density data does not match the template. The filtered output is provided to the confidence module 1386. The confidence module 1386 can receive the filtered output, the spectral envelope (see FIGS. 13A, 13C), the tags (e.g., the tags_3 of FIG. 11A), the noise floor (see FIG. 6), and a user-adjustable sensitivity (discussed below).

In certain embodiments, the confidence module 1386 calculates a confidence reflecting whether the identified tags represent breaths. The confidence module 1386 can calculate this confidence using the features described above with respect to FIG. 13. For example, the confidence module 1386 can determine where the peak of the spectral envelope at a given point in time lies, determine whether the spectral density (e.g., as computed by the density calculator 1382) at that peak exceeds a threshold, and so forth.

An example of such a density threshold 1372 is shown in FIG. 13C. At the points where tags occur (the indicators 1362), the confidence module 1386 can compare the value of the density waveform 1370 with the threshold 1372. If the density value exceeds the threshold 1372, the confidence module 1386 can assign higher confidence to the tag occurring at that density value. The confidence module 1386 can calculate a degree of confidence based at least in part on how far the density value exceeds the threshold 1372. The confidence module 1386 can calculate lower confidence values when the density value is below the threshold 1372.

The confidence module 1386 can further base confidence at least in part on the degree to which the filtered output from the matched filter 1384 exceeds a threshold. Thus, the confidence module 1386 can use both the density data and the matched filter 1384 output together to determine confidence. In some implementations, the confidence module 1386 can use one or both of density and matched filter 1384 output to determine confidence. The confidence module 1386 can also use other signal features to calculate confidence, some of which are discussed elsewhere herein.

In certain embodiments, the user-adjustable sensitivity input into the confidence module 1386 can advantageously adjust one or more of the thresholds used by the confidence module 1386. The user-adjustable sensitivity can be used to select between focusing on detecting non-respiration events (such as respiratory pauses, apnea, and the like) and focusing on detecting respiration events. In some care scenarios, it can be more important to a clinician to determine whether a patient is breathing than what the patient's precise respiratory rate is. Thus, the user-adjustable sensitivity can be used to select this preference. For example, in one embodiment, the user-adjustable sensitivity can be controlled by a clinician via a user interface on a patient monitor. A display button or other user interface control (such as a hardware button or switch) can allow the clinician to select between detecting respiratory pauses, apnea, or the like and more precise detection of respiratory rate.

If the clinician selects detection of respiratory pauses or the like, the user-adjustable sensitivity control can be adjusted to cause the density threshold 1372 to be set higher than if the clinician selects more accurate respiratory rate detection. Thus, the confidence module 1386 can intentionally under-read respiratory rate to more aggressively detect lack of breathing. By under-reading respiratory rate, the confidence module 1386 can ultimately cause more alarms to be triggered, enabling clinicians to respond to patients who are not breathing. Thus, scenarios can be avoided or reduced where clinicians are unaware of a patient's cessation of breathing, allowing clinicians to save more lives.

The user-adjustable sensitivity can be provided to the confidence module 1386 from the patient monitor. The user-adjustable sensitivity can be used by the confidence module 1386 to adjust the density threshold 1372 (see FIG. 13C), the matched filter threshold, or a combination of the same.

Another advantageous feature that can be provided in certain embodiments is to use manual tags generated by a clinician to train the confidence estimation module 1340. Example indicators 1364 of manual tags are depicted in FIG. 13C. The indicators 1364 represent instances where clinicians have marked that a patient actually breathed, e.g., by visually observing the patient breathing. These indicators can be used by the confidence estimation module 1340 during manufacturing, testing, and/or servicing to automatically improve confidence calculations. In one embodiment, an engineer can use the manual tag indicators 1364 to improve signal processing of the respiratory data.

Figure 13E:
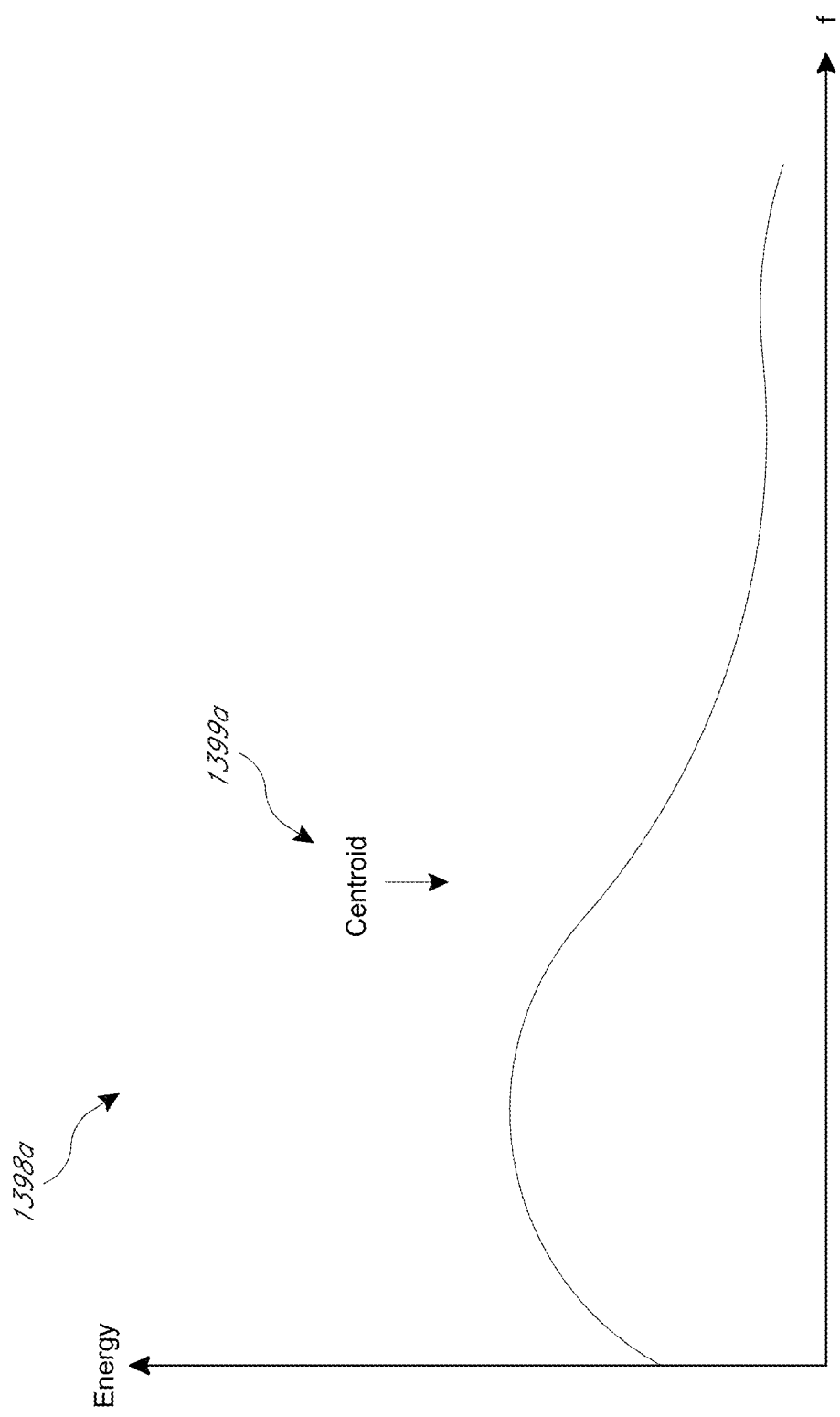

FIGS. 13E through 13G illustrate example spectrums 1398 for computing centroids. The centroids can be used, for example, to calculate ambient noise energy as described above. More generally, centroids can be calculated to assist with detection of background noise, detecting respiratory pauses, calculating confidence values, and so forth.

Referring to FIG. 13E, an example spectrum 1398a is shown at a point in time. The spectrum 1398a plots energy against frequency. More generally, any of the spectrums 1398 described herein can plot a frequency response magnitude, energy, power, or the like. The spectrum 1398a corresponds to an example respiration, having energy distributed primarily in lower frequencies rather than higher frequencies. A representation of a centroid 1399a is also shown. The centroid 1399a can be an equilibrium point about which the energy in the spectrum 1398a is equally divided. Thus, the energy in the spectrum 1398a to the left of the centroid 1399a can be equal or substantially equal to the energy to the right of the centroid 1399a. With more energy distributed toward the lower frequencies for a respiration spectrum 1398a, the centroid 1399a can be toward the lower end of the spectrum 1399a as well.

Other centroids can have higher values, such as the centroid 1399b in the spectrum 1398b (where energy is concentrated in high frequencies) and the centroid 1399c of the spectrum 1398c (where energy is distributed evenly across the spectrum 1398c). Thus, the higher the centroid 1399, the less likely the spectrum 1399 represents respiration, and vice versa.

In one embodiment, the tags confidence estimation module 1140 can analyze the centroid of a spectrum for a given point in time, in addition to or instead of analyzing spectral density, and spectral envelope peaks. The lower the centroid, the more confident the tags confidence estimation module 1140 can be that tags correspond to respiration, and vice versa. Similarly, the tags confidence estimation module 1140 can indicate that a respiration pause is more likely if the centroid is relatively higher than during respiration periods.

Another concept that can be useful in distinguishing respiration from respiratory pauses and background noise is entropy. Entropy, or Shannon entropy, can generally represent the order (or disorder) of a signal. A signal that is more ordered, such as speech (which tends to have well-ordered harmonics), can have a higher entropy value. A signal that is less ordered, such as respiration, can have a lower entropy value. Thus, the tags confidence estimation module 1140 can calculate the entropy of an acoustic signal (e.g., according to processing windows) and can compare the entropy of the acoustic signal to some threshold to estimate whether the signal represents background noise/respiratory pauses or respiration.

In other embodiments, trends of centroids and entropy values are analyzed instead of thresholds. Further, entropy and centroids can be analyzed together to estimate confidence/respiratory pauses, and the like. In addition, entropy, centroids, spectral density, and spectral envelope peaks can be used together to estimate confidence/respiratory pauses, and the like. For instance, each of these quantities can be normalized on a scale (such as from 0 to 1) and multiplied together to produce a probability of respiration. If the multiplied value is close to 1 on a scale of 0 to 1, the probability that a respiration is detected can be close to 1, and vice versa. Some subset of the parameters entropy, centroids, spectral density, and spectral envelope peaks can be used to analyze confidence and/or respiratory pauses in different implementations. Other parameters may also be used, including other statistical parameters.

Referring again to FIG. 10, the RR estimation module 1030 can receive the tags and calculated confidence values and the tags from the automatic tagging module 1020. As described above, the RR estimation module 1030 can calculate respiratory rate from the tags and an overall TD RR confidence from the individual tag confidence values in a frame or block. In one embodiment, the RR estimation module 1030 counts the number of tags occurring in a frame or block and uses this count to derive respiratory rate based on the amount of time represented by the frame or block. In another embodiment, the RR estimation module 1030 determines respiratory rate based on the difference in time between different tags in a frame or block. The two possible TD RR values are represented as TD RR 1 and TD RR 2 in the FIGURE. In some embodiments, only one method is used to calculate the TD RR.

The RR estimation module 1030 can determine the overall TD RR confidence value for a given block or frame by averaging confidence values for each peak or tag within the frame. The RR estimation module 1030 can therefore output an overall TD RR confidence value.

Frequency Domain RR Calculation

Figure 14:
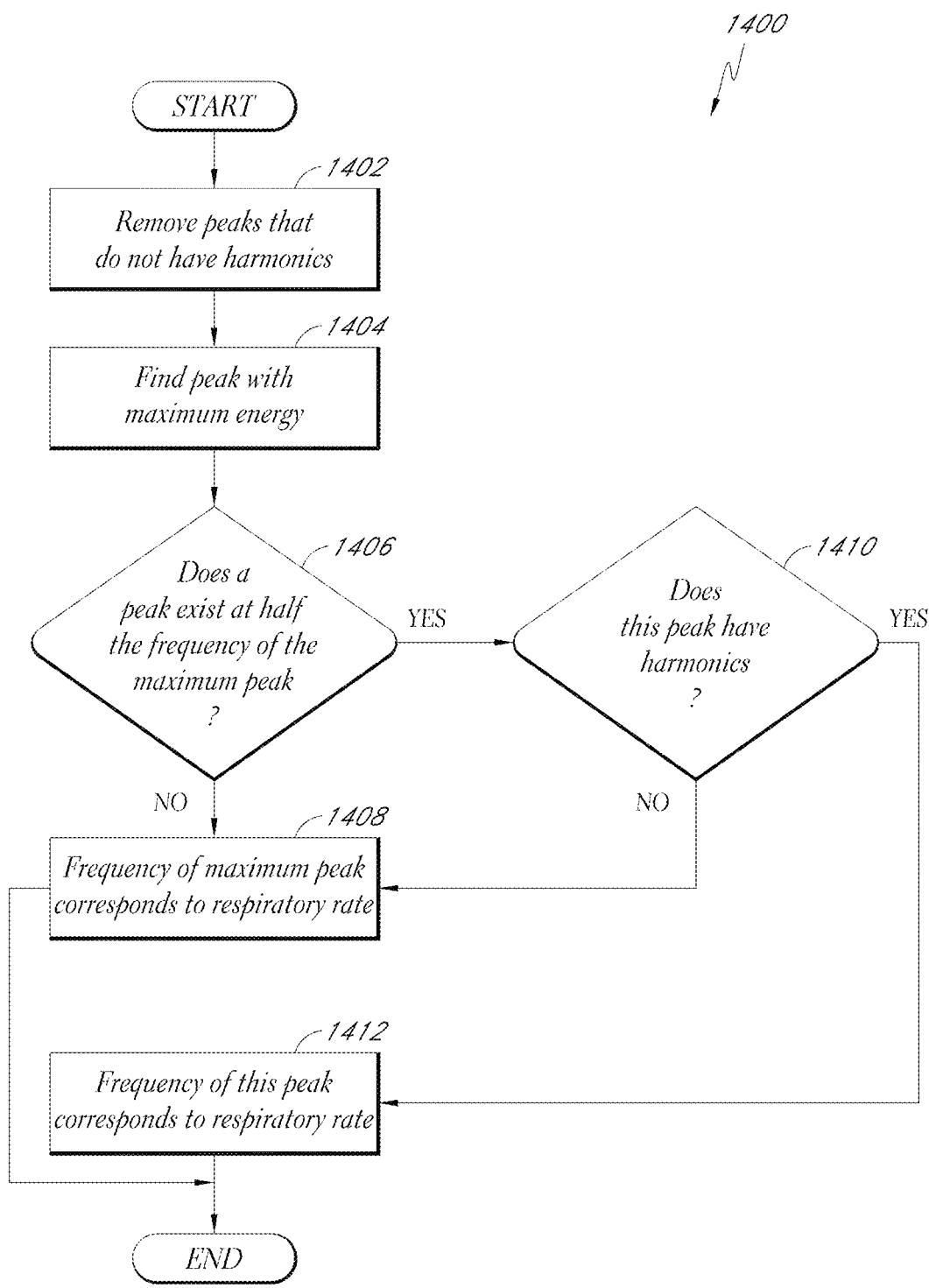
FIG. 14 illustrates an embodiment of a process for calculating respiratory rate in the frequency domain.

FIG. 14 illustrates an embodiment of a frequency domain respiratory rate (FD RR) calculation process 1400. The FD RR calculation process 1400 can be implemented by the FD RR processor 920 described above with respect to FIG. 9. Advantageously, in certain embodiments, the FD RR calculation process 1400 can calculate a respiratory rate value based on frequency domain analysis.

The FD RR calculation process 1400 can analyze an FD envelope obtained above. The FD RR calculation process 1400 will be described in the context of the example frequency envelopes or spectrums 1510, 1520 shown in FIGS. 15A, 15B respectively. Each spectrum 1510, 1520 is plotted as magnitude versus frequency.

Figure 15A:
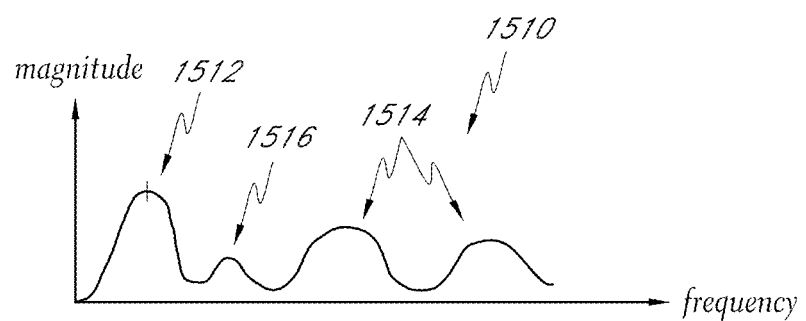
FIGS. 15A and 15B illustrate example frequency spectrums corresponding to an acoustic signal derived from a patient.
Figure 15B:
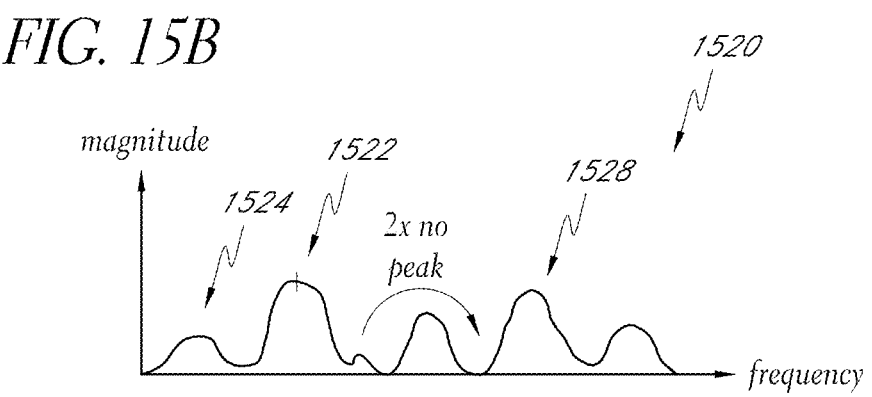

At block 1402, peaks that do not have harmonics are removed from the frequency envelope. Referring to FIG. 15A, a peak 1512 has harmonics 1514, which can be integer multiples of the frequency of the peak 1512. In contrast, peak 1516 does not have a corresponding harmonic. This can also be seen in FIG. 15B, where a peak 1526 does not have a corresponding harmonic. These peaks could therefore be removed from the spectrum because they likely do not correspond to respiration.

Referring again to FIG. 14, a peak with maximum energy is found at block 1404. In FIG. 15A, the maximum energy peak is peak 1512, and in FIG. 15B the maximum energy peak is peak 1522. It is determined at decision block 1406 whether a peak exists at half the frequency of the maximum peak. If not, at block 1408, the frequency of the maximum peak is determined to correspond to the respiratory rate, and the process 1400 ends.

Thus, in FIG. 15A, there is no peak at half the frequency of the maximum peak 1512, and therefore the frequency of this peak 1512 corresponds to the respiratory rate. In contrast, there is a peak 1524 at half the frequency of the maximum peak 1522 in FIG. 15B. Thus, the analysis continues.

Referring again to FIG. 14, if there is a peak at half the maximum peak's frequency, at decision block 1410, it is further determined whether this peak has harmonics. If not, the frequency of the maximum peak corresponds to respiratory rate in block 1408, and the process ends. Otherwise, the frequency of the peak at half the maximum peak's frequency corresponds to respiratory rate at block 1412, and the process ends. Thus, for example, in FIG. 15B, the peak 1524 has a harmonic at peak 1522 (the maximum peak), peak 1528, and so on. Therefore, this peak is determined to have a frequency corresponding to respiratory rate.

Although not shown, in some cases, although the first peak has harmonics, the maximum peak may still be selected as corresponding to respiratory rate based on historical past respiratory rate values. For instance, if the respiratory rate value calculated by the first peak is much different from the previously calculated value, the respiratory rate value for the second peak may be selected if it is closer to the historical value. In addition, although example spectrums have been shown in FIGS. 15A and 15B, many other spectrums shapes and types can exist. Thus, the FD RR processor 920 and the process 1400 can be adjusted or adapted accordingly to account for different types of spectrums.

Referring again to FIG. 9, the FD RR processor 920 can calculate FD RR confidence as follows. In one embodiment, the FD RR processor 920 can sum the energy of all or substantially all the harmonics in the FD envelope or spectrum. The FD RR processor 920 can further determine the energy of the entire envelope or spectrum. The confidence can be equal to, or derived from, the total harmonic energy divided by the total energy in the spectrum. Thus, if there is substantially more energy in the spectrum other than harmonic energy, the confidence can be low, and vice versa.

In some embodiments, if the amplitude of the acoustic signal for a given frame or processing window is small (e.g., below a threshold), the frequency domain processor can zero out or otherwise perform no analysis. Similarly, if the respiratory rate calculated by the frequency domain processor is very high (e.g., above a threshold where patients typically cannot breathe so fast), the frequency domain processor can zero out the calculated respiratory rate value. Alternatively, in either the case of low signal level or high calculated respiratory rate, the frequency domain processor can calculate low or zero confidence instead of zeroing out the frequency domain respiratory rate value.

Arbitrator

Advantageously, in certain embodiments, FD RR analysis can be simpler than TD RR analysis. However, using both in conjunction can reduce errors and provide more accurate confidence analysis. For instance, if the FD spectrum includes harmonic peaks that are substantially equal in value, it can be difficult to determine which corresponds to inspiration and which correspond to expiration. Thus, the FD RR processor 920 might calculate a respiratory rate that is double the actual respiratory rate. The RR calculated in the time domain, if half that rate, is likely to be more accurate. In certain embodiments, the arbitrator 930 described above arbitrates between the TD and FD engines to output a more accurate respiratory rate value.

Figure 16A:
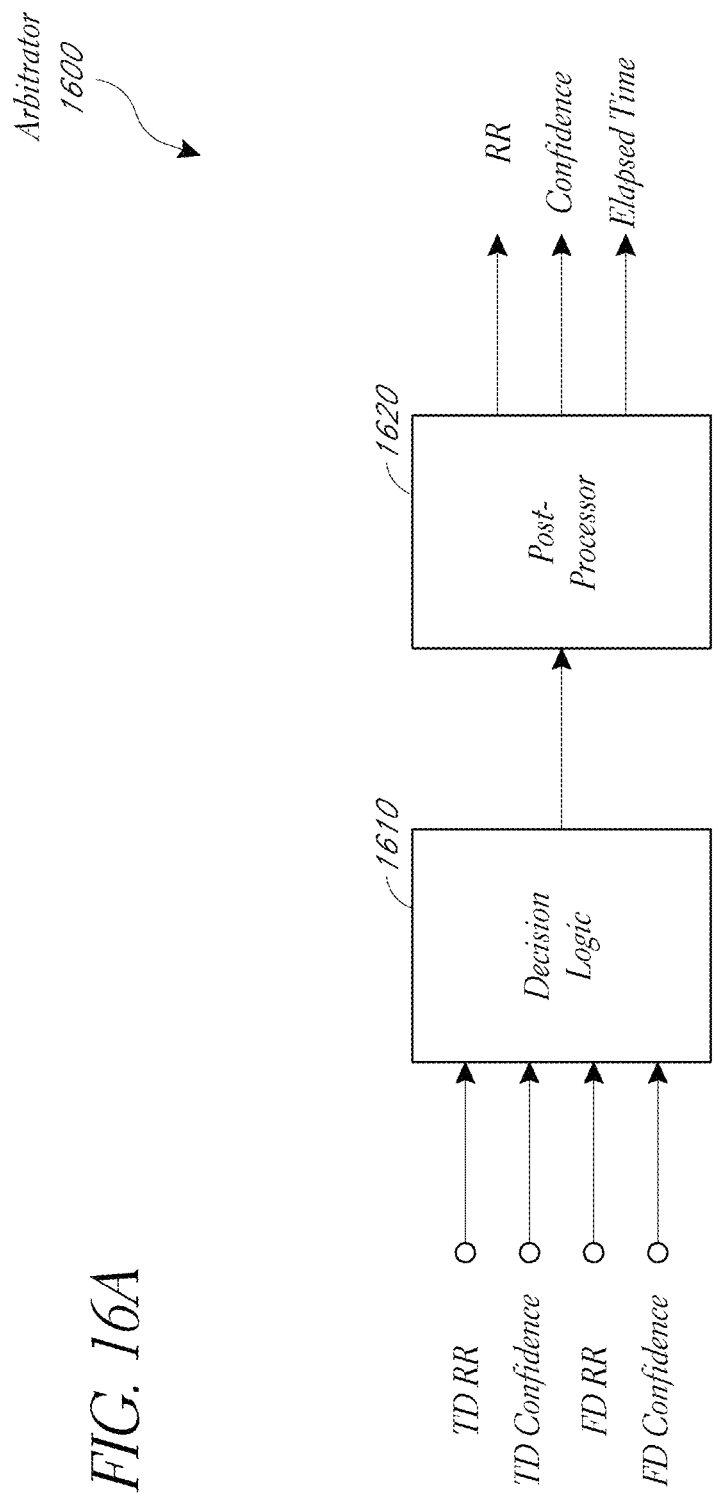
FIG. 16A illustrates an embodiment of an arbitrator of the back end processor of FIG. 9.

FIG. 16A illustrates a more detailed embodiment of an arbitrator 1600 corresponding to the arbitrator 930 of FIG. 9. The arbitrator 1600 can be implemented in software and/or hardware. Advantageously, in certain embodiments, the arbitrator 1600 can combine and/or select from the TD and FD RR values and from the TD and FD confidence values.

The arbitrator 1600 includes a decision logic module 1610 and a post-processing module 1620. The decision logic module 1610 can receive the TD and FD RR and confidence values. The decision logic module 1610 can select RR and confidence values within a block or frame, whereas the post-processing module 1620 can determine an overall RR and an overall confidence value for a period of time. As frames can overlap, the post-processing module can determine the overall RR and confidence values for several frames.

The post-processing module 1620 can output the RR value, the confidence value, and the elapsed time value discussed above for presentation to a user. The confidence value output by the post-processing module 1620 can be referred to as a respiratory signal quality (RSQ) value or indicator. However, any confidence value described herein could also be referred to as a respiratory signal quality (RSQ) value or indicator.

Several techniques of the decision logic module 1610 will now be described, some of which may be implemented in certain embodiments, while others are implemented in others. All techniques may also be implemented. It should also be noted that two TD RR values and possibly two confidence values can be output by the TD RR processor 910, as described above. Either of these TD RR values can be compared with the FD RR value or an average of the two can be compared with the FD RR value. Or, each can be compared with each other using the techniques described below, and then one can be selected and compared with the FD RR value.

In certain embodiments, the decision logic module 1610 can compare the TD and FD RR values within a frame to determine if they are close to each other. If they are close, the decision logic module 1610 could output either value. In one embodiment, the decision logic module 1610 outputs the value with the higher associated confidence value. If the values are not close, the decision logic module 1610 can output the RR value from the engine that is closest to a previous RR value.

If both TD and FD RR values are of high confidence but not close (within a delta), and neither is close to a previous value, then the decision logic module 1610 can output one of the values if it passes other checks. For instance, if the FD value is double the TD value (e.g., for reasons discussed above), the decision logic module 1610 could output the TD value instead.

In one embodiment, the decision logic module 1610 outputs a RR value only if either the TD or FD confidence is above a threshold. If both are below a threshold (which may differ for both), the decision logic module 1610 can output a zero RR value or "not a number" (NaN) type RR value.

The post-processing module 1620 can average or otherwise combine the FD and TD RR values from possibly overlapping frames based on a selected averaging time. The averaging time can be user selectable in some embodiments. For instance, if the averaging time is 30 seconds, the post-processing module 1620 can average the TD and/or FD values selected for overlapping frames falling within the 30 second period. The output of this averaging can be an overall RR value. In one embodiment, the post-processing module 1620 performs a weighted average in of the respective respiratory rate values. The post-processing module 1620 can, for instance, use the calculated confidence values as weights or to derive weights to be applied to the respiratory rate values.

The post-processing module 1620 can similarly average the TD and RR confidence values to obtain an overall confidence value. Various combinations can be used to obtain the overall confidence value. For example, the confidence values can be averaged (and possibly weighted) over several confidence values. Also, a number of nonzero points can be selected from a buffer of confidence values and divided by the total number of points in the buffer. For example, if a buffer has five total confidence measurements, and two of those are zero, the overall confidence value could be ⅗. Also, the overall confidence value could be a combination of the weighted average and the nonzero-based confidence calculation. Many other embodiments are possible.

Figure 16B:
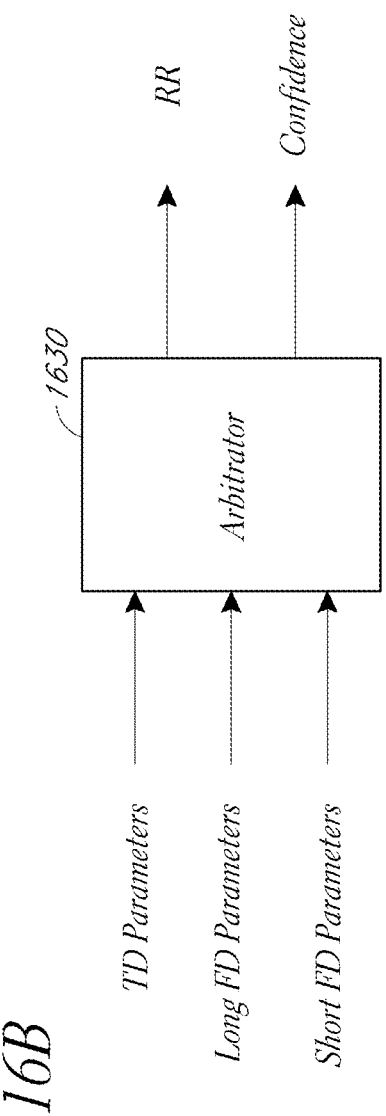
FIG. 16B illustrates another embodiment of an arbitrator.

An alternative embodiment to the arbitrator 1600 is illustrated in FIG. 16B. The arbitrator 1630 includes decision logic for determining respiratory rate and confidence values based on various inputs. The arbitrator 1630 receives time domain parameters, long frequency domain parameters, and short frequency domain parameters. From these parameters, the arbitrator 1630 outputs an overall respiratory rate and confidence value or indication.

In one embodiment, the time domain parameters include each respiratory rate value calculated during a given window, corresponding time stamps for the respiratory rate values, confidence values for each respiratory rate value, and an occurrence value for each respiratory rate value (see FIGS. 11B through 11D). The time domain parameters can also include the average time domain respiratory rate and time domain confidence described above for a given frame or processing window.

The long frequency domain parameters can include the frequency domain respiratory rate and confidence value calculated for a given frame or processing window. Likewise, the long frequency domain parameters can also include time stamps for the respiratory rate values and optionally occurrence values (which may be 1). In contrast, the short frequency domain parameters can include multiple respiratory rate and corresponding confidence values in a given time window. These parameters are referred to as short because a shorter time window (within the main frame or processing window) is used to calculate multiple respiratory rate values.

Figure 16C:
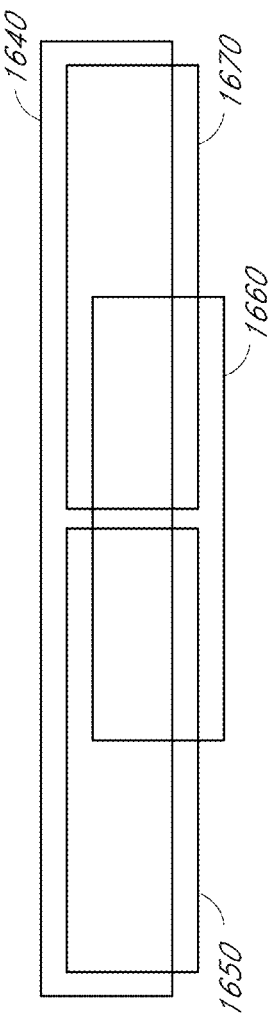
FIG. 16C illustrates an embodiment of a processing frame for processing a long frequency transform and short frequency transforms.

An illustration of calculating the short frequency domain parameters is shown with respect to FIG. 16C. In FIG. 16C, a frame 1640 or primary processing window is shown. The frame can include samples over a period of time, such as several seconds (e.g., 30 seconds). Subframes 1650, 1660, and 1670 are superimposed on the frame 1640 to illustrate subdivisions of the samples in the frame 1640. The subframes 1650, 1660, and 1670 are used to calculate the short frequency domain parameters. In the depicted embodiment, three subframes 1650, 1660, and 1670 are shown; however, two, four, or more subframes can be used to calculate the short frequency domain parameters.

In one embodiment, the time domain and frequency domain envelopes are calculated for the frame 1640, using the techniques described above. The long frequency domain parameters are thus derived from the frame 1640. The short frequency domain parameters are derived from frequency envelopes for each subframe 1650, 1660, and 1670. The frequency domain processor described above can calculate a separate respiratory rate and associated confidence value for each subframe 1650, 1660, and 1670, as well as associated time stamps and optionally occurrence values (which may be 1). These short frequency domain parameters can be used in decision logic of the arbitrator 1630 of FIG. 16B to improve respiratory rate calculations.

In certain embodiments, a logical module used to calculate the short frequency domain parameters can be considered a second frequency domain processor or engine. Thus, the respiration processor 314 of FIG. 3 can output respiratory rate values from three engines, instead of two. More engines can be used in other embodiments.

Figure 17A:
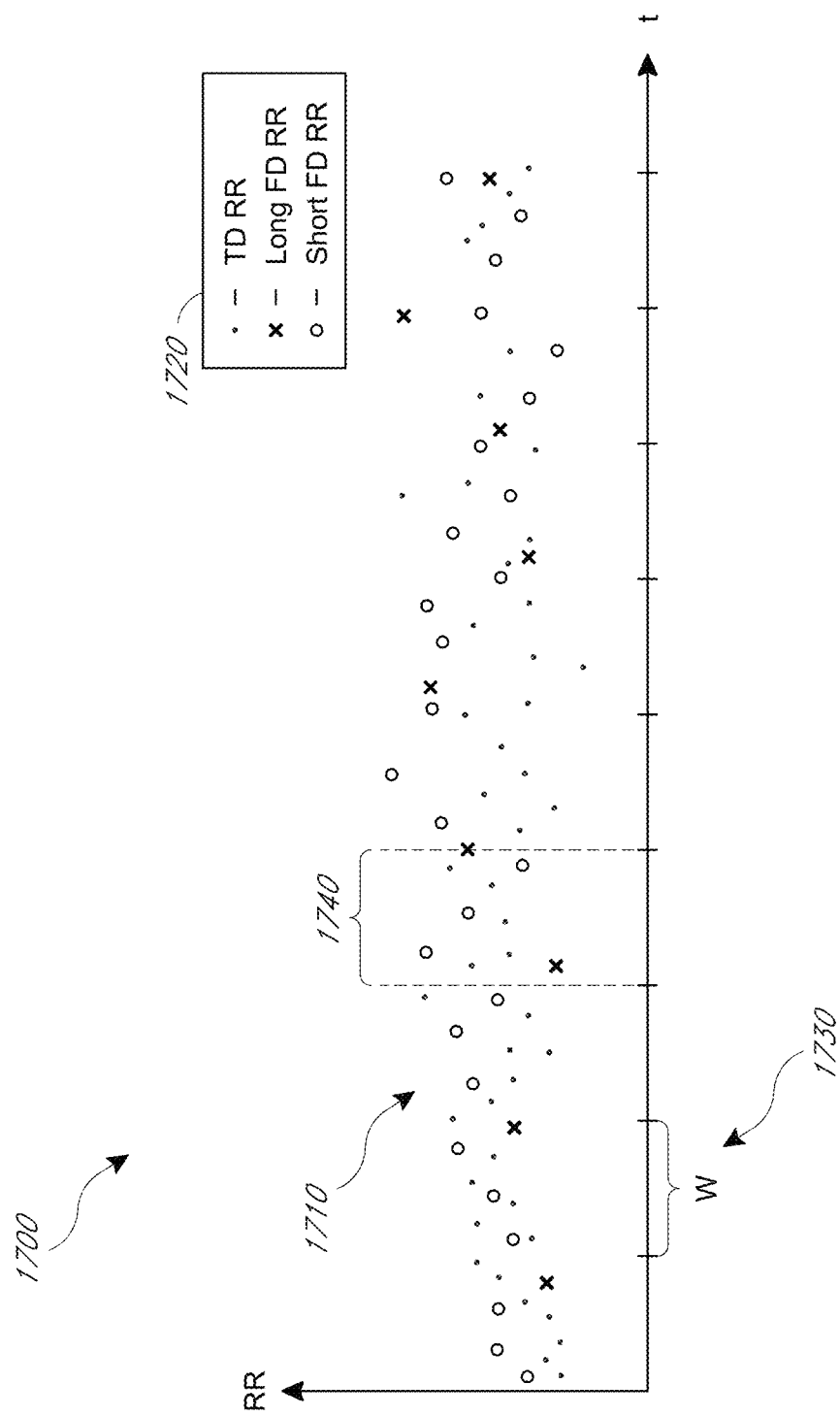
FIG. 17A illustrates an embodiment of plot depicting a respiratory rate point cloud.
Figure 17B:
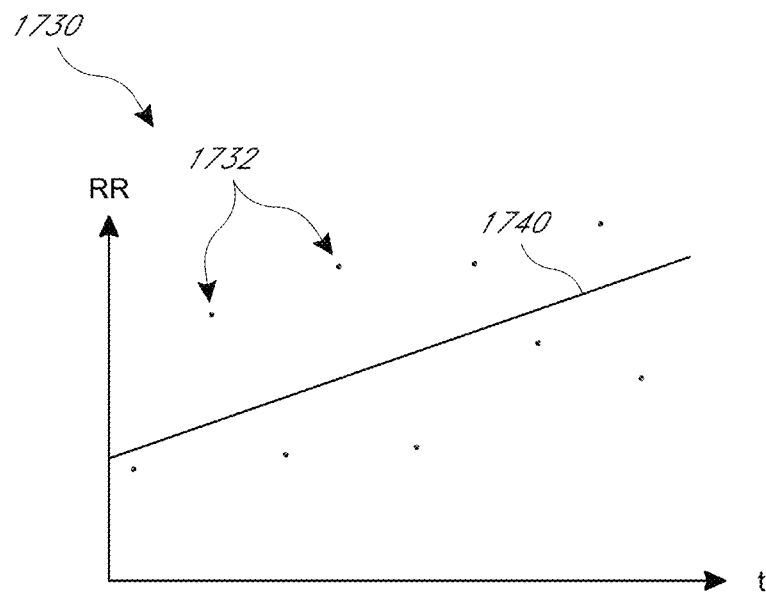
FIGS. 17B and 17C illustrate embodiments of plots depicting example curve fitting for the point cloud of FIG. 17A.
Figure 17C:
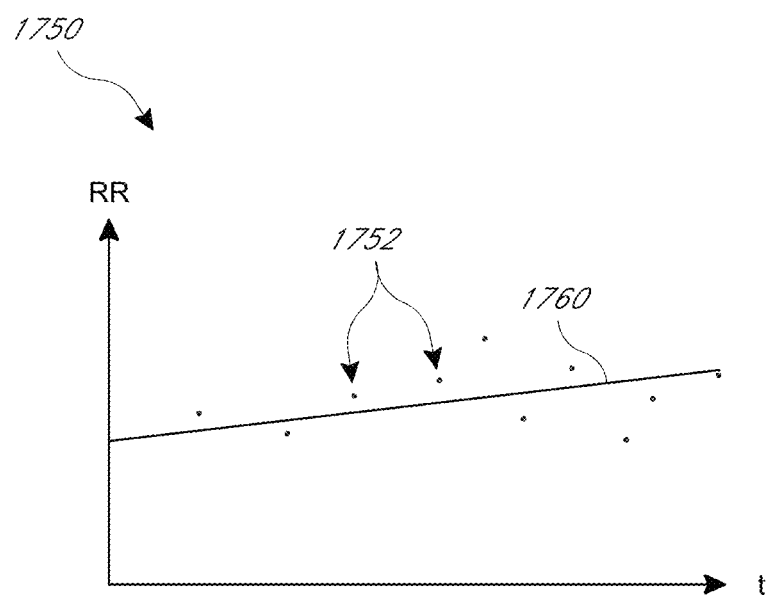
Figure 18:
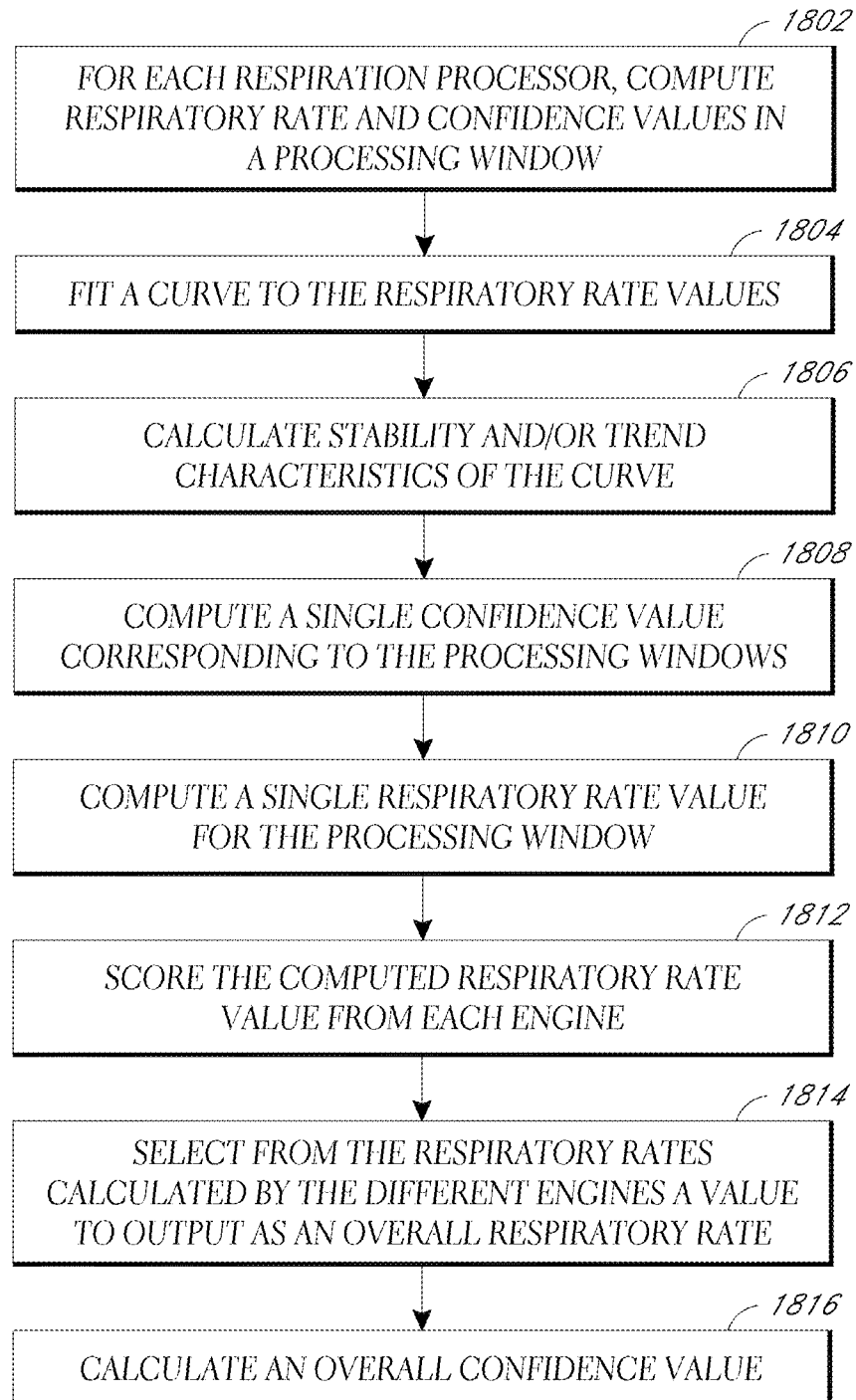
FIG. 18 illustrates an embodiment of a decision logic process.

Example features of the arbitrator 1630 can be explained in the context of FIGS. 17A through 18. In FIG. 17A, a point cloud plot 1700 is depicted. The point cloud plot 1700 graphs respiratory rate values over time. Thus, points 1710 in the point cloud plot 1700 represent discrete respiratory rate values. The point cloud plot 1700 can, but need not, be actually generated, but is used herein as a tool to describe arbitration between different time domain and frequency domain respiration processors.

The points 1710 in the point cloud plot 1700 represent time domain respiratory rate values, long frequency domain respiratory rate values, and short frequency domain respiratory rate values, as indicated by the legend 1720. The time axis of the plot 1700 is divided into frames or processing windows 1730. In certain embodiments, possibly multiple time domain respiratory rate values can be calculated for each window 1730. A single long frequency domain respiratory rate value can be calculated in each window 1730, and multiple short frequency domain respiratory rate values can be calculated in each window 1730 (see FIG. 16C).

The point cloud plot 1700 reflects trends in the respiratory rate values over time. These trends can be analyzed to determine one or more measures of how accurate respiratory rate values are for each time domain and frequency domain processor. An analysis window 1740 can be used to analyze these trends and other statistical measurements. The analysis window 1740 can be the same as the current processing window 1730 or can cover multiple processing windows 1730.

Respiratory rate data from example analysis windows is shown in more detail in FIGS. 17B and 17C. FIG. 17B depicts a plot 1730 of respiratory rate over time and is a subplot of the point cloud plot 1700. FIG. 17C depicts a similar plot 1750 that is also a subplot of the point cloud plot 1700. Points 1732, 1752 in each plot can represent respiratory rate values obtained from one of the respiration engines (e.g., time domain, long frequency domain, or short frequency domain). A fitted curve 1740, 1760 is shown in each plot. The fitted curves 1740, 1760 represent curves constructed to have a best (or estimated best) fit to the points 1732, 1752 in each plot.

Generally, the arbitrator 1730 of FIG. 16B can fit curves to respiratory rate points for each respiration engine and each analysis window 1740 (see FIG. 17A). Curves can be fit using any of a variety of methods, such as linear regression, spline functions, Bezier curves, or the like. In one embodiment, the curves are fit at least in part by taking confidence values for each respiratory rate value into account. The confidence values can act as weights in the point cloud, with higher confidence values giving greater weight to the points in the point cloud. Thus, for respiratory rate values having higher confidence, the curve fit to those points can be closer to those points than for respiratory rate values having lower confidence.

Each curve can be assessed by the arbitrator 1630 to determine the quality of an engine's respiratory rate values. This quality can be analyzed to score the outputs of the different respiration engines. One measure of quality is the stability, or goodness-of-fit, of the curves 1740, 1760. In the plot 1730, the curve 1740 has a relatively large degree of error due to the wide dispersion of the points 1732. Thus, the stability of this curve 1740 is relatively low. In contrast, the points 1752 in the plot 1750 are less dispersed, and the stability of the curve 1760 is therefore higher. Stability can be calculated, for example, with the minimum mean square error or some other similar measurement. A curve with higher stability reflects a better set of respiratory rate data for a particular engine. The arbitrator 1630 of FIG. 16B can use this stability information, at least in part, to select or arbitrate between different respiratory rate values from different engines.

In addition, a slope of the curves 1740, 1760 can be used to assess the quality of the respiratory rate values. A more positive or more negative slope can reflect a trend among respiratory rate values within a processing window. Because a processing window is a relatively short amount of time in certain embodiments, a patient's respiration rate is likely not changing significantly. Thus, a trend can reflect lower quality respiratory rate data. Conversely, a flatter curve can reflect possibly more accurate respiratory rate data. The curve 1740 has a higher slope than the curve 1760, reflecting possibly lower quality respiratory rate data.

FIG. 18 illustrates a decision logic process 1800 for selecting respiratory rate measurements. The process 1800 ties together the techniques described above with respect to FIGS. 16B through 17C and can be implemented by the arbitrator 1630 of FIG. 16. In certain embodiments, some or all features of the process 1800 can also be combined with features of the arbitrator 1600 described above with respect to FIG. 16A.

At block 1802, for each respiration processor or engine, one or more respiratory rate and confidence values are computed in a processing window. Thus, for example, time domain respiratory rate and confidence values can be calculated, long frequency domain values can be calculated, and short frequency domain values can be calculated. Blocks 1804 through 1820 of the process 1800 are described from the perspective of a single engine. At block 1804, a curve is fit to the respiratory rate values, using any of the techniques described above with respect to FIG. 17. An actual curve need not be drawn on a display although one can be; rather, values for such a curve can be stored in memory (volatile or nonvolatile). Stability and/or trend characteristics of the curve are calculated at block 1806.

A single confidence value is computed for the processing window at block 1808. This confidence value can be the average of the confidence values of each respiratory rate value calculated in the time domain (with a possible weighting applied with the occurrence value). The confidence value can also be an average for the short frequency domain engine. The confidence value from the long frequency domain engine can be the single confidence value computed (or rather, accessed) at block 1808.

Similarly, a single respiratory rate value is computed for each engine at block 1810. The time domain respiratory rate value can be computed using a simple or weighted average (see FIGS. 11B through 11D). Similarly, the short frequency domain respiratory rate values can be computed with a simple or weighted average, and the long frequency domain respiratory rate value can simply be accessed (e.g., from memory).

The computed respiratory rate values from each engine are scored at block 1812. This scoring can be based on the stability and/or trend values computed above, among other factors. Other factors might include, for example, how close the respiratory rate value for each engine is. Two engines with close respiratory rate values might be given bonus points in the scoring algorithm, while an outlier is not given bonus points (or is docked points). The score can also be based on the confidence values.

An overall respiratory rate value is selected from the scored respiratory rates at block 1814. The overall respiratory rate value can be selected based at least partly on the scores calculated above with respect to block 1812. Confidence values can be used as a tiebreaker between the respiratory rate values of different engines in certain embodiments. In one embodiment, respiratory rate values from different engines can be combined or averaged to produce the overall respiratory rate value. The combination of the respiratory rate values can be done as a weighted average, for example, using confidence values (or derivatives thereof) as weights.

An overall confidence value is calculated at block 1816. The overall confidence value can be the confidence value of the respiratory rate value that was selected from a particular engine as the overall respiratory rate. If the respiratory rate values from different engines were combined at block 1814, the confidence values may likewise be combined.

As described above, the arbitrator 1630 can average respiratory rate values and confidence values over time, such as a plurality of processing windows. If the overall confidence value is low and the respiratory rate value is therefore considered unreliable, in one embodiment the arbitrator 1630 lengthens this averaging time. The lengthened averaging time can reduce the impact of invalid or low quality respiratory rate values on the overall respiratory rate value output to a display of a patient monitor. Conversely, higher confidence values can cause the arbitrator 1630 to decrease the averaging time.

Terminology

The modules described herein of certain embodiments may be implemented as software modules, hardware modules, or a combination thereof. In general, the word "module," as used herein, can refer to logic embodied in hardware or firmware or to a collection of software instructions executable on a processor. Additionally, the modules or components thereof may be implemented in analog circuitry in some embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A system for determining a respiration rate of a patient using an acoustic signal received from an acoustic sensor adapted to monitor the patient, the system comprising:
   an input configured to receive the acoustic signal from the acoustic sensor; and
   one or more hardware processors configured to:
      generate a time domain envelope signal from the acoustic signal, individually tag each local extremum of a plurality of local extrema in the time domain envelope signal as potentially corresponding to an inspiration or an expiration of the patient, determine to reject at least one local extremum of the plurality of local extrema as not corresponding to the inspiration or the expiration, determine in real time a respiratory rate from the plurality of local extrema without using the at least one local extremum that was determined to be rejected, and output the respiratory rate.

2. The system of claim 1, wherein the one or more hardware processors are configured to determine to reject a first local extremum of the plurality of local extrema according to a time difference between the first local extremum and a second local extremum of the plurality of local extrema, the at least one local extremum that was determined to be rejected comprising the first local extremum.

3. The system of claim 2, wherein the first local extremum and the second local extremum are consecutively-occurring local extrema in the time domain envelope signal.

4. The system of claim 2, wherein the one or more hardware processors are configured to determine to reject the first local extremum further according to a magnitude difference between a first magnitude of the first local extremum and a second magnitude of the second local extremum.

5. The system of claim 2, wherein the one or more hardware processors are configured to:

determine to reject the first local extremum from a comparison of the time difference and a threshold, and adjust the threshold.

6. The system of claim 5, wherein the one or more hardware processors are configured to:

determine that the patient is a neonate, and adjust the threshold responsive to determining that the patient is the neonate.

7. The system of claim 1, wherein the one or more hardware processors are configured to determine to reject a first local extremum of the plurality of local extrema according to a change in a magnitude of the time domain envelope signal between the first local extremum and a second local extremum of the plurality of local extrema, the at least one local extremum that was determined to be rejected comprising the first local extremum.

8. The system of claim 1, wherein the one or more hardware processors are configured to determine to reject a first local extremum of the plurality of local extrema because the first local extremum is at a beginning or an end of a processing unit, the processing unit corresponding to a set of the plurality of local extrema that the one or more hardware processors are configured to process as a batch, the at least one local extremum that was determined to be rejected comprising the first local extremum.

9. The system of claim 1, wherein the one or more hardware processors are configured to determine to reject a first local extremum of the plurality of local extrema according to a width of the time domain envelope signal around the first local extremum, the at least one local extremum that was determined to be rejected comprising the first local extremum.

10. The system of claim 1, wherein the one or more hardware processors are configured to:

determine a statistical parameter from processing a set of the plurality of local extrema as a batch, the set of the plurality of local extrema not comprising a first local extremum of the plurality of local extrema, and determine to reject the first local extremum from a deviation of a characteristic of the first local extremum relative to the statistical parameter, the at least one local extremum that was determined to be rejected comprising the first local extremum.

11. The system of claim 1, wherein the one or more hardware processors are configured to:

filter the time domain envelope signal with a filter to smooth the time domain envelope signal, the filter having a cutoff frequency, and adjust the cutoff frequency.

12. The system of claim 11, wherein the one or more hardware processors are configured to adjust the cutoff frequency responsive to the respiratory rate.

13. The system of claim 1, wherein the one or more hardware processors are configured to individually tag each local extremum of the plurality of local extrema by identifying any local extremum of the plurality of local extrema in the time domain envelope signal that are between a lower threshold and an upper threshold, the lower threshold corresponding to a noise floor.

14. The system of claim 1, further comprising:

the acoustic sensor; or a display configured to present the respiratory rate.

15. A method for determining a respiration rate of a patient using an acoustic signal received from an acoustic sensor monitoring the patient, the method comprising:

detecting, using the acoustic sensor, the acoustic signal;

generating, by one or more hardware processors, a time domain envelope signal from the acoustic signal;

individually tagging, by the one or more hardware processors, each local extremum of a plurality of local extrema in the time domain envelope signal as potentially corresponding to an inspiration or an expiration of the patient;

determining, by the one or more hardware processors, to reject at least one local extremum of the plurality of local extrema as not corresponding to the inspiration or the expiration;

determining, by the one or more hardware processors, in real time a respiratory rate from the plurality of local extrema without using the at least one local extremum that was determined to be rejected; and presenting the respiratory rate on a display.

16. The method of claim 15, wherein said determining to reject the at least one local extremum comprises determining to reject a first local extremum of the plurality of local extrema according to a time difference between the first local extremum and a second local extremum of the plurality of local extrema, the first local extremum and the second local extremum being consecutively-occurring local extrema in the time domain envelope signal, the at least one local extremum that was determined to be rejected comprising the first local extremum.

17. The method of claim 16, wherein said determining to reject the at least one local extremum comprises determining to reject the first local extremum from a comparison of the time difference and a threshold, and further comprising:

determining that the patient is a neonate; and adjusting the threshold responsive to determining that the patient is the neonate.

18. The method of claim 15, wherein said determining to reject the at least one local extremum comprises determining to reject a first local extremum of the plurality of local extrema according to a change in a magnitude of the time domain envelope signal between the first local extremum and a second local extremum of the plurality of local extrema, the first local extremum and the second local extremum being consecutively-occurring local extrema in the time domain envelope signal, the at least one local extremum that was determined to be rejected comprising the first local extremum.

19. The method of claim 15, further comprising:
   filtering the time domain envelope signal with a filter to smooth the time domain envelope signal, the filter having a cutoff frequency; and
   adjusting the cutoff frequency responsive to the respiratory rate.

20. The method of claim 15, wherein said tagging comprises identifying any local extremum of the plurality of local extrema in the time domain envelope signal that are between a lower threshold and an upper threshold.

* * * * *